US008841321B2

(12) United States Patent
Andries et al.

(10) Patent No.: US 8,841,321 B2
(45) Date of Patent: *Sep. 23, 2014

(54) QUINOLINE DERIVATIVES AS ANTIBACTERIAL AGENTS

(75) Inventors: Koenraad Jozef Lodewijk Marcel Andries, Beerse (BE); Anil Koul, Berchem (BE); Jérôme Emile Georges Guillemont, Ande (FR); David Francis Alain Lançois, Louviers (FR); Magali Madeleine Simone Motte, Val de Reuil Cedex (FR); Ismet Dorange, Val de Reuil Cedex (FR); Leo Jacobus Jozef Backx, Beerse (BE); Lieven Meerpoel, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 1602 days.

This patent is subject to a terminal disclaimer.

(21) Appl. No.: 11/993,145

(22) PCT Filed: Jun. 26, 2006

(86) PCT No.: PCT/EP2006/063553
§ 371 (c)(1),
(2), (4) Date: Dec. 19, 2007

(87) PCT Pub. No.: WO2007/000435
PCT Pub. Date: Jan. 4, 2007

(65) Prior Publication Data
US 2010/0048585 A1     Feb. 25, 2010

(30) Foreign Application Priority Data
Jun. 28, 2005   (EP) .................................. 05105762

(51) Int. Cl.
| A01N 43/42 | (2006.01) |
| A61K 31/47 | (2006.01) |
| A01N 43/40 | (2006.01) |
| A61K 31/445 | (2006.01) |
| A61K 31/44 | (2006.01) |
| C07D 215/227 | (2006.01) |

(52) U.S. Cl.
CPC ............ A61K 31/47 (2013.01); C07D 215/227 (2013.01)
USPC ........... 514/312; 514/313; 514/314; 514/318; 514/336; 514/340; 546/153; 546/156

(58) Field of Classification Search
CPC . A61K 31/47; A61K 31/4704; A61K 215/00; A61K 215/227
USPC .......... 514/312–314, 318, 336, 340; 546/153, 546/156
See application file for complete search history.

(56) References Cited

FOREIGN PATENT DOCUMENTS

| WO | WO2004/011436 A1 * | 2/2004 |
| WO | WO 2004/011436 | 5/2004 |

(Continued)

OTHER PUBLICATIONS

MedlinePlus [Retrieved online on Mar. 8, 2011 from the Internet: <URL: http://www.nlm.nih.gov/medlineplus/ency/article/007261. htm].*

(Continued)

Primary Examiner — Kendra D Carter
(74) Attorney, Agent, or Firm — Thomas J. Dodd

(57) ABSTRACT

Use of a compound for the manufacture of a medicament for the treatment of a bacterial infection provided that the bacterial infection is other than a Mycobacterial infection, said compound being a compound of formula (Ia) or (Ib) a pharmaceutically acceptable acid or base addition salt thereof, a stereochemically isomeric form thereof, a tautomeric form thereof or a N-oxide form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl; p is 1, 2, 3 or 4; $R^2$ is hydrogen, hydroxy, mercapto, alkyloxy, alkyloxyalkyloxy, alkylthio, mono or di(alkyl)amino or a radical of formula; $R^3$ is alkyl, Ar, Ar-alkyl, Het or Het-alkyl; q is 1, 2 or 3; $R^4$ and $R^5$ are hydrogen, alkyl or benzyl; or $R^4$ and $R^5$ together and including the N to which they are attached may form a ring; $R^6$ is hydrogen, halo, haloalkyl, hydroxy, Ar, alkyl, alkyloxy, alkylthio, alkyloxyalkyl, alkythioalkyl, Ar-alkyl or di(Ar)alkyl; or two vicinal $R^6$ radicals may be taken together to form a bivalent radical of formula —CH=CH—CH=CH—; r is 1, 2, 3, 4 or 5; $R^7$ is hydrogen, alkyl, Ar or Het; $R^8$ is hydrogen or alkyl; $R^9$ is oxo; or $R^8$ and $R^9$ together form the radical —CH=CH—N=.

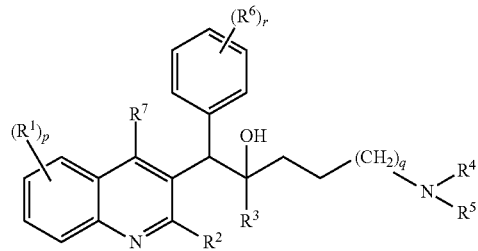

(Ia)

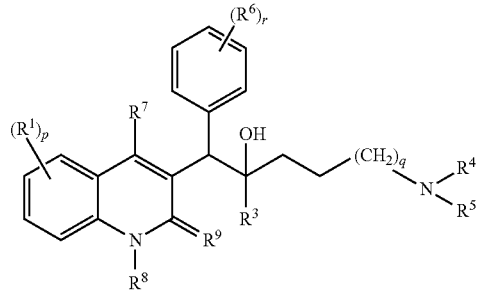

(Ib)

26 Claims, No Drawings

(56) References Cited

FOREIGN PATENT DOCUMENTS

| | | |
|---|---|---|
| WO | WO 2005/033108 | 4/2005 |
| WO | WO 2005/117875 | 12/2005 |
| WO | WO 2006/067048 | 6/2006 |
| WO | WO 2007/000434 A1 | 1/2007 |

OTHER PUBLICATIONS

Patel et al. (Occup. Med., vol. 50, No. 6, pp. 392-394; 2000).*

International Search Report dated Sep. 4, 2006 for related International Application No. PCT/EP2006/063553.
XP-000944820—P. K. Desai et al., "Quinoline derivatives as antitubercular/antibacterial agents", Indian Journal of Chemistry, vol. 35B, Aug. 1996, pp. 871-873.
Andries, K, et al. "A Diarylquinoline Drug Active on the ATP Synthase of *Mycobacterium tuberculosis*", Science, vol. 307 (2005) pp. 223-227.
Helwig, B., et al. "A Specialty for Indication Areas for Physicians and Pharmacists", Modern Drugs, 5th Fully revised edition, Scientific Printing Company, mbH, Stuttgart (1980) With English Translation.

* cited by examiner

QUINOLINE DERIVATIVES AS ANTIBACTERIAL AGENTS

CROSS REFERENCE TO RELATED APPLICATIONS

This application is a national stage application of Patent Application No. PCT/EP2006/063553, filed Jun. 26, 2006, which in turn claims the benefit of EPO Patent Application No. 05105762.8, filed Jun. 28, 2005. The complete disclosures of the aforementioned related patent applications are hereby incorporated herein by reference for all purposes.

The present invention relates to the use of quinoline derivatives for the manufacture of a medicament for the treatment of a bacterial infection.

Resistance to first-line antibiotic agents is an emerging problem. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection.

Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially for the treatment of infections caused by resistant strains.

WO 2004/011436 discloses substituted quinoline derivatives having activity against *Mycobacteria*, in particular against *Mycobacterium tuberculosis*. One particular compound of these substituted quinoline derivatives is described in Science (2005), 307, 223-227.

It has now been found that quinoline derivatives described in WO 2004/011436 also show activity against other bacteria than *Mycobacteria*.

Therefore, the present invention relates to the use of a compound for the manufacture of a medicament for the treatment of a bacterial infection, said compound being a compound of formula (Ia) or (Ib)

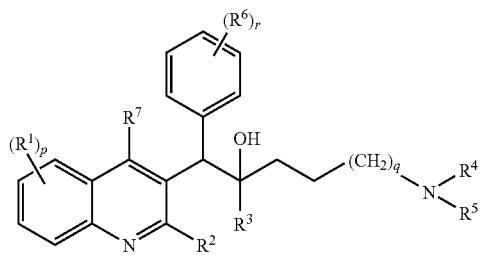

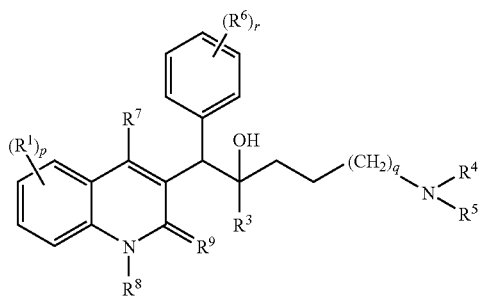

a pharmaceutically acceptable acid or base addition salt thereof, a stereochemically isomeric form thereof, a tautomeric form thereof or a N-oxide form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2, 3 or 4;

$R^2$ is hydrogen, hydroxy, mercapto, alkyloxy, alkyloxyalkyloxy, alkylthio, mono or di(alkyl)amino or a radical of formula

wherein Y is $CH_2$, O, S, NH or N-alkyl;

$R^3$ is alkyl, Ar, Ar-alkyl Het or Het-alkyl;

q is an integer equal to 1, 2 or 3;

$R^4$ and $R^5$ each independently are hydrogen, alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl pyrimidinyl pyrazinyl triazinyl, morpholinyl and thiomorpholinyl, optionally substituted with alkyl, halo, haloalkyl, hydroxy, alkyloxy, amino, mono- or dialkylamino, alkylthio, alkyloxyalkyl alkylthioalkyl or pyrimidinyl;

$R^6$ is hydrogen, halo, haloalkyl, hydroxy, Ar, alkyl, alkyloxy, alkylthio, alkyloxyalkyl alkylthioalkyl Ar-alkyl or di(Ar)alkyl; or two vicinal $R^6$ radicals may be taken together to form a bivalent radical of formula —CH=CH—CH=CH—;

r is an integer equal to 1, 2, 3, 4 or 5;

$R^7$ is hydrogen, alkyl, Ar or Het;

$R^8$ is hydrogen or alkyl;

$R^9$ is oxo; or $R^8$ and $R^9$ together form the radical —CH=CH—N=;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;

Ar is a homocycle selected from the group of phenyl, naphthyl, acenaphthyl, tetrahydronaphthyl, each homocycle optionally substituted with 1, 2 or 3 substituents, each substituent independently selected from the group of hydroxy, halo, cyano, nitro, amino, mono- or dialkylamino, alkyl haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl and benzo[1,3]dioxolyl; each monocyclic and bicyclic heterocycle may optionally be substituted with 1, 2 or 3 substituents, each substituent independently selected from the group of halo, hydroxy, alkyl, alkyloxy, and Ar-carbonyl;

halo is a substituent selected from the group of fluoro, chloro, bromo and iodo; and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms;

provided that the bacterial infection is other than a Mycobacterial infection.

The present invention also relates to a method of treating a bacterial infection in a mammal, in particular a warm-blooded mammal, more in particular a human, comprising administering an effective amount of a compound of the invention to the mammal.

The compounds according to Formula (Ia) and (Ib) are interrelated in that e.g. a compound according to Formula (Ib), with $R^9$ equal to oxo is the tautomeric equivalent of a compound according to Formula (Ia) with $R^2$ equal to hydroxy (keto-enol tautomerism).

In the framework of this application, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo.

Preferably, alkyl is methyl, ethyl or cyclohexylmethyl, more preferably methyl or ethyl. An interesting embodiment of alkyl in all definitions used hereinbefore or hereinafter is $C_{1-6}$alkyl which represents a straight or branched saturated hydrocarbon radical having from 1 to 6 carbon atoms such as for example methyl, ethyl, propyl, 2-methyl-ethyl, pentyl, hexyl and the like. A preferred subgroup of $C_{1-6}$alkyl is $C_{1-4}$alkyl which represents a straight or branched saturated hydrocarbon radical having from 1 to 4 carbon atoms such as for example methyl, ethyl, propyl, 2-methyl-ethyl and the like.

In the framework of this application, Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl haloalkyl, alkyloxy, haloalkyloxy, carboxyl, alkyloxycarbonyl, aminocarbonyl, morpholinyl and mono- or dialkylaminocarbonyl. Preferably, Ar is naphthyl or phenyl, each optionally substituted with 1 or 2 substituents independently selected from halo or alkyloxy.

In the framework of this application, Het is a monocyclic heterocycle selected from the group of N-phenoxypiperidinyl, piperidinyl, pyrrolyl, pyrazolyl, imidazolyl, furanyl, thienyl oxazolyl isoxazolyl, thiazolyl, isothiazolyl, pyridinyl, pyrimidinyl pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl and benzo[1,3]dioxolyl; each monocyclic and bicyclic heterocycle may optionally be substituted with 1, 2 or 3 substituents, each substituent independently selected from the group of halo, hydroxy, alkyl, alkyloxy and Ar-carbonyl. Preferably, Het is furanyl, piperidinyl, pyridinyl or benzo[1,3]dioxolyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms. Preferably, halo is bromo, fluoro or chloro and preferably, haloalkyl is polyhalo$C_{1-6}$alkyl which is defined as mono- or polyhalosubstituted $C_{1-6}$alkyl, for example, methyl with one or more fluoro atoms, for example, difluoromethyl or trifluoromethyl, 1,1-difluoro-ethyl and the like. In case more than one halo atom is attached to an alkyl group within the definition of haloalkyl or polyhalo$C_{1-6}$alkyl, they may be the same or different.

In the definition of Het, it is meant to include all the possible isomeric forms of the heterocycles, for instance, pyrrolyl comprises 1H-pyrrolyl and 2H-pyrrolyl.

The Ar or Het listed in the definitions of the substituents of the compounds of formula (Ia) or (Ib) (see for instance $R^3$) as mentioned hereinbefore or hereinafter may be attached to the remainder of the molecule of formula (Ia) or (Ib) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

When two vicinal $R^6$ radicals are taken together to form a bivalent radical of formula —CH=CH—CH=CH—, this means that the two vicinal $R^6$ radicals form together with the phenyl ring to which they are attached a naphthyl.

For therapeutic use, salts of the compounds of formula (Ia) or (Ib) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable addition salts as mentioned hereinabove or hereinafter are meant to comprise the therapeutically active non-toxic acid addition salt forms which the compounds of formula (Ia) or (Ib) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tarric, 2-hydroxy-1,2,3-propanetricarboxylic, methanesulfonic, ethanesulfonic, benzenesulfonic, 4-methyl-benzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (Ia) or (Ib) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (Ia) or (Ib) are able to form. Examples of such forms are e.g. hydrates, alcoholates and the like.

The N-oxide forms of the present compounds are meant to comprise the compounds of formula (Ia) or (Ib) wherein one or several tertiary nitrogen atoms are oxidized to the so-called N-oxide.

The compounds of formula (Ia) and (Ib) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t. butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

It will be appreciated that some of the compounds of formula (Ia) and (Ib) and their N-oxides or addition salts may contain one or more centres of chirality and exist as stereochemically isomeric forms.

Compounds of either formula (Ia) and (Ib) and some of the intermediate compounds invariably have at least two stereogenic centers in their structure which may lead to at least 4 stereochemically different structures.

The term "stereochemically isomeric forms" as used hereinbefore or hereinafter defines all the possible stereoisomeric forms which the compounds of formula (Ia) and (Ib), and their N-oxides, addition salts or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art.

Stereochemically isomeric forms of the compounds of formula (Ia) and (Ib) are obviously intended to be embraced within the scope of this invention.

Following CAS-nomenclature conventions, when two stereogenic centers of known absolute configuration are present in a molecule, an R or S descriptor is assigned (based on Caln-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (Ia) or (Ib) is for instance specified as (αS, βR), this means that the compound is substantially free of the (αR, βS) isomer.

The compounds of either formula (Ia) and (Ib) may be synthesized in the form of racemic mixtures of enantiomers which can be separated from one another following art-known resolution procedures. The racemic compounds of either formula (Ia) and (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of either formula (Ia) and (Ib) are meant to comprise those compounds of either formula (Ia) and (Ib) wherein e.g. an enol group is converted into a keto group (keto-enol tautomerism).

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 1112-176, and *Drugs*, 1985, 29, pp. 455-473.

Pro-drugs forms of the pharmacologically-active compounds according to the invention will generally be compounds according to either Formula (Ia) and (Ib), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

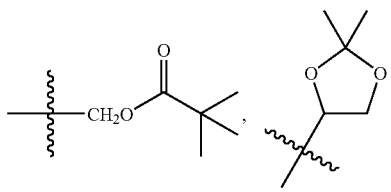

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

Whenever used herein, the term "compounds of formula (Ia) or (Ib)" is meant to also include their pharmaceutically acceptable acid or base addition salts, their N-oxide forms, their tautomeric forms or their stereochemically isomeric forms. Of special interest are those compounds of formula (Ia) or (Ib) which are stereochemically pure.

A first interesting embodiment of the present invention relates to a compound of formula (Ia-1) or (Ib-1)

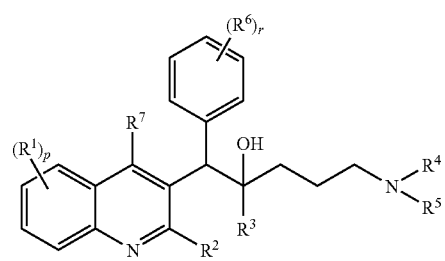

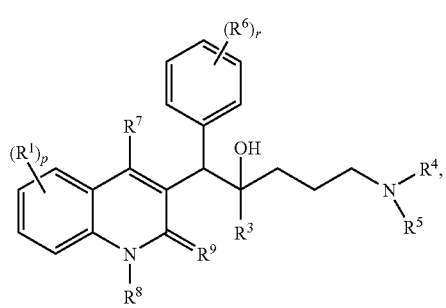

a pharmaceutically acceptable acid or base addition salt thereof, a stereochemically isomeric form thereof, a tautomeric form thereof or a N-oxide form thereof.

A second interesting embodiment of the present invention relates to a compound of formula (Ia-2) or (Ib-2)

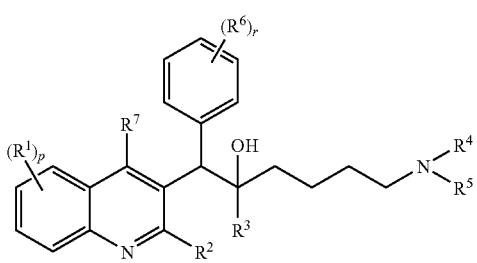

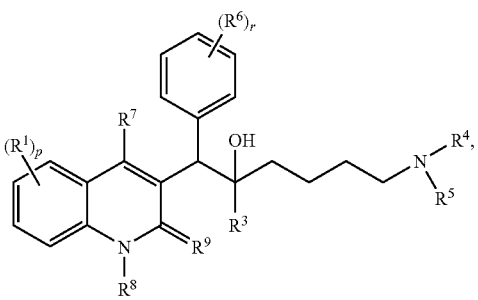

a pharmaceutically acceptable acid or base addition salt thereof, a stereochemically isomeric form thereof, a tautomeric form thereof or a N-oxide form thereof.

A third interesting embodiment of the present invention relates to a compound of formula (Ia-3) or (Ib-3)

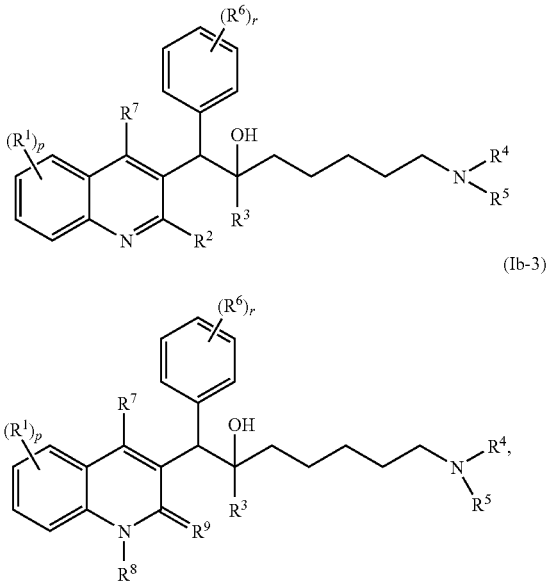

(Ia-3)

(Ib-3)

a pharmaceutically acceptable acid or base addition salt thereof, a stereochemically isomeric form thereof, a tautomeric form thereof or a N-oxide form thereof.

A fourth interesting embodiment relates to a compound of formula (Ia) or (Ib) or any subgroup thereof as mentioned hereinbefore as interesting embodiment wherein
$R^1$ is hydrogen, halo, cyano, Ar, Het, alkyl, and alkyloxy;
p is an integer equal to 1, 2, 3 or 4; in particular 1 or 2;
$R^2$ is hydrogen, hydroxy, alkyloxy, alkyloxyalkyloxy, alkylthio or a radical of formula

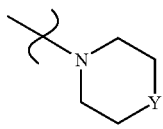

wherein Y is O;
$R^3$ is alkyl, Ar, Ar-alkyl or Het;
q is an integer equal to 1 or 2;
$R^4$ and $R^5$ each independently are hydrogen, alkyl or benzyl; or
$R^6$ is hydrogen, halo or alkyl; or
two vicinal $R^6$ radicals may be taken together to form a bivalent radical of formula —CH═CH—CH═CH—;
r is an integer equal to;
$R^7$ is hydrogen;
$R^8$ is hydrogen or alkyl;
$R^9$ is oxo; or
$R^8$ and $R^9$ together form the radical CH═CH—N═;
alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;
Ar is a homocycle selected from the group of phenyl, naphthyl, acenaphthyl, tetrahydronaphthyl, each homocycle optionally substituted with 1, 2 or 3 substituents, each substituent independently selected from the group of halo, haloalkyl, cyano, alkyloxy and morpholinyl;
Het is a monocyclic heterocycle selected from the group of N-phenoxypiperidinyl, piperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]dioxolyl; each monocyclic and bicyclic heterocycle may optionally be substituted with 1, 2 or 3 alkyl or Ar-carbonyl substituents; and
halo is a substituent selected from the group of fluoro, chloro and bromo.

A fifth interesting embodiment relates to a compound of formula (Ia) or (Ib) or any subgroup thereof as mentioned hereinbefore as interesting embodiment wherein $R^1$ is hydrogen, halo, Ar, Het, alkyl or alkyloxy; preferably, $R^1$ is hydrogen, halo, Ar or Het, in particular, $R^1$ is hydrogen, halo, phenyl, furanyl or piperidinyl; more preferably, $R^1$ is halo or Het; most preferred, $R^1$ is halo, in particular bromo.

A sixth interesting embodiment relates to a compound of formula (Ia) or (Ib) or any subgroup thereof as mentioned hereinbefore as interesting embodiment wherein wherein p is equal to 1; preferably wherein p is equal to 1 and $R^1$ is other than hydrogen.

A seventh interesting embodiment relates to a compound of formula (Ia) or (Ib) or any subgroup thereof as mentioned hereinbefore as interesting embodiment wherein wherein p is equal to 1 and said $R^1$ substituent is placed in position 5, 6 or 7 of the quinoline ring; preferably in position 6.

An eighth interesting embodiment relates to a compound of formula (Ia) or (Ib) or any subgroup thereof as mentioned hereinbefore as interesting embodiment wherein $R^2$ is hydrogen, alkyloxy or alkylthio or a radical of formula

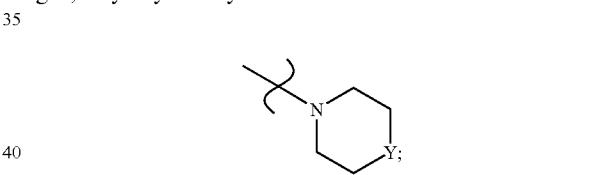

preferably, $R^2$ is hydrogen, alkyloxy or alkylthio; more preferably, $R^2$ is alkyloxy or alkylthio; even more preferably alkyloxy, in particular $C_{1-4}$alkyloxy; most preferred, $R^2$ is methyloxy.

A ninth interesting embodiment relates to a compound of formula (Ia) or (Ib) or any subgroup thereof as mentioned hereinbefore as interesting embodiment wherein $R^3$ is Ar, Het, Ar-alkyl, Het-alkyl or alkyl, each optionally substituted with 1 or 2 substituents, that substituent preferably being a halo, alkyl, haloalkyl or alkyloxy, in particular $R^3$ is $C_{1-4}$alkyl, naphthyl, phenyl optionally substituted with alkyl or alkyloxy, pyridinyl, benzo[1,3]dioxolyl, —CH$_2$—(CH$_2$)$_n$—R$^{3a}$ wherein $R^{3a}$ is cyclohexyl, phenyl, naphthyl or furanyl, $R^{3a}$ optionally being substituted with alkyl, and wherein n is 0 or 1; preferably, $R^3$ is Ar, Het or Ar-alkyl, each optionally substituted with 1 or 2 substituents, that substituent preferably being a halo, haloalkyl or alkyloxy, more preferably being a halo or alkyloxy, most preferably being a halo; preferably, $R^3$ is Ar or Het, each optionally substituted with 1 or 2 substituents selected from halo or alkyloxy; more preferably, $R^3$ is naphthyl, phenyl or Het; even more preferably $R^3$ is naphthyl phenyl, pyridinyl or benzo[1,3]dioxolyl; most preferred, $R^3$ is naphthyl, in particular 1-naphthyl or 2-naphthyl, or phenyl. Another preferred embodiment is $R^3$ representing Ar-alkyl optionally substituted with halo, alkyl, haloalkyl or alkyloxy.

A tenth interesting embodiment relates to a compound of formula (Ia) or (Ib) or any subgroup thereof as mentioned hereinbefore as interesting embodiment wherein $R^4$ and $R^5$ each independently are hydrogen, alkyl or benzyl; preferably hydrogen or alkyl, in particular hydrogen or $C_{1-4}$alkyl; more preferably $C_{1-4}$alkyl; most preferably methyl.

An eleventh interesting embodiment relates to a compound of formula (Ia) or (Ib) or any subgroup thereof as mentioned hereinbefore as interesting embodiment wherein $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl or pyrimidinyl; preferably $R^4$ and $R^5$ together and including the N to which they are attached may form a radical selected from the group of pyrrolidinyl, imidazolidinyl, pyrazolidinyl, piperidinyl, piperazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl or pyrimidinyl; more preferably $R^4$ and $R^5$ together and including the N to which they are attached may form a radical selected from the group of pyrrolidinyl, piperidinyl, piperazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl or pyrimidinyl; even more preferably, $R^4$ and $R^5$ together and including the N to which they are attached may form a radical selected from the group of pyrrolidinyl, piperidinyl, piperazinyl or morpholinyl, optionally substituted with alkyl, amino or mono- or di(alkyl)amino.

A twelfth interesting embodiment relates to a compound of formula (Ia) or (Ib) or any subgroup thereof as mentioned hereinbefore as interesting embodiment wherein $R^6$ is hydrogen, alkyl, alkyloxy, halo or Ar, in particular $R^6$ is hydrogen, halo, alkyloxy, alkyl or phenyl optionally substituted with alkyloxy; preferably, $R^6$ is hydrogen, alkyl, alkyloxy or halo; more preferably, $R^6$ is hydrogen or halo; most preferred $R^6$ is hydrogen.

A thirteenth interesting embodiment relates to a compound of formula (Ia) or (Ib) or any subgroup thereof as mentioned hereinbefore as interesting embodiment wherein r is 1 or 2; preferably r is 1.

A fourteenth interesting embodiment relates to a compound of formula (Ia) or (Ib) or any subgroup thereof as mentioned hereinbefore as interesting embodiment wherein $R^7$ is hydrogen or methyl; preferably $R^7$ is hydrogen.

A fifteenth interesting embodiment relates to a compound of formula (Ia) or (Ib) or any subgroup thereof as mentioned hereinbefore as interesting embodiment wherein, for compounds according to Formula (Ib) only, $R^8$ is alkyl, preferably methyl, and $R^9$ is oxygen.

A sixteenth interesting embodiment relates to a compound of formula (Ia) or (Ib) or any subgroup thereof as mentioned hereinbefore as interesting embodiment wherein the compound is a compound according to formula (Ia).

A seventeenth interesting embodiment relates to a compound of formula (Ia) or (Ib) or any subgroup thereof as mentioned hereinbefore as interesting embodiment wherein one or more, preferably all, of the following definitions apply:
$R^1$ is hydrogen, halo, alkyl, Ar or Het; in particular hydrogen, halo, $C_{1-4}$alkyl, phenyl, furanyl or piperidinyl; preferably $R^1$ is halo or Het, in particular bromo or furanyl;

p=1;

$R^2$ is alkyloxy, alkylthio or a radical of formula

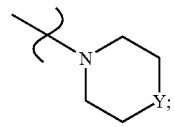

preferably alkyloxy or alkylthio, in particular $C_{1-4}$alkyloxy or $C_{1-4}$alkylthio;

$R^3$ is alkyl, Ar, Het, Ar-alkyl or Het-alkyl; in particular $C_{1-4}$alkyl, naphthyl, phenyl optionally substituted with alkyl or alkyloxy, pyridinyl, benzo[1,3]dioxolyl, —$CH_2$—$(CH_2)_n$—$R^{3a}$ wherein $R^{3a}$ is cyclohexyl, phenyl, naphthyl or furanyl, $R^{3a}$ optionally being substituted with alkyl, and wherein n is 0 or 1;

q=1, 2 or 3; in particular 1 or 2;

$R^4$ and $R^5$ each independently are hydrogen, alkyl or benzyl, in particular hydrogen or $C_{1-4}$alkyl; or $R^4$ and $R^5$ together and including the N to which they are attached form a radical selected from the group of pyrrolidinyl, piperidinyl, piperazinyl or morpholinyl, optionally substituted with alkyl or mono- or di(alkyl)amino;

$R^6$ is hydrogen, halo, alkyloxy, alkyl or phenyl optionally substituted with alkyloxy; preferably hydrogen or halo; more preferably hydrogen;

r is equal to 1 or 2; in particular 1;

$R^7$ is hydrogen.

An eighteenth interesting embodiment is the use of a compound of formula (Ia) or (Ib) or any subgroup thereof as mentioned hereinbefore as interesting embodiment for the manufacture of a medicament for the treatment of an infection with a gram-positive and/or a gram-negative bacterium.

A nineteenth interesting embodiment is the use of a compound of formula (Ia) or (Ib) or any subgroup thereof as mentioned hereinbefore as interesting embodiment for the manufacture of a medicament for the treatment of an infection with a gram-positive bacterium.

A twentieth interesting embodiment is the use of the compounds of formula (Ia) or (Ib) or any subgroup thereof as mentioned hereinbefore as interesting embodiment for the manufacture of a medicament for the treatment of an infection with a gram-negative bacterium.

A twenty first interesting embodiment is the use of a compound of formula (Ia) or (Ib) or any subgroup thereof as mentioned hereinbefore as interesting embodiment for the manufacture of a medicament for the treatment of a bacterial infection wherein the compound of formula (Ia) or (Ib) has a $IC_{90}<15$ μl/ml against at least one bacterium, in particular a gram-positive bacterium, preferably a $IC_{90}<10$ μl/ml, more preferably a $IC_{90}<5$ μl/ml; the $IC_{90}$ value being determined as described hereinafter.

Preferably, in the compounds of formula (Ia) and (Ib) or any subgroup thereof as mentioned hereinbefore as interesting embodiment, the term "alkyl" represents $C_{1-6}$alkyl, more preferably $C_{1-4}$alkyl.

Preferred compounds are selected from the following:
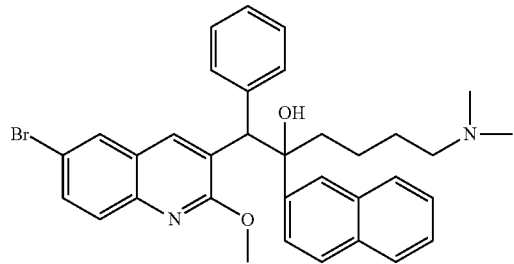
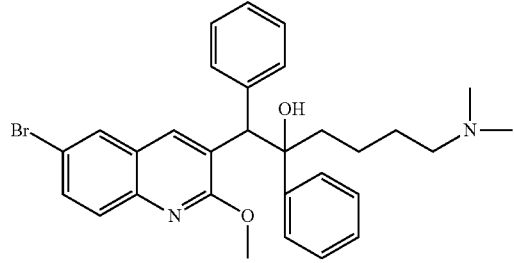
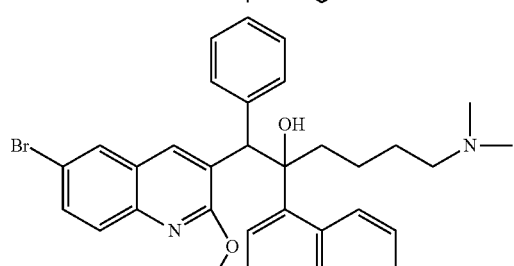
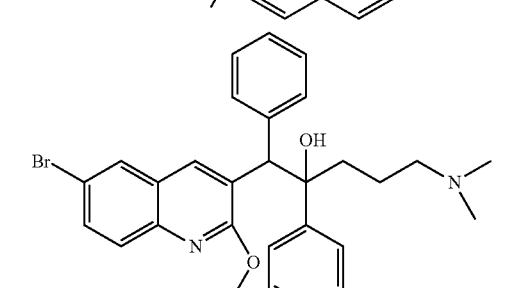
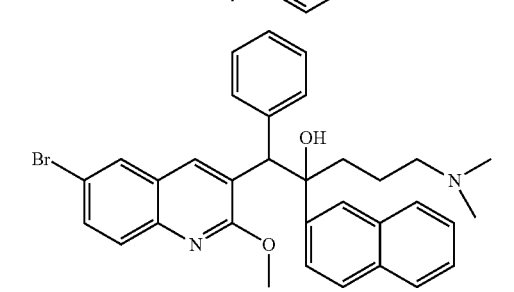
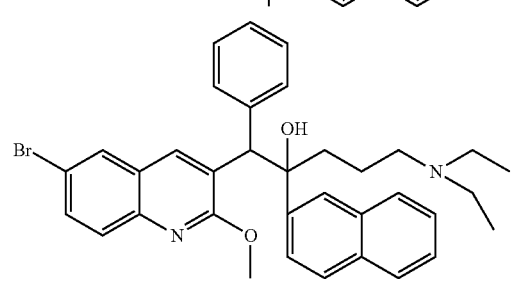
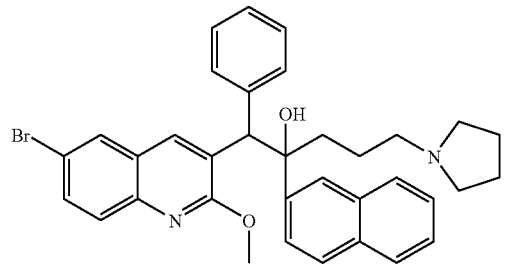
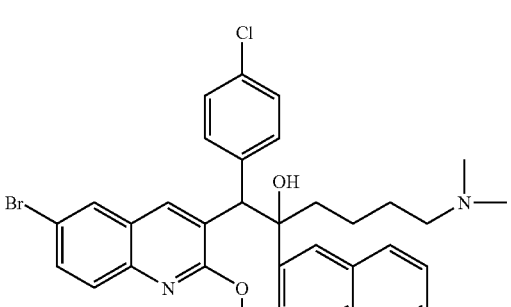
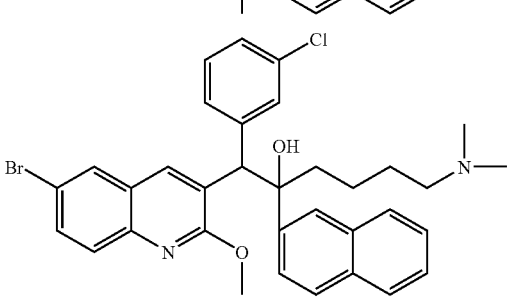
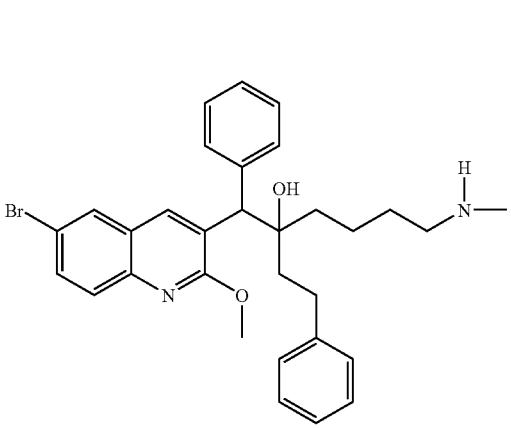
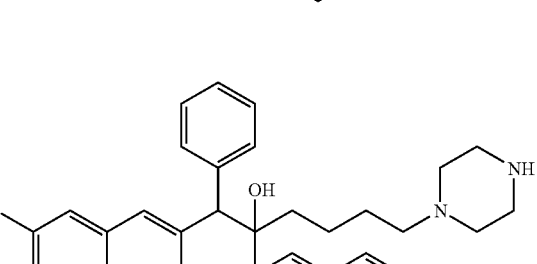

a pharmaceutically acceptable acid or base addition salt thereof, a stereochemically isomeric form thereof, a tautomeric form thereof or a N-oxide form thereof.

Especially preferred compounds are compound 17, 24, 25, 23, 20, 22, 18, 21, 19, 44, 50, 48, 47, 51, 163, 164, 70, 107, 103, 53, 159, 75, 74, 173, 158, 72, 82 and 83, especially compounds 163, 164, 70, 107, 103, 53, 159, 75, 74, 173, 158, 72, 82 and 83, (see the Tables hereinbelow), a pharmaceutically acceptable acid or base addition salt thereof, a stereochemically isomeric form thereof, a tautomeric form thereof or a N-oxide form thereof.

The present invention also relates to any one compound out of Tables 1 to 8 hereinbelow.

The present invention also relates to a compound selected from:

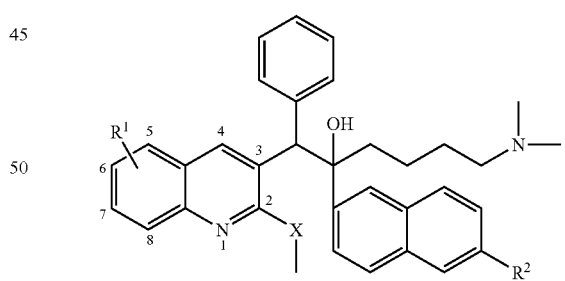

| R¹ | R² | X | Physical data and stereochemistry |
|---|---|---|---|
| H | OCH₃ | O | (B) |
| 6-Br | H | O | (A1) |
| 6-Br | H | O | (A2) |
| 6-Br | H | O | (B2) |
| 6-Br | H | S | (B) |
| 6-Br | OCH₃ | O | (A) |
| 6-Br | OCH₃ | O | (B) |
| 5-Br | OCH₃ | O | (B) |
| 7-Br | OCH₃ | O | (B) |
| 6-Br | Br | O | (A) |
| H | OCH₃ | O | (A) |

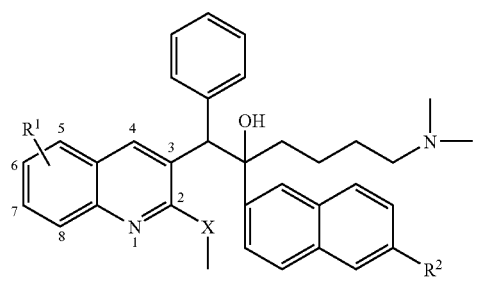

| R[1] | R[2] | X | Physical data and stereochemistry |
|---|---|---|---|
| 6-[2-furanyl] | H | O | (A) |
| 6-[2-furanyl] | H | O | (B) |
| 6-Br | Br | O | (B) |
| 6-Br | H | O | (B1) |
| 6-phenyl | H | O | (A) |
| 6-phenyl | H | O | (B) |
| 5-Br | OCH$_3$ | O | (A) |
| 6-Br | H | S | (A) |
| 7-Br | OCH$_3$ | O | (A) |
| H | H | O | (A) |
| H | H | O | (B) |
| 7-Br | H | O | (B) |
| 7-Br | H | O | (A) |
| 5-Br | H | O | (A) |
| 5-Br | H | O | (B) |

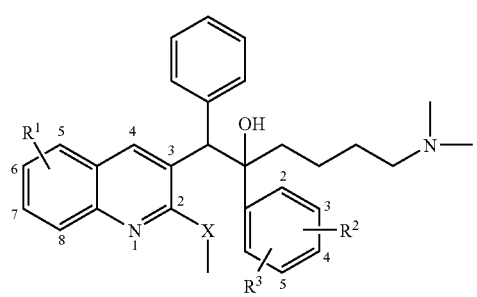

| R[1] | R[2] | R[3] | X | Physical data salt/melting points and stereochemistry |
|---|---|---|---|---|
| 6-Br | H | H | S | (B) |
| 6-Br | H | H | S | (A) |
| 6-[3-pyridinyl] | H | H | O | (A) |
| 6-[3-pyridinyl] | H | H | O | (B) |
| 6-Br | 3-F | 5-F | O | (A) |
| 6-Br | 3-F | 5-F | O | (B) |
| 6-Br | 2-F | 5-F | O | (B) |
| 6-Br | 2-F | 5-F | O | (A) |

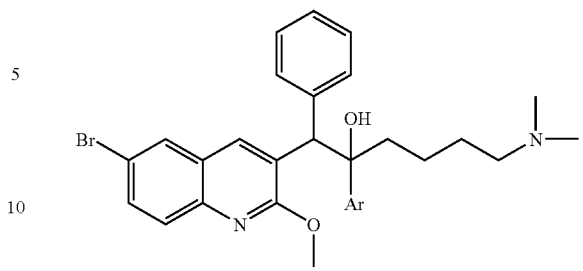

| Ar | Physical data salt/melting points and stereochemistry |
|---|---|
| 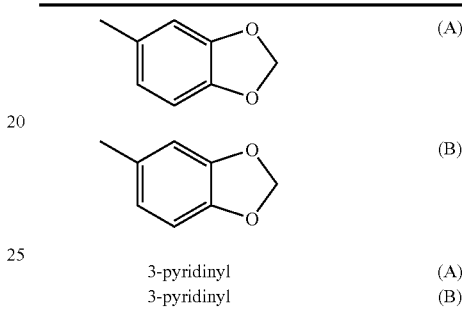 | (A) |
| | (B) |
| 3-pyridinyl | (A) |
| 3-pyridinyl | (B) | a pharmaceutically acceptable acid or base addition salt thereof, a stereochemically isomeric form thereof, a tautomeric form thereof or a N-oxide form thereof.

Especially, the present invention also relates to a compound selected from

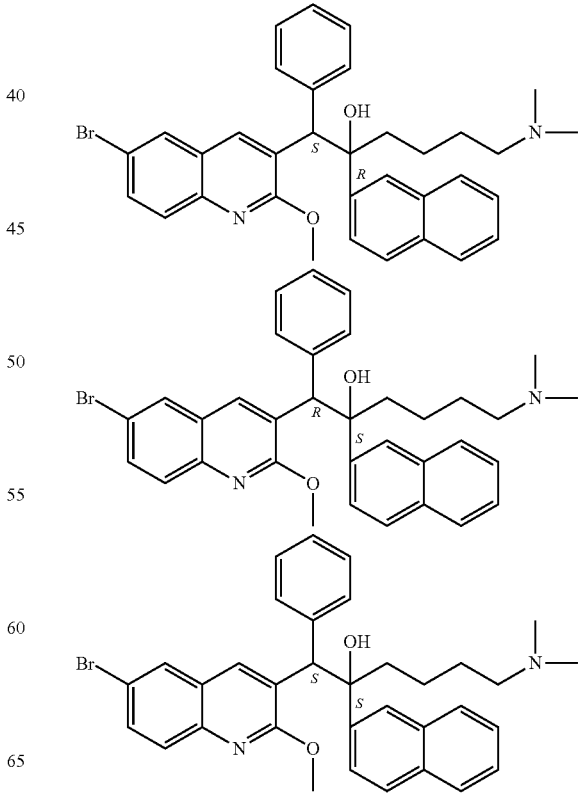

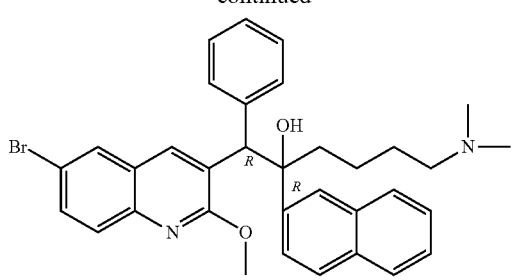
a pharmaceutically acceptable acid or base addition salt thereof, a tautomeric form thereof or a N-oxide form thereof.
The present invention also relates to a compound selected from
(dia B)
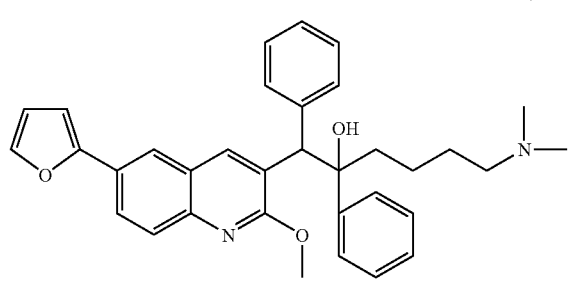
(B2)
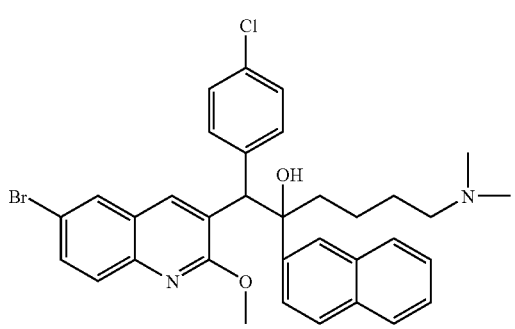
(B1)
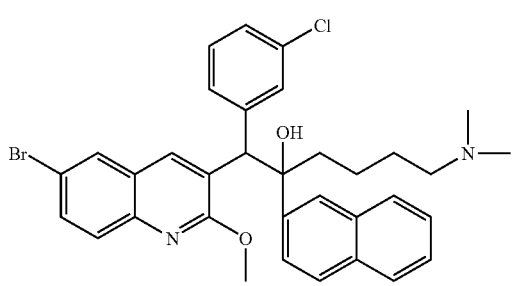
(dia A)
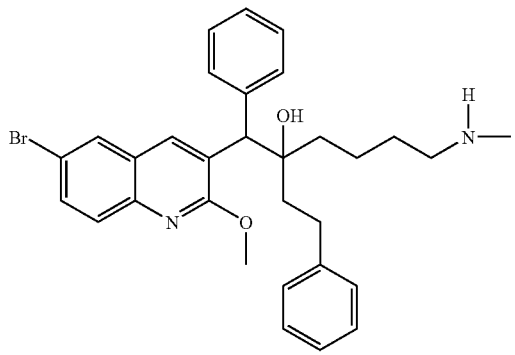
(dia b)
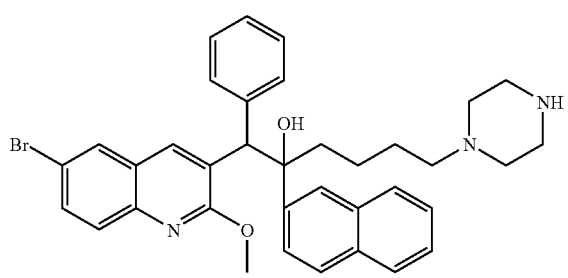
(B1)
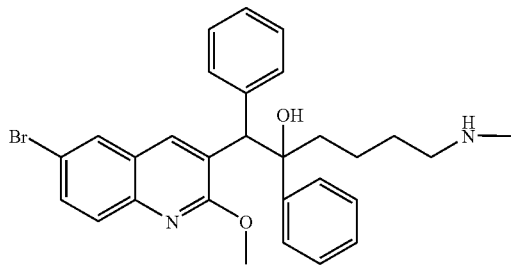
(dia B)
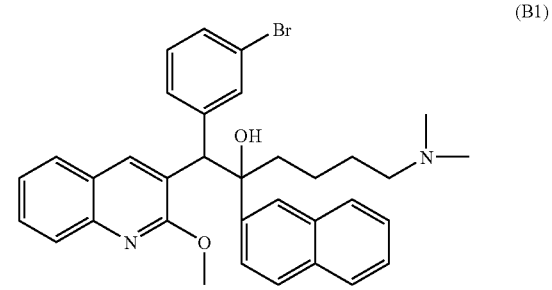
(B1)

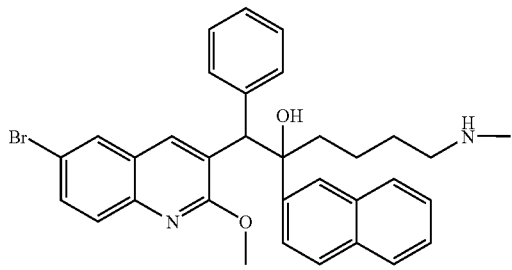
(dia B)

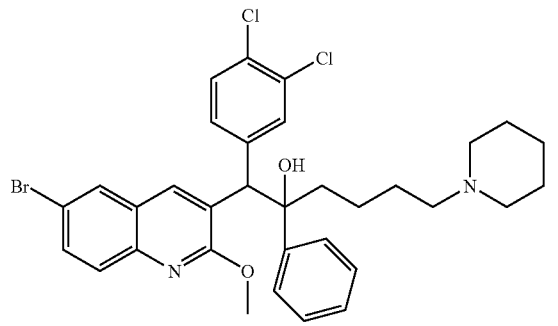
(B2)

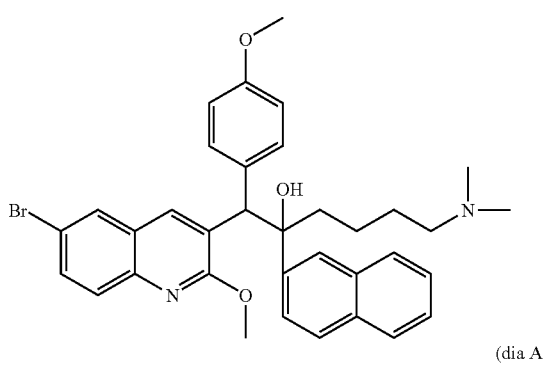
(dia A)

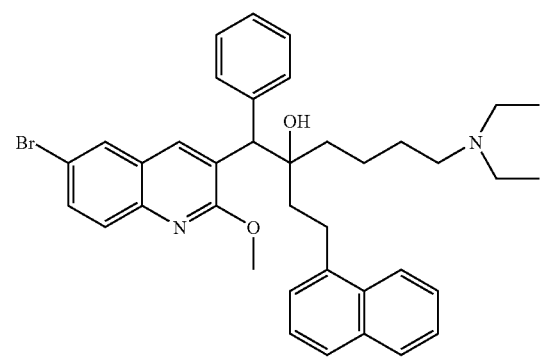
(dia A)

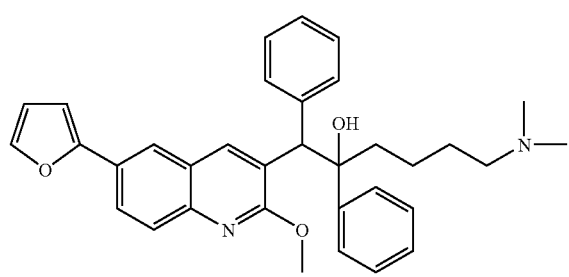

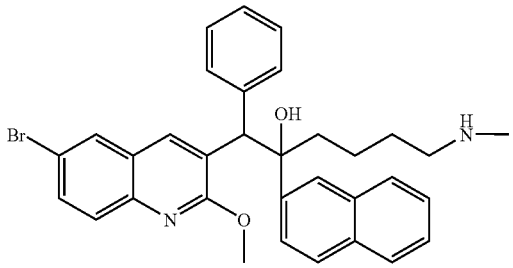
(dia A)

a pharmaceutically acceptable acid or base addition salt thereof, a tautomeric form thereof or a N-oxide form thereof.

Preferably, the compound of formula (Ia) or (Ib) is a particular diastereoisomer (substantially free of the other diastereoisomer(s)). In case the compound of formula (Ia) or (Ib) has two chiral centers this means that the compound is a racemic mixture of the (R,S) and (S,R) enantiomers or a racemic mixture of the (R,R) and (S,S) enantiomer. Hereinafter, the racemic mixtures of 2 enantiomers are indicated as diastereoisomer A or B. Whether the racemic mixture is indicated as A or B depends on whether it is first isolated in the synthesis protocol (i.e. A) or second (i.e. B). More preferably, the compound of formula (Ia) or (Ib) is a particular enantiomer (substantially free of the other enantiomers). In case the compound of formula (Ia) or (Ib) has two chiral centers this means that the compound is the (R,S), (S,R), (R,R) or (S,S) enantiomer. Hereinafter, said particular enantiomers are indicated as A1, A2, B1 or B2. Whether the enantiomer is indicated as A1, A2, B1 or B2 depends on whether it is isolated first or second in the synthesis protocol.

The compounds of formula (Ia) or (Ib) can be prepared according to the methods described in WO 2004/011436, which is incorporated herein by reference.

In general, the compounds according to the invention can be prepared by a succession of steps, each of which is known to the skilled person.

In particular, the compounds according to formula (Ia) can be prepared by reacting an intermediate compound of formula (II) with an intermediate compound of formula (III) according to the following reaction scheme (1a):

Scheme 1a

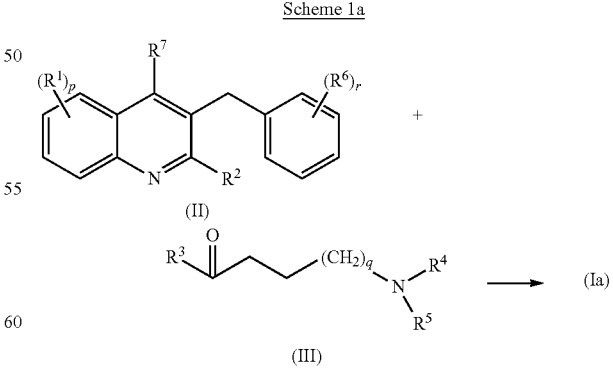

using n-BuLi in the presence of a suitable solvent, such as for example tetrahydrofuran, and a suitable base, such as for example diisopropyl amine, wherein all variables are defined as in formula (Ia). Stirring may enhance the rate of the reaction. The reaction may conveniently be carried out at a temperature ranging between −20 and −70° C.

The same reaction procedure can be used to synthesize intermediates of formula (I-b).

Compounds of formula (Ia) can also be prepared according to the following reaction scheme 1b:

Compounds of formula (Ia) can also be prepared according to the following reaction scheme 1c:

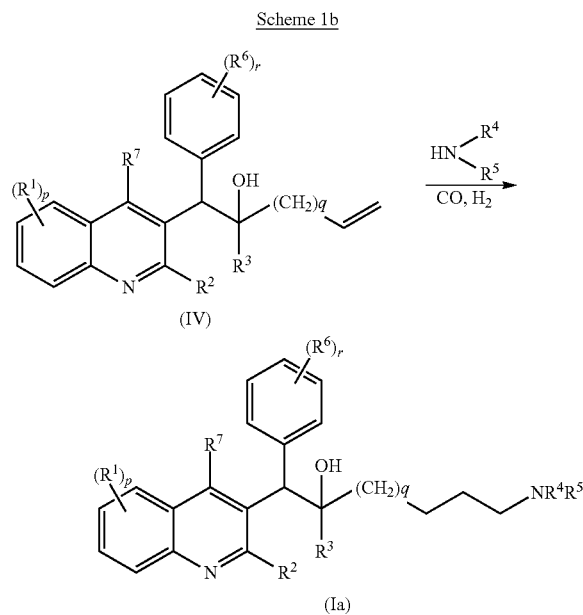

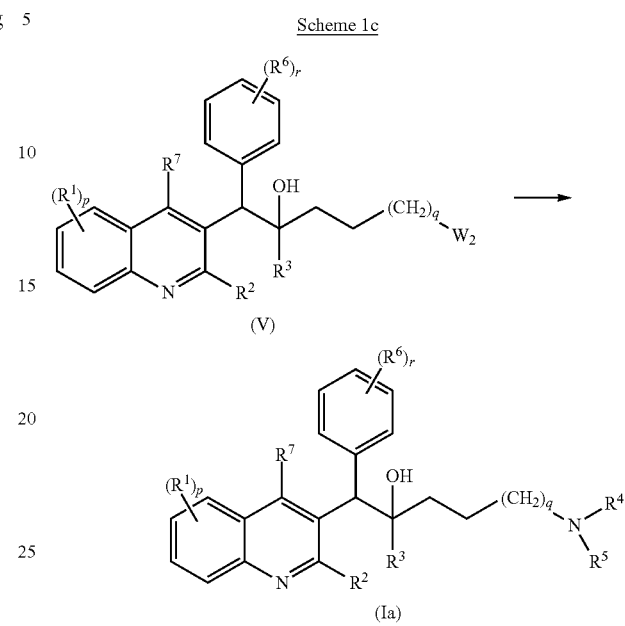

wherein all variables are as defined hereinabove. In scheme 1b, an intermediate of formula (IV) wherein q is 0, 1 or 2, is reacted with a primary or secondary amine $HNR^4R^5$ in the presence of a suitable catalyst, such as for example $Rh(cod)_2BF_4$, optionally in the presence of a second catalyst (for the reduction), such as for example $Ir(cod)_2BF_4$, in the presence of a suitable ligand, such as for example Xantphos, in a suitable solvent, such as for example tetrahydrofuran and an alcohol e.g. methanol in the presence of CO and $H_2$ (under pressure) at elevated temperature. This reaction is preferably done for intermediates of formula (IV) wherein q is 1.

wherein all variables are as defined hereinabove. In scheme 1c, an intermediate of formula (V) wherein $W_2$ represents a suitable leaving group, such as for example halo, e.g. chloro or bromo, is reacted with a suitable primary or secondary amine $HNR^4R^5$.

The same reaction procedure can be used to synthesize intermediates of formula (I-b).

The starting materials and the intermediate compounds of formula (II) and (III) are compounds that are either commercially available or may be prepared according to conventional reaction procedures generally known in the art. For example, intermediate compounds of formula (II-a) to (II-d) may be prepared according to the following reaction scheme (2):

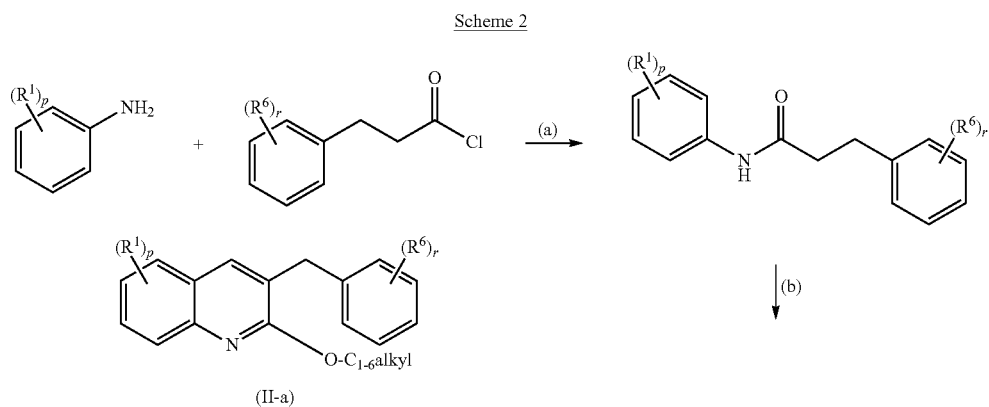

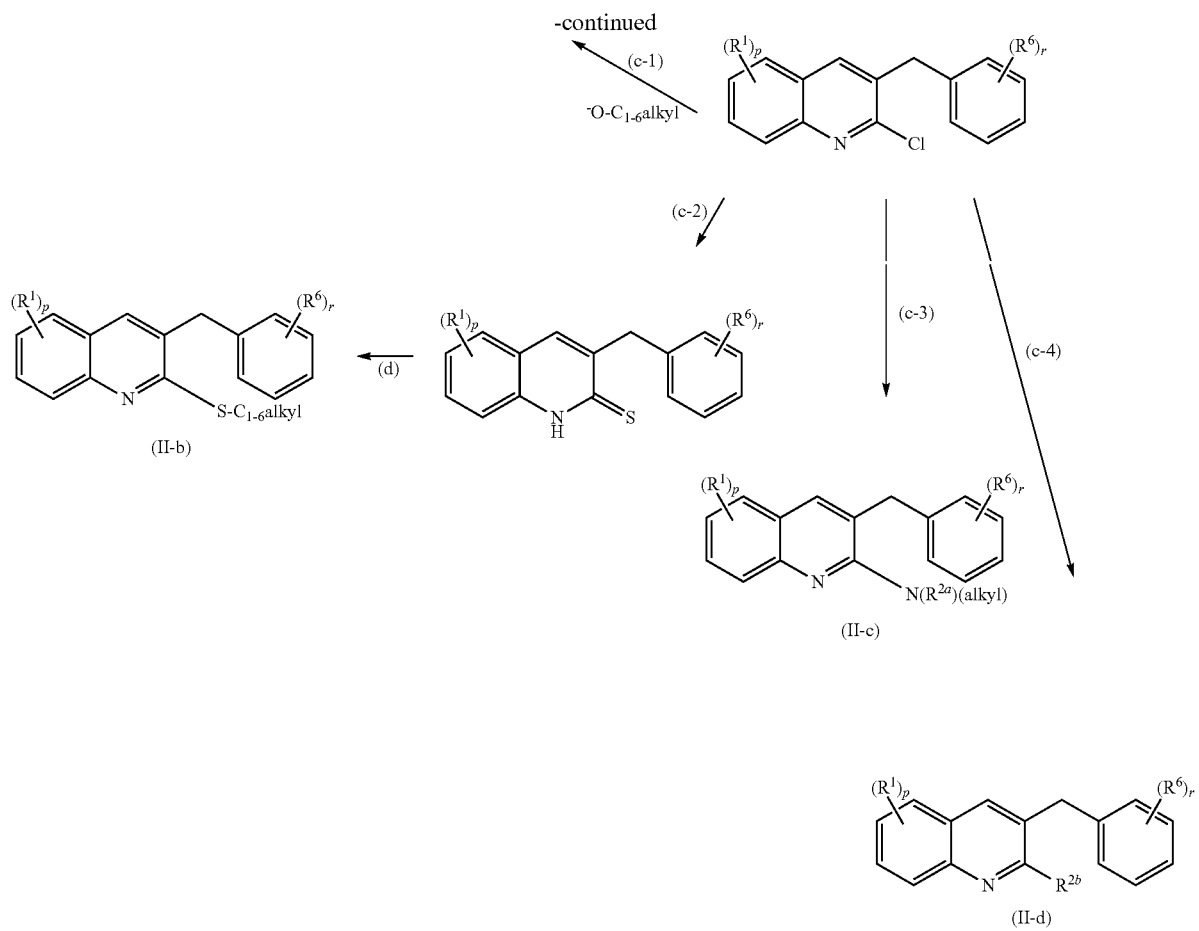

wherein all variables are defined as in formula (Ia). Reaction scheme (2) comprises step (a) in which an appropriately substituted aniline is reacted with an appropriate acylchloride such as 3-phenylpropionyl chloride, 3-fluorobenzenepropionyl chloride or p-chlorobenzenepropionyl chloride, in the presence of a suitable base, such as triethylamine and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride ($POCl_3$) in the presence of N,N-dimethylformamide (Vilsmeier-Haack formylation followed by cyclization). The reaction may conveniently be carried out at a temperature ranging between room temperature and reflux temperature. In a next step (c-1), a specific $R^2$-group, wherein $R^2$ is for example a $C_{1-6}$alkyloxy radical is introduced by reacting the intermediate compound obtained in step (b) with $^-O—C_{1-6}$alkyl in the presence of a suitable solvent, such as for example $HO—C_{1-6}$alkyl. The intermediate compound obtained in step (b) can also be converted into an intermediate compound wherein $R^2$ is for example a $C_{1-6}$alkylthio radical by reaction with $S=C(NH_2)_2$ in the presence of a suitable solvent, such as for example an alcohol, e.g. ethanol (step (c-2)) followed by reaction with $C_{1-6}$alkyl-I in the presence of a suitable base, such as for example $K_2CO_3$ and a suitable solvent, such as for example 2-propanone. The intermediate compound obtained in step (b) can also be converted into an intermediate compound wherein $R^2$ is $N(R^{2a})$(alkyl) wherein $R^{2a}$ is hydrogen or alkyl, by reaction with a suitable salt of $NH(R^{2a})$(alkyl) in the presence of a suitable base, such as for example potassium carbonate, and a suitable solvent, such as for example acetonitrile (step (c-3)). The intermediate compound obtained in step (b) can also be converted into an intermediate compound wherein $R^2$ is alkyloxyalkyloxy optionally substituted with alkyloxy, said $R^2$ being represented by $R^{2b}$, by reaction with alkyloxyalkylOH optionally substituted with alkyloxy in the presence of NaH and a suitable solvent, such as for example tetrahydrofuran (step (c-4)).

Intermediate compounds according to formula (II-e) may be prepared according to the following reaction scheme (3), wherein in a first step (a) a substituted indole-2,3-dione is reacted with a substituted 3-phenylpropionaldehyde in the presence of a suitable base such as sodium hydroxide (Pfitzinger reaction), after which the carboxylic acid compound in a next step (b) is decarboxylated at high temperature in the presence of a suitable reaction-inert solvent such as diphenylether.

Scheme 3

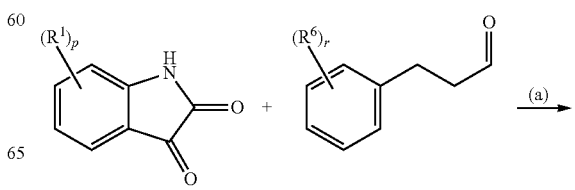

-continued

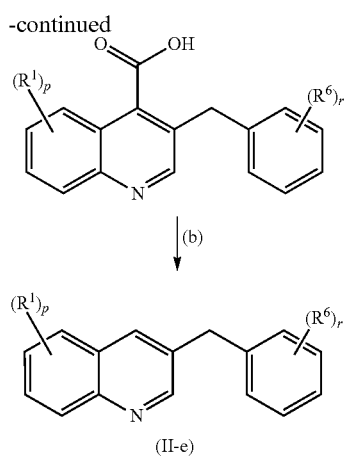

(II-e)

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SFC).

The intermediate compounds of formula (III) are compounds that are either commercially available or may be prepared according to conventional reaction procedures generally known in the art. For example, intermediate compounds of formula (III) may be prepared according to the following reaction scheme (4):

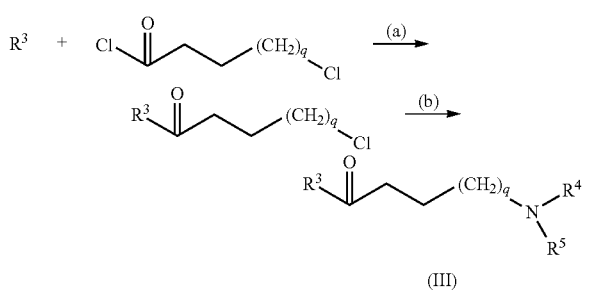

Reaction scheme (4) comprises step (a) in which $R^3$, for instance an appropriately substituted Ar, in particular an appropriately substituted phenyl or naphthyl, is reacted by Friedel-Craft reaction with an appropriate acylchloride such as 5-chlorovaleryl chloride or 4-chlorobutyryl chloride, in the presence of a suitable Lewis acid, such as for example $AlCl_3$, $FeCl_3$, $SnCl_4$, $TiCl_4$ or $ZnCl_2$ and a suitable reaction-inert solvent, such as methylene chloride or ethylene dichloride. The reaction may conveniently be carried out at a temperature ranging between room temperature and reflux temperature. In a next step (b) an amino group (—$NR_4R_5$) is introduced by reacting the intermediate compound obtained in step (a) with a primary or secondary amine $HNR_4R_5$ in the presence of a suitable solvent, such as for example acetonitrile, and a suitable base, such as for example $K_2CO_3$.

The intermediate compounds of formula (III) may also be prepared according to the following reaction Scheme (5):

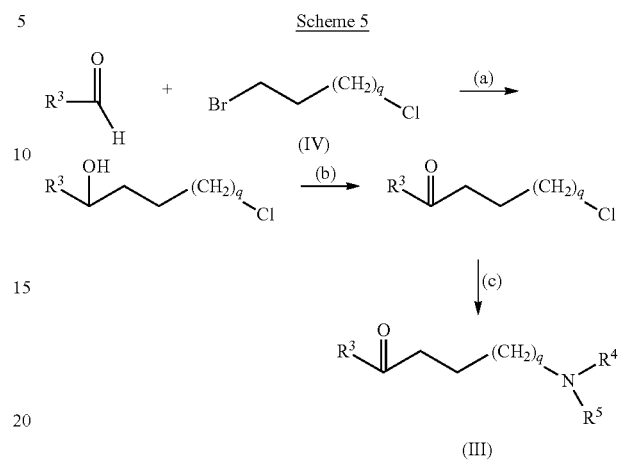

Reaction scheme (5) comprises step (a) in which $R^3$—C(=O)—H, for instance an appropriately substituted Ar carboxaldehyde, more in particular an appropriately substituted phenyl or naphthyl carboxaldehyde, is reacted with an appropriate intermediate compound of formula (IV) such as for example 1-bromo-4-chlorobutane, in the presence of Grignard reagent and a suitable solvent, such as for example diethyl ether, tetrahydrofuran. The reaction may conveniently be carried out at a low temperature for instance 5° C. In a next step (b) an oxidation is performed in the presence of Jones' reagent in a suitable solvent, such as for example acetone. In a next step (c), an amino group (—$NR_4R_5$) is introduced by reacting the intermediate compound obtained in step (b) with a primary or secondary amine $HNR_4R_5$ in the presence of a suitable solvent, such as for example acetonitrile, and a suitable base, such as for example $K_2CO_3$.

The intermediate compounds of formula (III) may also be prepared according to the following reaction Scheme (6):

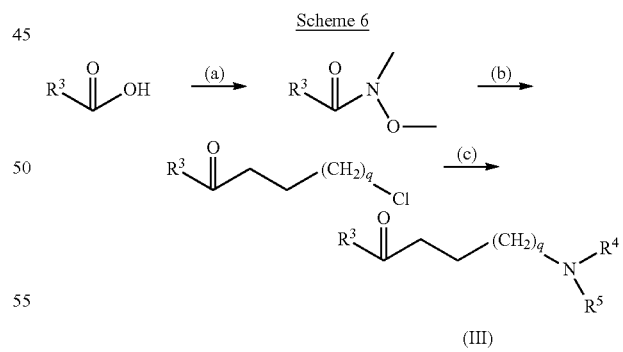

Reaction scheme (6) comprises step (a) in which for instance a suitable acid is reacted with $NH(CH_3)(OCH_3)$ in the presence of 1,1'-carbonyldiimidazole and a suitable solvent, such as for example $CH_2Cl_2$. In a next step (b), the product obtained in step (a) is reacted with a suitable Grignard reagens e.g. 4-chlorobutyl magnesium bromide in the presence of a suitable solvent, such as for example tetrahydrofuran. In a next step (c), an amino group (—$NR_4R_5$) is introduced by reacting the intermediate compound obtained in step (b) with a primary or secondary amine $HNR_4R_5$ in the presence of a suitable solvent, such as for example acetonitrile, and a suitable base, such as for example $K_2CO_3$.

Intermediates of formula (IV) may be prepared according to the following reaction scheme 7:

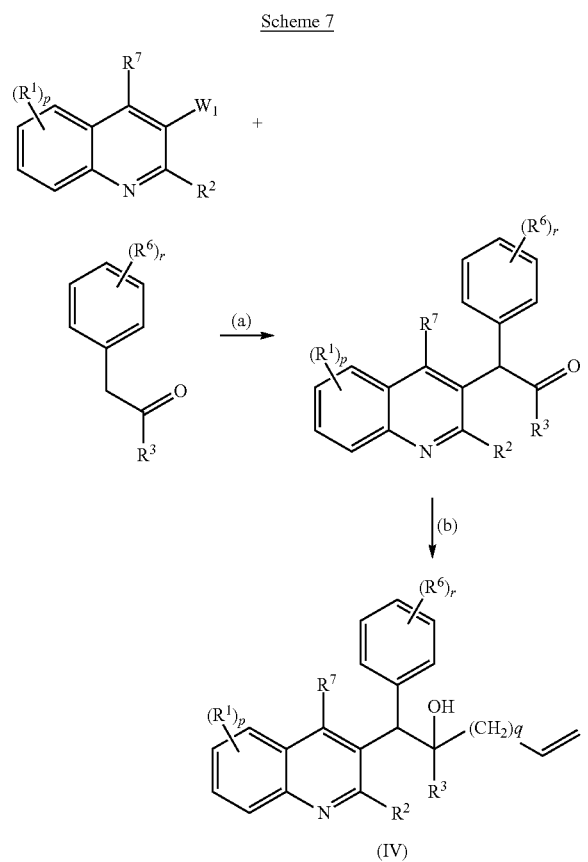

Scheme 7

Reaction scheme 7 comprises the step of reacting an appropriately substituted quinoline wherein $W_1$ represents a suitable leaving group, such as for example halo, e.g. bromo, with an appropriately substituted deoxybenzoin in the presence of a suitable catalyst, such as for example palladium diacetate, a suitable ligand, such as for example X-PHOS, a suitable base, such as for example cesium carbonate, a suitable solvent, such as for example xylene, under $N_2$ flow. In a next step (b), the product obtained in step (a) is reacted with a suitable Grignard reagens (e.g. $CH_2=CH-(CH_2)_q-Mg-Br$, such as for example allylmagnesium bromide, in a suitable solvent, such as for example tetrahydrofuran.

Intermediates of formula (V) may be prepared according to the following reaction scheme 8:

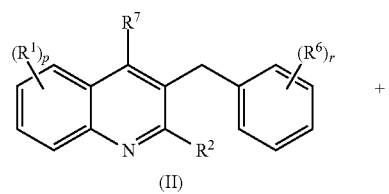

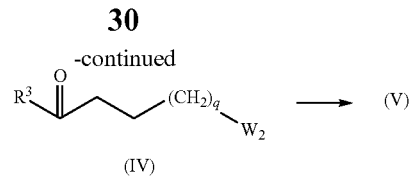

In reaction scheme 8, an intermediate of formula (II) is reacted with an intermediate of formula (VI), for its synthesis reference is made to schemes 4, 5 and 6, in the presence of n-BuLi in a suitable solvent, such as for example tetrahydrofuran, and a suitable base, such as for example diisopropyl amine. Stirring may enhance the rate of the reaction. The reaction may conveniently be carried out at a temperature ranging between −20 and −70° C.

The present invention also relates to a compound of formula (V)

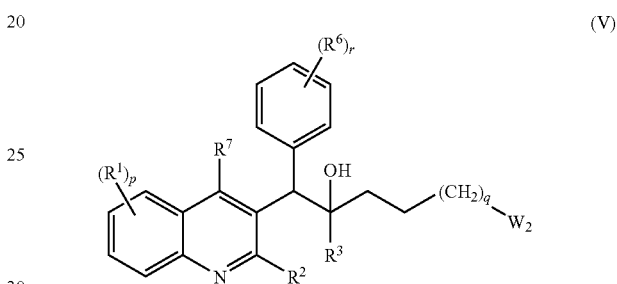

wherein $W_2$ represents a suitable leaving group, such as for example halo, e.g. bromo or chloro, and $R^1$, $R^2$, $R^3$, $R^6$, $R^7$, q, p and r are as defined for the compounds of formula (Ia).

Alternatively, the present invention also relates to a compound of formula (VII)

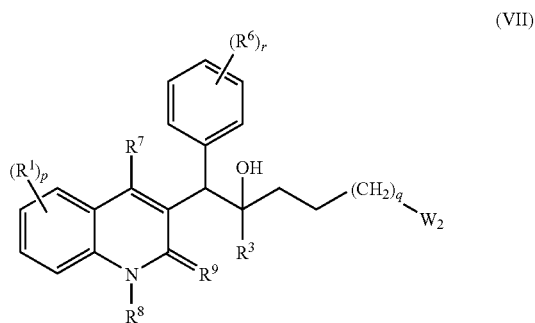

wherein $W_2$ represents a suitable leaving group, such as for example halo, e.g. bromo or chloro, and $R^1$, $R^3$, $R^6$, $R^7$, $R^8$, $R^9$, q, p and r are as defined for the compounds of formula (Ib).

The compounds of formula (Ia) or (Ib) can also be converted into each other following art-known functional group transformation reactions, comprising those described hereinafter.

For instance, compounds of formula (Ia) or (Ib) wherein $R^1$ is halo, in particular bromo, can be converted into a compound of formula (Ia) or (Ib) wherein $R^1$ is hydrogen, by reaction with $HCOONH_4$ in the presence of a suitable catalyst such as for example palladium on charcoal, and in the presence of a suitable solvent, such as for example an alcohol, e.g. methanol.

Compounds of formula (Ia) or (Ib) wherein R¹ or R⁶ represents halo, in particular bromo, can be converted into a compound of formula (Ia) or (Ib) wherein R¹ or R⁶ represents Ar or Het, by reaction with Ar—B(OH)₂ respectively Het-B(OH)₂ in the presence of Pd(PPh₃)₄ or Pd(PPh₃)₄Cl₂, a suitable base, such as for example K₂CO₃ or Na₂CO₃, and a suitable solvent, such as for example 1,2-dimethoxyethane or an alcohol, e.g. methanol.

Compounds of formula (Ia) or (Ib) wherein R¹ represents halo, in particular bromo, can also be converted into a compound of formula (Ia) or (Ib) wherein R¹ represents Het, by reaction with

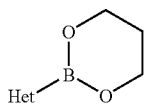

in the presence of Pd(PPh₃)₄, a suitable base, such as for example K₂CO₃, and a suitable solvent, such as for example 1,2-dimethoxyethane or an alcohol, e.g. methanol.

Compounds of formula (Ia) or (Ib) wherein R¹ is halo, in particular bromo, can also be converted into an intermediate wherein R¹ is formyl by reaction with N,N-dimethylformamide in the presence of n-BuLi and a suitable solvent, such as for example tetrahydrofuran. These intermediates can then be converted into a compound of formula (Ia) or (Ib) wherein R¹ is —CH₂—OH by reaction with a suitable reducing agent, such as for example NaBH₄ and in the presence of a suitable solvent, such as for example an alcohol, e.g. methanol, and tetrahydrofuran.

Compounds of formula (Ia) or (Ib) wherein R⁴ is benzyl can be converted into a compound of formula (Ia) or (Ib) wherein R⁴ is hydrogen, by reaction with 1-chloroethyl chloroformate in a suitable solvent, such as for example 1,2-dichloroethane.

In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogens*; Bacilli, for example *Bacillus subtilis*; *Listeria*, for example *Listeria monocytogenes*; *Haemophilus*, for example *H. influenza*; *Moraxella*, for example *M. catarrhalis*; *Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Streptococcus pneumoniae* and/or *Staphylococcus aureus*, including resistant *Staphylococcus aureus* such as for example methicillin resistant *Staphylococcus aureus* (MRSA), especially against *Staphylococcus aureus*, including resistant *Staphylococcus aureus*. The present compounds have especially a good activity against SPN 6305 (*Streptococcus pneumoniae* (ATCC6305)) and/or STA 29213 (*Staphylococcus aureus* (ATCC29213)).

In particular, the compounds of the present invention are active on those bacteria of which the viability depends on proper functioning of F1F0 ATP synthase. Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria Whenever used hereinbefore or hereinafter, that the compounds can treat a bacterial infection it is meant that the compounds can treat an infection with one or more bacterial strains.

Whenever used hereinbefore or hereinafter, that the bacterial infection is other than a Mycobacterial infection it is meant that the bacterial infection is other than an infection with one or more *Mycobacteria* strains.

The exact dosage and frequency of administration of the present compounds depends on the particular compound of formula (Ia) or (Ib) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compound of the present invention may be administered in a pharmaceutically acceptable form optionally in a pharmaceutically acceptable carrier. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antibacterial to be administered, as well as the duration of treatment, may be adjusted as needed.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Given the fact that the compounds of formula (Ia) or (Ib) are active against bacterial infections, the present compounds may be combined with other antibacterial agents in order to effectively combat bacterial infections.

Therefore, the present invention also relates to a combination of (a) a compound of formula (Ia) or (Ib), and (b) one or more other antibacterial agents provided that the one or more other antibacterial agents are other than antimycobacterial agents.

The present invention also relates to a combination of (a) a compound of formula (Ia) or (Ib), and (b) one or more other antibacterial agents provided that the one or more other antibacterial agents are other than antimycobacterial agents, for use as a medicine.

A pharmaceutical composition comprising a pharmaceutically acceptable carrier and, as active ingredient, a therapeutically effective amount of (a) a compound of formula (Ia) or (Ib), and (b) one or more other antibacterial agents provided that the one or more other antibacterial agents are other than antimycobacterial agents, is also comprised by the present invention.

The present invention also relates to the use of a combination or pharmaceutical composition as defined above for the treatment of a bacterial infection.

The present pharmaceutical composition may have various pharmaceutical forms for administration purposes. As appropriate compositions there may be cited all compositions usually employed for systemically administering drugs. To prepare the pharmaceutical compositions of this invention, an effective amount of the particular compounds, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral unit dosage forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredients, and, from 1 to 99.95% by weight, more preferably from 30 to 99.9 weight % of a pharmaceutically acceptable carrier, all percentages being based on the total composition.

The weight to weight ratio's of the compound of formula (Ia) or (Ib) and (b) the other antibacterial agent(s) when given as a combination may be determined by the person skilled in the art. Said ratio and the exact dosage and frequency of administration depends on the particular compound of formula (Ia) or (Ib) and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compounds of formula (Ia) or (Ib) and the one or more other antibacterial agents may be combined in a single preparation or they may be formulated in separate preparations so that they can be administered simultaneously, separately or sequentially. Thus, the present invention also relates to a product containing (a) a compound of formula (Ia) or (Ib), and (b) one or more other antibacterial agents provided that the one or more other antibacterial agents are other than antimycobacterial agents, as a combined preparation for simultaneous, separate or sequential use in the treatment of a bacterial infection.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the bacterial disease indicated.

The other antibacterial agents which may be combined with the compounds of formula (I) are antibacterial agents known in the art. The other antibacterial agents comprise antibiotics of the α-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (Ia) or (Ib) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrronitrin, fosfomycin, fusidic acid, bicozamycin, tiamulin, siccanin.

EXPERIMENTAL PART

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction.

In case "A" and "B" are stereoisomeric mixtures, they can be further separated whereby the respective first fractions isolated are designated "A1" respectively "B1" and the second as "A2" respectively "B2", without further reference to the actual stereochemical configuration. However, said "A1", "A2" and "B1", "B2" isomeric forms can be unambiguously characterized by a person skilled in the art, using art-known methods such as, for example, X-ray diffraction.

Hereinafter, "THF" is defined as tetrahydrofuran, "DIPE" is defined as diisopropyl ether, "DME" is defined as 1,2-dimethoxyethane, "DMF" is defined as N,N-dimethylformamide, "CDI" is defined as 1,1'-carbonylbis-1H-imidazole.

A. Preparation of the Intermediate Compounds

Example A1A a) Preparation of Intermediate 1

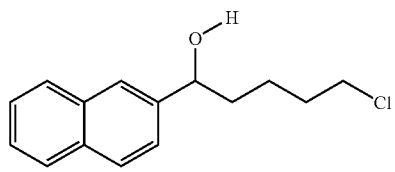 [SMILES: OC(CCCCCl)c1ccc2ccccc2c1]

To a stirred solution of Grignard reagent at 5° C., prepared from Mg turnings (0.14 mol) and 1-bromo-4-chlorobutane (0.14 mol) in diethylether (150 ml), was added dropwise a solution of 2-naphthylcarboxaldehyde (0.0935 mol) in THF (150 ml). After the mixture was stirred for 4 hours at 5° C. a solution of ammonium chloride (10% aqueous) was added slowly. The organic layer was separated, washed with brine, dried over magnesium sulfate, filtered, and the solvent was evaporated. The residue was purified by column chromatography over silica gel (eluent: cyclohexane/EtOAc:90/10; 15-40 µm). The pure fractions were collected and the solvent was evaporated. Yield: 8.2 g of intermediate 1 (35%).

b) Preparation of Intermediate 2

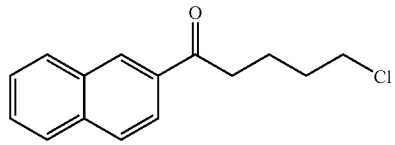 [SMILES: O=C(CCCCCl)c1ccc2ccccc2c1]

Jones' reagent (0.024 mol), prepared by dissolving 40 g of $CrO_3$ in 80 ml of water and 20 ml of concentrated sulfuric acid, was added drop wise to a cooled solution of intermediate 1 (0.061 mol) in acetone (120 ml). After the addition, the reaction mixture was stirred for 1 hour at 0° C. Water was added and the mixture was extracted with diethylether. The organic layer was separated, washed with brine, dried over magnesium sulfate, filtered, and the solvent was evaporated. Yield: 3.8 g of intermediate 2 (96%).

c) Preparation of Intermediate 3a

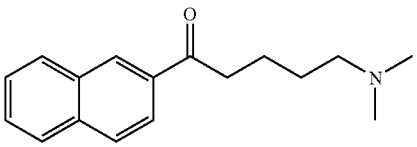 [SMILES: CN(C)CCCCC(=O)c1ccc2ccccc2c1]

A mixture of intermediate 2 (0.0308 mol), dimethylamine hydrochloride (0.123 mol) and potassium carbonate (0.154 mol) in acetonitrile (150 ml) was stirred under reflux overnight then cooled to room temperature, poured out into water and extracted with diethyl ether. The organic layer was extracted with HCl 1N, basified with NaOH 3N and extracted with diethyl ether, washed with brine, dried over magnesium sulfate, filtered, and the solvent was evaporated. Yield: 4.2 g of intermediate 3a (53%).

d) Preparation of Intermediate 3b

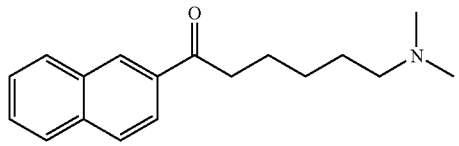 [SMILES: CN(C)CCCCCC(=O)c1ccc2ccccc2c1]

Intermediate 3b was prepared in 3 steps according to the same protocol as intermediate 3a, but starting from 1-bromo-5-chloropentane and 2-naphthylcarboxaldehyde.

e) Preparation of Intermediate 3c

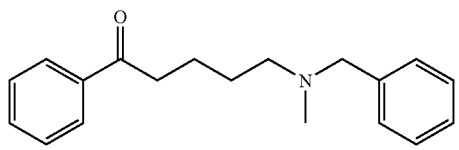 [SMILES: CN(CCCCC(=O)c1ccccc1)Cc1ccccc1]

A mixture of intermediate 2b (0.0153 mol) (see Example A1B), N-methyl-benzylamine (0.0168 mol) and potassium carbonate (0.0229 mol) in acetonitrile (30 ml) was stirred under reflux for 72 hours then cooled to room temperature, poured out into water and extracted with EtOAc. The organic layer was extracted with HCl 1N. The resulting aqueous layer was basified with NaOH 3N and extracted with diethyl ether. The organic layer was separated, washed with brine, dried over magnesium sulfate, filtered and the solvent was evaporated. Yield: 2.9 g of intermediate 3c (68%).

f) Preparation of Intermediate 3d

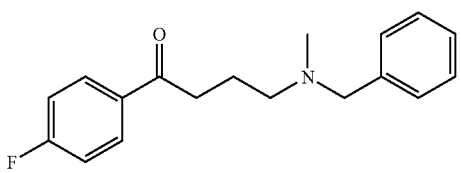 [SMILES: CN(CCCC(=O)c1ccc(F)cc1)Cc1ccccc1]

Intermediate 3d was prepared according to the same protocol as intermediate 3c.
Yield: 4.73 g (55%).

g) Preparation of Intermediate 3e

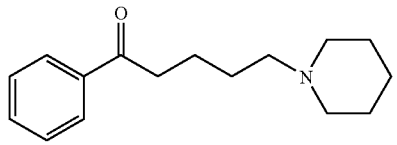 [SMILES: O=C(CCCCN1CCCCC1)c1ccccc1]

Intermediate 3e was prepared according to the same protocol as intermediate 3c. Yield: 1.2 g of intermediate 3e (96%).

Example A1B

Preparation of Intermediate 2a

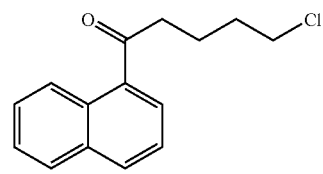 [SMILES: O=C(CCCCCl)c1cccc2ccccc12]

A solution of naphtalene (0.156 mol) in CH$_2$Cl$_2$ (100 ml) was added drop wise to a mixture of 5-chlorovalerylchloride (0.156 mol) and aluminum chloride (0.172 mol) in CH$_2$Cl$_2$ (100 ml) at 0° C. The mixture was stirred for 2 hours at room temperature, then poured into ice/water and extracted with CH$_2$Cl$_2$. The organic layer was separated, washed with K$_2$CO$_3$ 10%, dried over magnesium sulfate, filtered, and the solvent was evaporated. The residue was purified by column chromatography over silica gel (eluent: CH$_2$Cl$_2$/Cyclohexane: 40/60; 20-45 µm). The pure fractions were collected and the solvent was evaporated. Yield: 20 g of intermediate 2a (52%).

Intermediate 2b

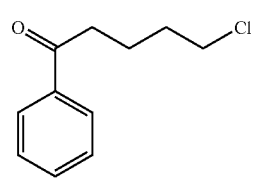 [SMILES: O=C(CCCCCl)c1ccccc1]

was prepared according to the same protocol, but starting from benzene.

Intermediate 2a and 2b can be converted into an amino derivative (N(CH$_3$)$_2$) according to the protocol described in A1c.

Example A2 a) Preparation of Intermediate 4

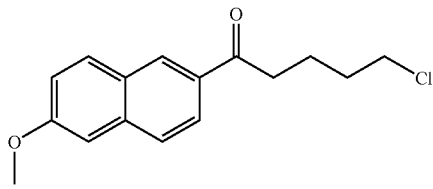 [SMILES: COc1ccc2cc(C(=O)CCCCCl)ccc2c1]

A solution of 2-methoxynaphtalene (0.19 mol) in CH$_2$Cl$_2$ (100 ml) was added dropwise to a mixture of 5-chlorovaleryl-chloride (0.19 mol) and aluminum chloride (0.208 mol) in CH$_2$Cl$_2$ (200 ml) at 0° C. The mixture was stirred for 2 hours at 0° C. then poured into ice/water and extracted with CH$_2$Cl$_2$. The organic layer was separated, washed with K$_2$CO$_3$ 10%, dried over magnesium sulfate, filtered, and the solvent was evaporated. The residue was taken up in diisopropylether, filtered and dried under vacuum. Yield: 27.9 g of intermediate 4 (59%).

b) Preparation of Intermediate 5

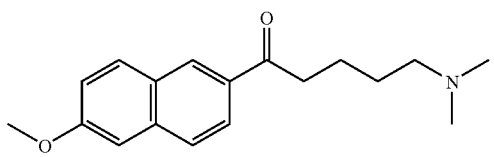

Intermediate 5 was prepared according to the same protocol as intermediate 3a, but starting from intermediate 4.

Example A3 a) Preparation of Intermediate 6

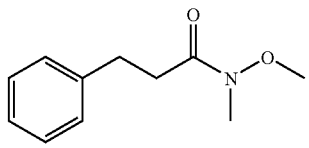

To a solution of benzene propanoic acid (20 g, 0.13 mol) in CH$_2$Cl$_2$ (200 ml), CDI (32.4 g, 0.26 mol, 2 equiv) was added at 5° C. The mixture was stirred at 5° C. for 1 hour. N,O-dimethyl-hydroxylamine (hydrochloride) (19.6 g, 0.26 mol, 2 equiv) was added and the reaction mixture was stirred overnight at room temperature. The reaction mixture was quenched with an aqueous solution of HCl (1 N). The mixture was extracted with CH$_2$Cl$_2$. The separated organic layer was dried (MgSO$_4$), filtered and the solvent was evaporated. The residue was purified by column chromatography over silica gel (eluent: CH$_2$Cl$_2$; SiO$_2$ 15-40 µm). Yield: 26 g of intermediate 6.

b) Preparation of Intermediate 7

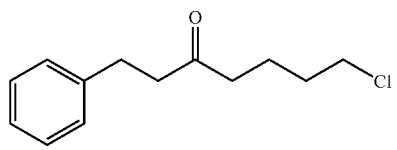 [SMILES: O=C(CCCCCl)CCc1ccccc1]

Intermediate 6 was added at 0° C. to a mixture of 4-chlorobutyl magnesiumbromide (1.5 equiv.) in THF (35 ml). The mixture was then refluxed for 5 hours, and quenched with NH$_4$Cl. The mixture was extracted with EtOAc. The separated organic layer was dried (MgSO$_4$), filtered and the solvent was evaporated. Yield: 20.5 g of intermediate 7 (quantitative yield).

c) Preparation of Intermediate 8

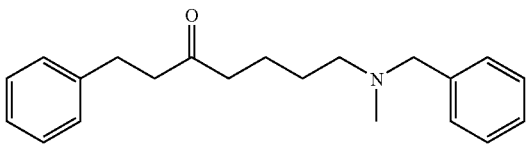 [SMILES: CN(CCCCC(=O)CCc1ccccc1)Cc1ccccc1]

A mixture of intermediate 7 (20.5 g, 0.09 mol), N-methylbenzyl amine (11.7 ml, 0.09 mol, 1 equiv.), K$_2$CO$_3$ (13.8 g, 0.1 mol, 1.1 equiv) in acetonitrile (200 ml) was refluxed overnight. The mixture was then cooled down to room temperature and water and Et$_2$O were added. The mixture was extracted with Et$_2$O. The separated organic layer was washed with an aqueous HCl solution (1N) and then with an aqueous NaOH solution (3N). The organic layer was dried and the solvent was evaporated. Yield: 7.86 g of intermediate 8 (29%).

d) Preparation of Intermediate 9

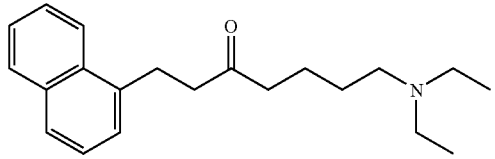 [SMILES: CCN(CC)CCCCC(=O)CCc1cccc2ccccc12]

Intermediate 9 was prepared according to the same procedure as intermediate 8. Yield: 10%.

Example A4 a) Preparation of Intermediate 10

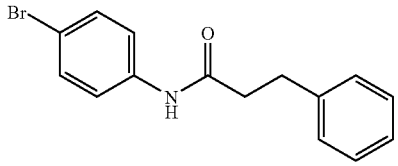 [SMILES: O=C(CCc1ccccc1)Nc1ccc(Br)cc1]

Benzenepropanoyl chloride (0.488 mol) was added dropwise at room temperature to a solution of 4-bromobenzenamine (0.407 mol) in Et$_3$N (70 ml) and CH$_2$Cl$_2$ (700 ml) and the mixture was stirred at room temperature overnight. The mixture was poured out into water and concentrated NH$_4$OH, and extracted with CH$_2$Cl$_2$. The organic layer was dried (MgSO$_4$), filtered, and the solvent was evaporated. The residue was crystallized from diethyl ether. The residue (119.67 g) was taken up in CH$_2$Cl$_2$ and washed with HCl 1N. The organic layer was dried (MgSO$_4$), filtered, and the solvent was evaporated. Yield: 107.67 g of intermediate 10.

b) Preparation of Intermediate 11

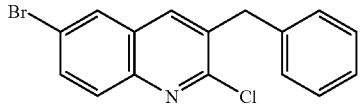 [SMILES: Clc1nc2ccc(Br)cc2cc1Cc1ccccc1]

The reaction was carried out twice. POCl$_3$ (1.225 mol) was added dropwise at 10° C. to DMF (0.525 mol). Then intermediate 10 (0.175 mol) was added at room temperature. The mixture was stirred overnight at 80° C., poured out on ice and extracted with CH$_2$Cl$_2$. The organic layer was dried (MgSO$_4$), filtered, and the solvent was evaporated. Yield: 77.62 g of intermediate 11 (67%).

c) Preparation of Intermediate 12

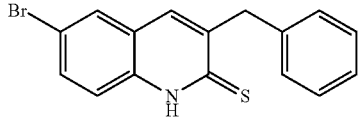 [SMILES: S=c1[nH]c2ccc(Br)cc2cc1Cc1ccccc1]

A mixture of intermediate 11 (0.045 mol) and thiourea (0.05 mol) in ethanol (150 ml) was stirred and refluxed for 8 hours and then brought to room temperature. A solution of KOH (0.068 mol) in water (15 ml) was added. The mixture was stirred and refluxed for 1 hour and poured out on ice. The precipitate was filtered off, washed with H$_2$O and dried. Yield: 11 g of intermediate 12 (74%).

d) Preparation of Intermediate 13

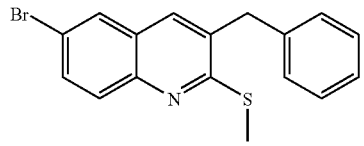

CH$_3$I (0.037 mol) was added slowly at room temperature to a mixture of intermediate 12 (0.033 mol) and K$_2$CO$_3$ (0.037 mol) in 2-propanone (150 ml). The mixture was stirred at room temperature for 8 hours, poured out into H$_2$O and extracted with CH$_2$Cl$_2$. The organic layer was separated, dried (MgSO$_4$), filtered and the solvent was evaporated. Yield: 11.2 g. Part of this fraction (2 g) was crystallized from diethyl ether. The precipitate was filtered off and dried. Yield: 1.45 g of intermediate 13 (70%).

Example A5 a) Preparation of Intermediate 14

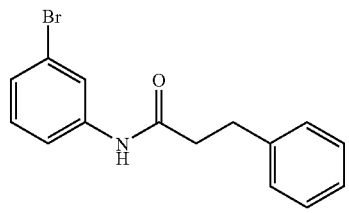 [SMILES: O=C(CCc1ccccc1)Nc1cccc(Br)c1]

Benzenepropanoyl chloride (0.67 mol) was added dropwise at 5° C. to a mixture of 3-bromobenzenamine (0.58 mol) and Et$_3$N (0.72 mol) in CH$_2$Cl$_2$ (1000 ml). The mixture was stirred at room temperature for 4 hours, poured out into ice water and NH$_4$OH. The organic layer was washed with HCl 1N, then with K$_2$CO$_3$ 10%, dried (MgSO$_4$), filtered, and the solvent was evaporated till dryness. Yield: 190 g of intermediate 14.

b) Preparation of Intermediate 15 and 16

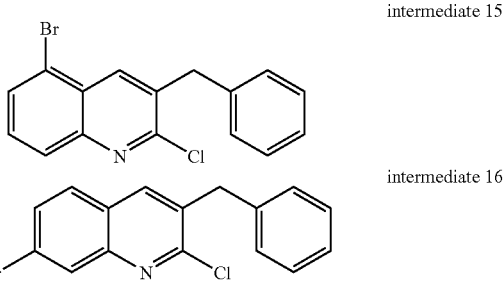

POCl$_3$ (2.3 mol) was added dropwise at 5° C. to DMF (0.98 mol). The mixture was brought to room temperature. Intermediate 14 (0.33 mol) was added. The mixture was stirred at 85° C. for 6 hours, then cooled to room temperature, poured out into ice water. CH$_2$Cl$_2$ was added. Both layers were stirred for 2 hours. The mixture was extracted with CH$_2$Cl$_2$. The organic layer was washed with K$_2$CO$_3$ 10%, dried (MgSO$_4$), filtered and the solvent was evaporated. The residue (84 g) was purified by column chromatography over silica gel (eluent: CH$_2$Cl$_2$/cyclohexane 30/70; 20-45 μm). The desired fractions were collected and the solvent was evaporated. Yield: 34.1 g of intermediate 15 (31%) and 9 g of intermediate 16 (8%).

c-1) Preparation of Intermediate 17

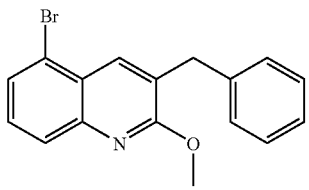 [SMILES: COc1nc2cccc(Br)c2cc1Cc1ccccc1]

A mixture of intermediate 15 (0.1 mol) and NaOCH$_3$ (0.53 mol) in methanol (340 ml) was stirred and refluxed for 20 hours, then cooled to room temperature, poured out into ice water and extracted with CH$_2$Cl$_2$. The organic layer was separated, dried (MgSO$_4$), filtered, and the solvent was evaporated. Yield: 79% of intermediate 17. (mp. 100° C.)

c-2) Preparation of Intermediate 18

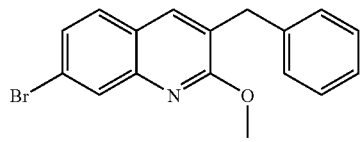 [SMILES: COc1nc2cc(Br)ccc2cc1Cc1ccccc1]

Intermediate 18 was prepared according to the same protocol as intermediate 17, but starting from intermediate 16. Yield: 96% of intermediate 18. (mp. 96° C.)

c-3) Preparation of Intermediate 19

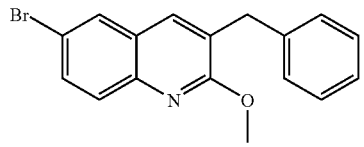

A mixture of intermediate 11 (0.233 mol) in CH$_3$ONa (300%) in methanol (222.32 ml) and methanol (776 ml) was stirred and refluxed overnight, then poured out on ice and extracted with CH$_2$Cl$_2$. The organic layer was separated, dried (MgSO$_4$), filtered and the solvent was evaporated. The residue was purified by column chromatography over silica gel (eluent: CH$_2$Cl$_2$/cyclohexane 20/80 and then 100/0; 20-45 μm). The pure fractions were collected and the solvent was evaporated. Yield: 25 g of intermediate 19 (33%) (melting point: 84° C.).

c-4) Preparation of Intermediate 20

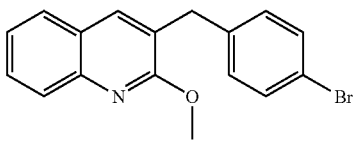 [SMILES: COc1nc2ccccc2cc1Cc1ccc(Br)cc1]

Intermediate 20 was prepared according to the same protocol as intermediate 19.

Yield: 90%.

Example A6

Preparation of Intermediate 21

Intermediate 21

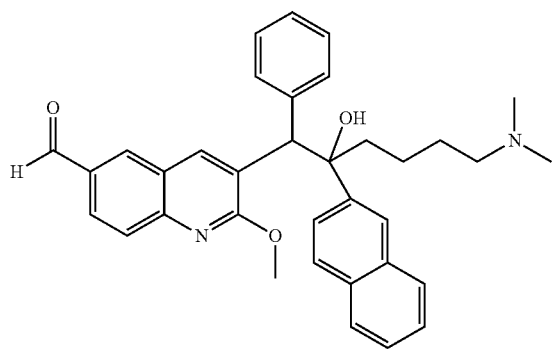

(dia B)

n-BuLi (1.6M in hexane, 4.4 ml, 0.00283 mol) was added dropwise at −70° C. under nitrogen flow to a solution of final compound 18 (0.00283 mol) in THF (17 ml). The mixture was stirred for 1 hour and 30 minutes at −70° C. and then N,N-dimethyl-formamide (0.014 mol) was added. The resulting mixture was stirred for 2 hours at −70° C. and then water was added. The mixture was extracted with EtOAc. The organic layer was washed with water then brine and was dried over MgSO$_4$, filtered and evaporated till dryness. The residue was crystallized from DIPE. Yield: 0.82 g of intermediate 21 (54%).

Example A7 a) Preparation of Intermediate 22

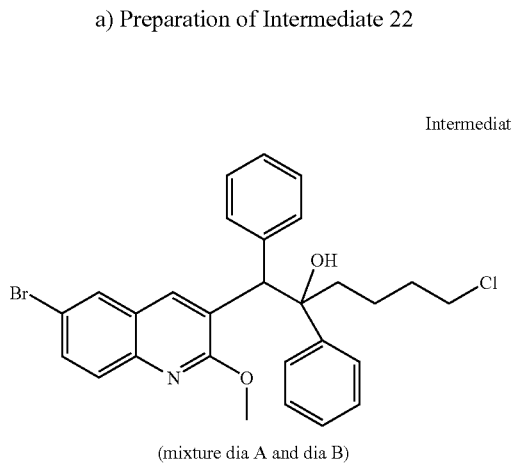

Intermediate 22

(mixture dia A and dia B)

n-BuLi (38 ml, 0.03 mol. 2 equiv) was added dropwise at −20° C. to a solution of diisopropylamine (8.6 ml, 0.03 mol. 2 equiv) in THF (30 ml) under $N_2$ flow. The mixture was stirred at −20° C. for 20 minutes, and then cooled to −70° C. A solution of intermediate 19 (10 g, 0.015 mol) in THF (30 ml) was added. The mixture was stirred at −70° C. for 1 h, and then a solution of intermediate 2b (7.8 g, 0.019 mol, 1.3 equiv) in THF (30 ml) was added. The mixture was stirred at −70° C. for 1 h. Water was added and the mixture was extracted with EtOAc. The organic layer was separated, washed with brine, dried over $MgSO_4$, filtered and the solvent was evaporated. The residue was purified by column chromatography over silica gel (eluent: Cyclohexane/EtOAc: 95/5; 20-45 μm) to give rise to intermediate 22 (15.2 g, 95%) (mixture of dia A and dia B).

Example A8 a) Preparation of Intermediate 23

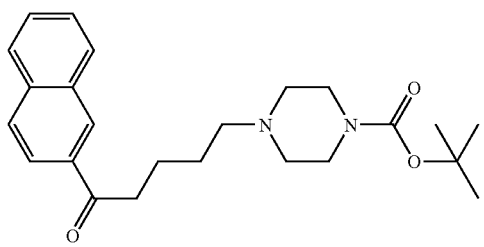 [SMILES: CC(C)(C)OC(=O)N1CCN(CCCCC(=O)c2ccc3ccccc3c2)CC1]

A mixture of intermediate 2 (0.00405 mol), N-(tert-butoxycarbonyl)piperazine (0.0081 mol) and potassium carbonate (0.012 mol) in acetonitrile (12 ml) was stirred under reflux for 2 days and was then cooled to room temperature, filtered and the solvent was evaporated. The residue was purified by column chromatography over silica gel (eluent: hexane/EtOAc 5:1 to 1:1; 15-40 μm). The pure fractions were collected and the solvent was evaporated. Yield: 0.76 g of intermediate 23 (47%).

b) Preparation of Intermediate 24

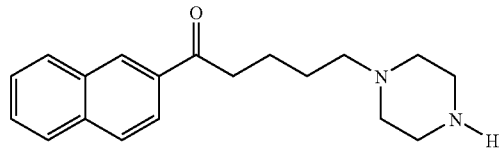 [SMILES: O=C(CCCCN1CCNCC1)c1ccc2ccccc2c1]

A solution of intermediate 23 (0.00191 mol) and trifluoroacetic acid (0.019 mol) in $CH_2Cl_2$ (6 ml) was stirred at room temperature overnight then poured out into water. Sodium hydroxide (pellets) was added until basic pH and the mixture was extracted with $CH_2Cl_2$. The organic layer was separated, washed with water, dried over $MgSO_4$, filtered and the solvent was evaporated. Yield: 0.50 g of intermediate 24 (88%).

Example A9 a) Preparation of Intermediate 25

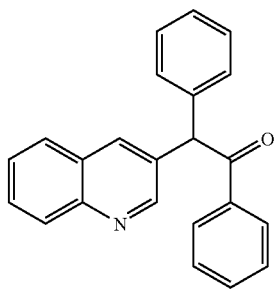

Intermediate 25

A mixture of deoxybenzoin (1 mmol), 3-bromoquinoline (1 mmol), XPHOS (0.08 mmol), palladium diacetate (0.04 mmol), cesium carbonate (2 mmol) in xylene (4 ml) was flushed with $N_2$ and heated at 145° C. for 20 hours. The reaction was cooled to room temperature and 2 ml of $H_2O$ and 10 ml of $CH_2Cl_2$ were added. The organic layer was separated, dried over $MgSO_4$, filtered, and the solvent was evaporated. The residue was purified by HPLC on RP with $NH_4HCO_3$-buffer. Yield: 87 mg (27%) of intermediate 25.

b) Preparation of Intermediate 26

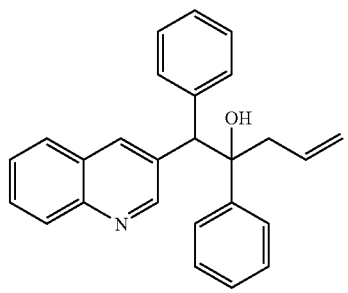

Intermediate 26

Intermediate 25 (0.269 mmol) was dissolved in THF (3 ml) and a solution of allylmagnesium bromide (1M in $Et_2O$, 1 mmol) was added at room temperature. After stirring for 2 hours at room temperature, 3 ml saturated NH₄Cl solution was added and stirring was continued for 1 hour. The mixture was extracted with CH₂Cl₂, the layers were separated on extrelute and the organic layer was concentrated in vacuo. The residue was purified by HPLC on RP with NH₄HCO₃-buffer. Yield: 25 mg (25%) of intermediate 26.

B. Preparation of the Final Compounds

Example B1

Preparation of Compounds 1 and 2

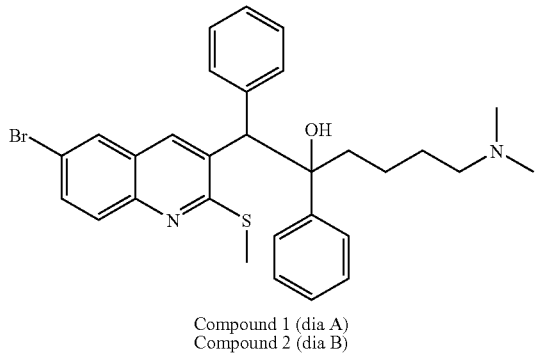 [SMILES: CSc1nc2ccc(Br)cc2cc1C(c1ccccc1)C(O)(CCCCN(C)C)c1ccccc1]

Compound 1 (dia A)
Compound 2 (dia B)

n-BuLi 1.6M in hexane (0.0035 mol) was added dropwise at −20° C. to a solution of N-(1-methylethyl)-2-propanamine (0.0035 mol) in THF (7 ml) under N₂ flow. The mixture was stirred at −20° C. for 20 minutes, then cooled to −70° C. A solution of intermediate 13 (0.003 mol) in THF (10 ml) was added. The mixture was stirred at −70° C. for 1 hour. A solution of 5-(dimethylamino)-1-phenyl-1-pentanone (prepared according to A1Ac), (0.0035 mol) in THF (10 ml) was added. The mixture was stirred at −70° C. for 3 hours. H₂O was added. The mixture was extracted with EtOAc. The organic layer was washed with saturated NaCl, dried (MgSO₄), filtered and the solvent was evaporated. The residue (2 g) was purified by column chromatography over silica gel (eluent: CH₂Cl₂/CH₃OH/NH₄OH 94/6/0.3; 15-40 μm). Two fractions were collected and the solvent was evaporated. Residue 1 was crystallized from DIPE. The precipitate was filtered off and dried. Yield: 2% of compound 1 (diastereoisomer A). Residue 2 was crystallized from DIPE. The precipitate was filtered off and dried. Yield: 0.174 g of compound 2 (11%) (diastereoisomer B).

Preparation of Compounds 3 and 4

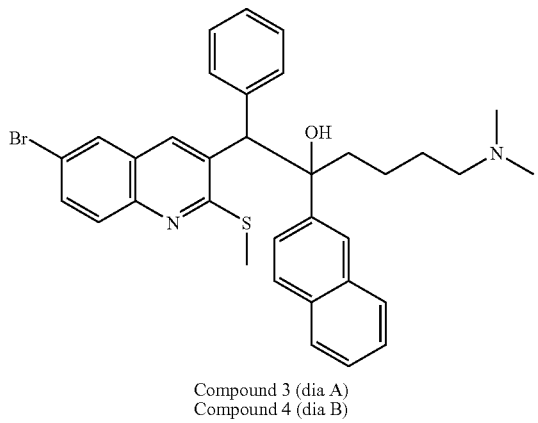 [SMILES: CSc1nc2ccc(Br)cc2cc1C(c1ccccc1)C(O)(CCCCN(C)C)c1ccc2ccccc2c1]

Compound 3 (dia A)
Compound 4 (dia B)

These compounds (compound 3, diastereoisomer A and compound 4, diastereoisomer B) were prepared according to B1, starting from intermediate 3a and intermediate 13.

Example B2a

Preparation of Compounds 5 and 6

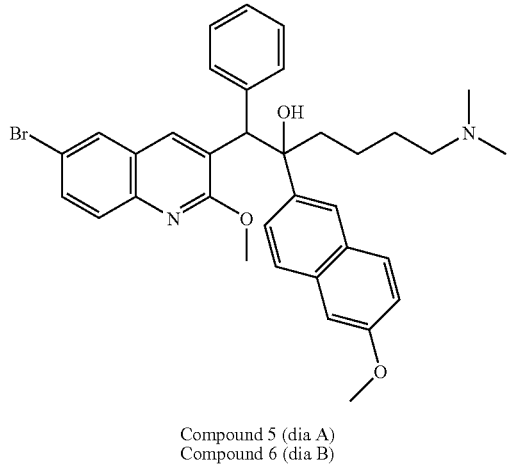 [SMILES: COc1ccc2cc(C(O)(CCCCN(C)C)C(c3ccccc3)c3cc4cc(Br)ccc4nc3OC)ccc2c1]

Compound 5 (dia A)
Compound 6 (dia B)

n-BuLi 1.6M in hexane (0.0073 mol) was added dropwise at −20° C. to a solution of N-(1-methylethyl)-2-propanamine (0.0073 mol) in THF (15 ml). The mixture was stirred at −20° C. for 20 minutes, then cooled to −70° C. A solution of intermediate 19 (0.0061 mol) in THF (20 ml) was added. The mixture was stirred at −70° C. for 1 hour. A solution of intermediate 5 (0.0073 mol) in THF (20 ml) was added. The mixture was stirred at −70° C. for 3 hours, then poured out on ice at −20° C. and extracted with EtOAc. The organic layer was washed with saturated NaCl, dried (MgSO₄), filtered and the solvent was evaporated. The residue (4.6 g) was purified by column chromatography over silica gel (eluent: CH₂Cl₂/CH₃OH/NH₄OH 96/4/0.3; 15-40 μm). Two fractions were collected and the solvent was evaporated. Yield of residue 1: 0.95 g of compound 5 (25%) (diastereoisomer A); (mp. 96° C.). Residue 2 was crystallized from DIPE. The precipitate was filtered off and dried. Yield: 0.44 g of compound 6 (12%). (diastereoisomer B; mp. 164° C.)

Preparation of Compounds 7 and 8

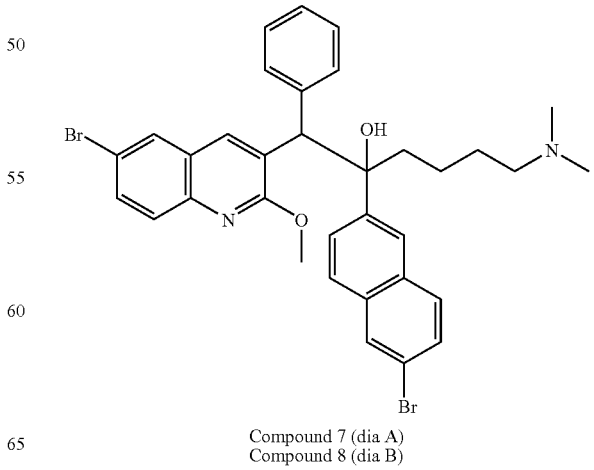

Compound 7 (dia A)
Compound 8 (dia B)

These compounds (compound 7, diastereoisomer A and compound 8, diastereoisomer B) were prepared according to the same protocol, but starting from 6-bromo-2-methoxy-3-(phenylmethyl)quinoline and 1-(6-bromo-naphthalen-2-yl)-5-dimethylamino-pentan-1-one (prepared according to A1Ac).

Example B2b

Preparation of Compounds 9 and 10

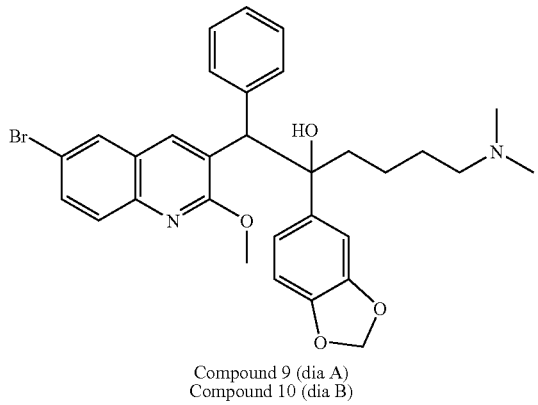 [SMILES: COc1nc2ccc(Br)cc2cc1C(c1ccccc1)C(O)(CCCCN(C)C)c1ccc2c(c1)OCO2]

Compound 9 (dia A)
Compound 10 (dia B)

A solution of intermediate 19 (0.0031 mol) in THF (10 ml) was added dropwise at −70° C. to a solution of N-(1-methylethyl)-2-propanamine, lithium (0.0035 mol) in THF (10 ml). The mixture was stirred at −70° C. for 1 hour and 30 minutes. A solution of (0.0041 mol), (prepared according to A1Ac) in THF (12 ml) was added. The mixture was stirred at −70° C. for 3 hours, poured out into −30° C. and extracted with $CH_2Cl_2$. The organic layer was separated, dried ($MgSO_4$), filtered, and the solvent was evaporated. The residue (5 g) was purified by column chromatography over silica gel (eluent: $CH_2Cl_2$/$CH_3OH$/$NH_4OH$ 93/7/0.5; 15-40 μm). Two fractions were collected and the solvent was evaporated. Residue 1 was crystallized from DIPE. The precipitate was filtered off and dried. Yield: 0.084 g of compound 9 (9%); (diastereoisomer A; mp. 98° C.). Residue 2 was crystallized from DIPE. The precipitate was filtered off and dried. Yield: 0.126 g of compound 10 (14%). (diastereoisomer B; mp. 110° C.)

Example B2c

Preparation of Compounds 11 and 12

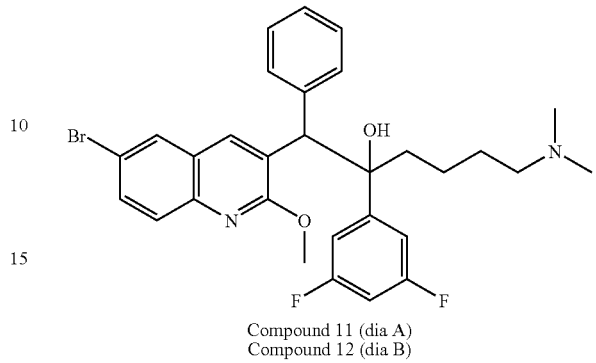

Compound 11 (dia A)
Compound 12 (dia B)

n-BuLi 1.6M in hexane (0.0041 mol) was added dropwise at −20° C. to a solution of N-(1-methylethyl)-2-propanamine (0.0041 mol) in THF (8 ml) under $N_2$ flow. The mixture was stirred at −20° C. for 20 minutes, then cooled to −70° C. A solution of intermediate 19 (0.0034 mol) in THF (12 ml) was added. The mixture was stirred at −70° C. for 1 hour. A solution of 1-(3,5-difluoro-phenyl)-5-dimethylamino-pentan-1-one 4 (0.0041 mol), (prepared according to A1Ac) in THF (10 ml) was added. The mixture was stirred at −70° C. for 4 hours. $H_2O$ was added. The mixture was extracted with EtOAc. The organic layer was washed with saturated NaCl, dried ($MgSO_4$), filtered and the solvent was evaporated. The residue (2.1 g) was purified by column chromatography over silica gel (eluent: $CH_2Cl_2$/$CH_3OH$/$NH_4OH$ 94/6/0.5; 15-40 μm). Two fractions were collected and the solvent was evaporated. Residue 1 was crystallized from DIPE. The precipitate was filtered off and dried. Yield: 0.17 g of compound 11 (9%); (diastereoisomer A; mp. 157° C.). Residue 2 was crystallized from DIPE. The precipitate was filtered off and dried. Yield: 0.21 g of compound 12 (11%). (diastereoisomer B; mp. 175° C.)

Example B2d

Preparation of Compounds 13 and 14

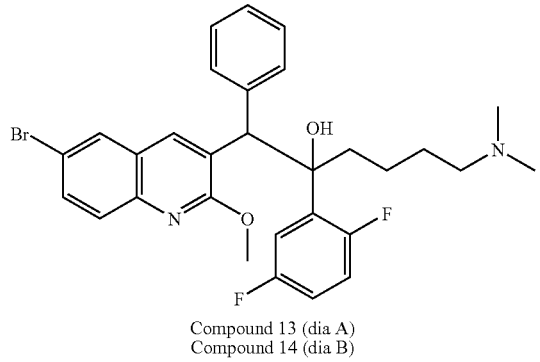 [SMILES: COc1nc2ccc(Br)cc2cc1C(c1ccccc1)C(O)(CCCCN(C)C)c1cc(F)ccc1F]

Compound 13 (dia A)
Compound 14 (dia B)

n-BuLi 1.6M in hexane (0.0041 mol) was added dropwise at −20° C. to a solution of N-(1-methylethyl)-2-propanamine (0.0041 mol) in THF (8 ml) under $N_2$ flow. The mixture was stirred at −20° C. for 20 minutes, then cooled to −70° C. A solution of intermediate 19 (0.0034 mol) in THF (12 ml) was added. The mixture was stirred at −70° C. for 1 hour. A solution of 1-(2,5-difluorophenyl)-5-dimethylamino-pentan-1-one (0.0041 mol), (prepared according to A1Ac) in THF (10 ml) was added. The mixture was stirred at −70° C. for 4 hours. H$_2$O was added. The mixture was extracted with EtOAc. The organic layer was washed with saturated NaCl, dried (MgSO$_4$), filtered and the solvent was evaporated. The residue (2.2 g) was purified by column chromatography over silica gel (eluent: CH$_2$Cl$_2$/CH$_3$OH/NH$_4$OH 95/5/0.5; 15-40 μm). Two fractions were collected and the solvent was evaporated. Residue 1 was crystallized from DIPE. The precipitate was filtered off and dried. Yield: 0.13 g of compound 13 (7%); (diastereoisomer A; mp. 166° C.). Residue 2 was crystallized from DIPE. The precipitate was filtered off and dried. Yield: 0.15 g of compound 14 (8%). (diastereoisomer B; mp. 157° C.)

Example B2e

Preparation of Compounds 15 and 16

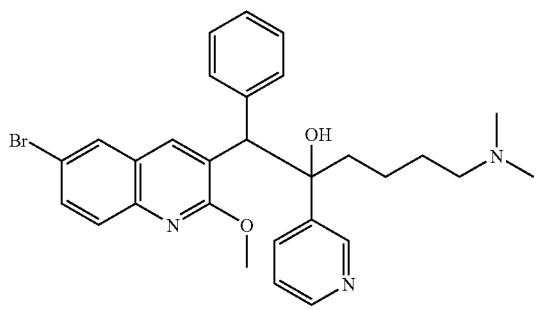

Compound 15 (dia A)
Compound 16 (dia B)

n-BuLi 1.6M in hexane (0.0072 mol) was added dropwise at −20° C. to a solution of N-(1-methylethyl)-2-propanamine (0.0072 mol) in THF (20 ml) under N$_2$ flow. The mixture was stirred at −20° C. for 20 minutes, then cooled to −70° C. A solution of intermediate 19 (0.0066 mol) in THF (21 ml) was added. The mixture was stirred at −70° C. for 1 hour and 30 minutes. A solution of 5-dimethylamino-1-pyridin-3-yl-pentan-1-one, (prepared according to A1Ac) (0.0092 mol) in THF (20 ml) was added. The mixture was stirred at −70° C. for 3 hours. H$_2$O was added at −30° C. The mixture was extracted with diethyl ether. The organic layer was separated, dried (MgSO$_4$), filtered and the solvent was evaporated. The residue (3.4 g) was purified by column chromatography over silica gel (eluent: CH$_2$Cl$_2$/CH$_3$OH/NH$_4$OH 92/8/0.5; 15-40 μm). Two fractions were collected and the solvent was evaporated. Fraction 1 was crystallized from DIPE. The precipitate was filtered off and dried. Yield: 0.065 g of compound 15 (3%); (diastereoisomer A; mp. 150° C.). Fraction 2 was crystallized from DIPE. The precipitate was filtered off and dried. Yield: 0.062 g of compound 16 (3%). (diastereoisomer B; mp. 98° C.)

Example B2f

Preparation of Compounds 17 and 18

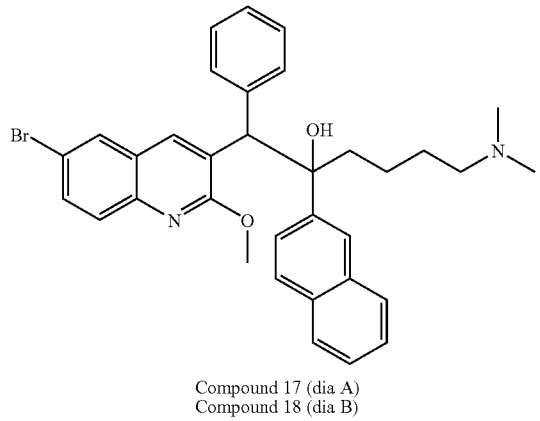 [SMILES: COc1nc2ccc(Br)cc2cc1C(c1ccccc1)C(O)(CCCCN(C)C)c1ccc2ccccc2c1]

Compound 17 (dia A)
Compound 18 (dia B)

n-BuLi 1.6M in hexane (0.0073 mol) was added at −20° C. to a mixture of N-(1-methyl-ethyl)-2-propanamine (0.0073 mol) in THF (10 ml) under N$_2$ flow. The mixture was stirred for 20 minutes, then cooled to −70° C. A solution of intermediate 19 (0.006 mol) in THF (10 ml) was added slowly. The mixture was stirred for 1 hour and 30 minutes. A solution of intermediate 3a (0.0091 mol) in THF (10 ml) was added. The mixture was stirred for 1 hour and 30 minutes. H$_2$O was added. The mixture was extracted with EtOAc. The organic layer was separated, dried (MgSO$_4$), filtered, and the solvent was evaporated. The residue (4.1 g) was purified by column chromatography over silica gel (eluent: CH$_2$Cl$_2$/iPrOH/NH$_4$OH 90/10/0.5; 15-40 μm). The desired fractions were collected and the solvent was evaporated. Fraction 1 was crystallized from iPrOH/DIPE. The precipitate was filtered off and dried. Yield: 0.214 g of compound 17 (diastereoisomer A; mp. 170° C.). Fraction 2 was crystallized from iPrOH/DIPE. The precipitate was filtered off and dried. Yield: 0.039 g of compound 18 (diastereoisomer B; mp. 145° C.).

Example B2g

Preparation of Compound 19

Compound 19 (dia A)

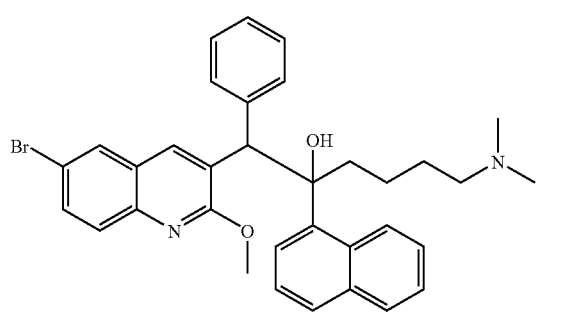

n-BuLi 1.6M in hexane (0.002 mol) was added at −20° C. to a solution of N-(1-methyl-ethyl)-2-propanamine (0.002 mol) in THF (6 ml) under N$_2$ flow. The mixture was stirred for 20 minutes, then cooled to −70° C. A solution of intermediate 19 (0.002 mol) in THF (2 ml) was added. The mixture was stirred at −70° C. for 1 hour and 30 minutes. A solution of 5-dimethylamino-1-naphthalen-1-yl-pentan-1-one (0.0024 mol) (prepared according to the procedure of A1Ac) in THF (2 ml) was added. The mixture was stirred for 1 hour and 30 minutes. H$_2$O was added. The mixture was extracted with EtOAc. The organic layer was separated, dried (MgSO$_4$), filtered, and the solvent was evaporated. The residue was purified by column chromatography over silica gel (eluent: CH$_2$Cl$_2$ 100; 15-40 μm). The first desired fraction was collected and the solvent was evaporated. The residue was further purified by column chromatography over silica gel (eluent: CH$_2$Cl$_2$/CH$_3$OH/NH$_4$OH 95/5/0.1; 15-40 μm). The pure fractions were collected and the solvent was evaporated. Yield: 0.029 g of compound 19 (diastereoisomer A).

Example B2h

Preparation of Compounds 20 and 21

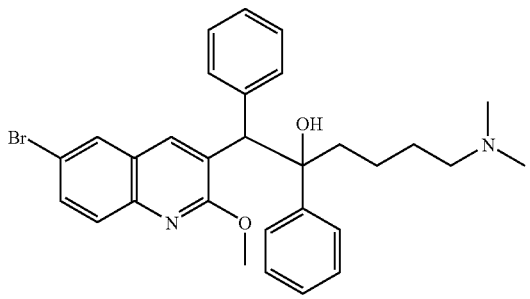

Compound 20 (dia A)
Compound 21 (dia B)

n-BuLi 1.6M in hexane (0.0547 mol) was added dropwise at −78° C. under N$_2$ flow to a mixture of N-(1-methylethyl)-2-propanamine (0.0547 mol) in THF (70 ml). The mixture was brought to 0° C. and then cooled again to −78° C. A solution of intermediate 19 (0.0365 mol) in THF (70 ml) was added. The mixture was stirred at −78° C. for 1 hour. A solution of 5-dimethylamino-1-phenyl-pentan-1-one (0.043 mol) (prepared according to A1Ac), in THF (70 ml) was added. The mixture was brought to −30° C. while stirring, then poured out into ice water and extracted with EtOAc. The organic layer was separated, dried (MgSO$_4$), filtered and the solvent was evaporated. The residue (22.4 g) was purified by column chromatography over silica gel (eluent: CH$_2$Cl$_2$/CH$_3$OH/NH$_4$OH 96/4/0.1). Two pure fractions were collected and their solvents were evaporated. Fraction 1 was crystallized from DIPE. The precipitate was filtered off and dried. Yield: 0.56 g of compound 20 (5%) (diastereoisomer A). Fraction 2 was crystallized from diethyl ether. The precipitate was filtered off and dried. Yield: 1.2 g of compound 21 (9.7%) (diastereoisomer B).

Example B2i

Preparation of Compounds 22, 23, 24 and 25

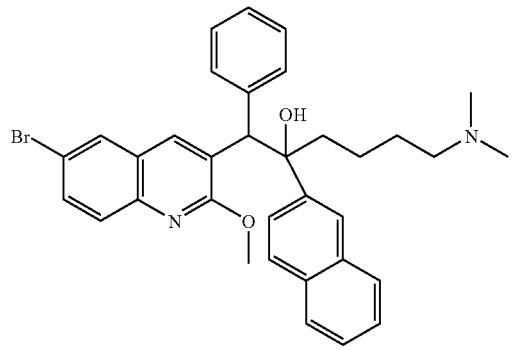

Compound 22 (B1)
Compound 23 (B2)
Compound 24 (A1)
Compound 25 (A2)

n-BuLi 1.6M in hexane (0.0117 mol) was added dropwise at −20° C. to a solution of N-(1-methylethyl)-2-propanamine (0.0117 mol) in THF (100 ml) under N$_2$ flow. The mixture was stirred at −20° C. for 20 minutes, then cooled to −70° C. A solution of intermediate 19 (0.0097 mol) in THF (30 ml) was added. The mixture was stirred for 1 hour. A solution of intermediate 3a (0.0117 mol) in THF (30 ml) was added. The mixture was stirred at −70° C. for 3 hours, then brought to −20° C., poured out into H$_2$O and extracted with EtOAc. The organic layer was washed with NaCl, dried (MgSO$_4$), filtered and the solvent was evaporated. The residue (6.5 g) was purified by column chromatography over silica gel (eluent: CH$_2$Cl$_2$/CH$_3$OH/NH$_4$OH 96/4/0.4; 15-40 μm). Two fractions were collected and the solvent was evaporated.

Fraction 1 was further purified by column chromatography over silica gel (eluent: heptane/EtOH/Triethylamine 97/3/0.1; 20 μm). Two fractions were collected and the solvent was evaporated Yield: 0.13 g of compound 24 (11%); (mp. 101° C.) and 0.13 g of compound 25 (11%). (mp. 96° C.)

Fraction 2 was further purified by column chromatography over silica gel (eluent: heptane/EtOH/Triethylamine 99/1/0.1; 20 μm). Two fractions were collected and the solvent was evaporated. Residue 1 was crystallized from DIPE. The precipitate was filtered off and dried. Yield: 0.156 g of compound 22 (7%); (mp. 166° C.). Residue 2 was crystallized from DIPE. The precipitate was filtered off and dried. Yield: 0.15 g of compound 23 (7%). (mp. 169° C.)

Example B2j

Preparation of Compounds 60 and 61

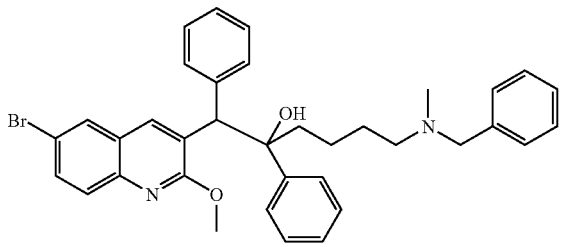

Compound 60 (dia A)
Compound 61 (dia B)

n-BuLi (0.0103 mol) was added dropwise at −20° C. to a solution of diisopropylamine (0.0103 mol) in THF (20 ml) under N$_2$ flow. The mixture was stirred at −20° C. for 20 minutes, then cooled to −70° C. A solution of intermediate 19 (0.00859 mol) in THF (28 ml) was added. The mixture was stirred at −70° C. for 1 hour and then a solution of intermediate 3c (0.0103 mol) in THF (29 ml) was added. The mixture was stirred at −70° C. for 2 hours. Water was added and the mixture was extracted with EtOAc. The organic layer was separated, washed with brine, dried over MgSO$_4$, filtered and the solvent was evaporated. The residue (6 g) was purified by column chromatography over silica gel (eluent: cyclohexane/EtOAc:65/35; 15-40 µm). Two fractions were collected and the solvent was evaporated. Yield: 0.55 g of compound 60 (11%) (fraction 1, dia A) and 0.71 g of compound 61 (14%) (fraction 2, dia B).

Example B2k

Preparation of Compounds 62, 63, 64, 65 and 66

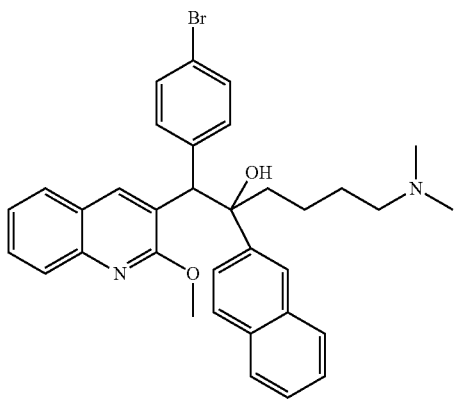

Compound 62 (mixture of dia A and dia B)
Compound 63 (A1)
Compound 64 (A2)
Compound 65 (B1)
Compound 66 (B2)

A solution of intermediate 20 (0.00661 mol) in THF (20 ml) was added to a solution of lithium diisopropylamide (commercially available, 2M in THF/heptane, 0.00793 mol) in THF (27 ml) at −70° C. The mixture was stirred at −70° C. for 2 hours. A solution of intermediate 3a (0.00661 mol) in THF (20 ml) was added. The mixture was stirred at −70° C. for 3 hours. Water was added and the mixture was extracted with EtOAc. The organic layer was separated, washed with brine, dried over MgSO$_4$, filtered and the solvent was evaporated. The residue was purified by column chromatography over silica gel (eluent: CH$_2$Cl$_2$/CH$_3$OH: 50/1; 15-40 µm). The pure fractions were collected and the solvent was evaporated. Yield: Compound 62 (a mixture of dia A and dia B) (30%).

A fraction of the previous compound 62 was purified by chiral column chromatography over silica gel (Supercritical Fluid Chromatography, chiralpack AD, eluent: CO$_2$/MeOH: 80/20). Four fractions were collected and the solvent was evaporated to obtain compound 63 (A1, 5%), compound 64 (A2, 4%), compound 65 (B1, 5%) and compound 66 (B2, 5%).

Example B21

Preparation of Compounds 106 and 107

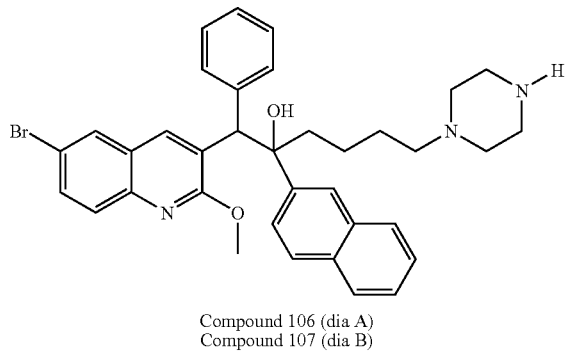 [SMILES: COc1nc2ccc(Br)cc2cc1C(c1ccccc1)C(O)(CCCCN1CCNCC1)c1ccc2ccccc2c1]

Compound 106 (dia A)
Compound 107 (dia B)

A solution of intermediate 19 (0.00169 mol) in THF (5 ml) was added to a solution of lithium diisopropylamide (commercially available, 2M in THF/heptane, 0.00202 mol) in THF (7 ml) at −70° C. The mixture was stirred at −70° C. for 2 hours. A solution of intermediate 24 (0.00169 mol) in THF (5 ml) was added. The mixture was stirred at −70° C. for 3 hours. Water was added and the mixture was extracted with EtOAc. The organic layer was separated, washed with brine, dried over MgSO$_4$, filtered and the solvent was evaporated. The residue was purified by column chromatography over silica gel (eluent: CH$_2$Cl$_2$/CH$_3$OH 90/10/0.1; 1540 µm). The pure fractions were collected and the solvent was evaporated. Yield: 0.055 g of a mixture of dia A and dia B (5%). This mixture was purified by column chromatography over silica gel (Sunfire C18-5 µm, MeOH/NH$_4$HCO$_3$ aq 0.5%: 80/20. Two fractions were collected and the solvent was evaporated. Yield: 0.008 g of compound 106 (1%) (fraction 1, dia A) and 0.01 g of compound 107 (1%) (fraction 2, dia B).

Example B3a

Preparation of Compounds 26 and 27

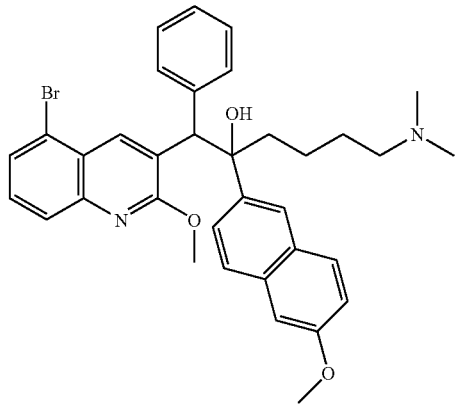

Compound 26 (dia A)
Compound 27 (dia B)

n-BuLi 1.6M in hexane (0.0073 mol) was added dropwise at −20° C. to a solution of N-(1-methylethyl)-2-propanamine (0.0073 mol) in THF (15 ml) under N₂ flow. The mixture was stirred at −20° C. for 20 minutes, then cooled to −70° C. A solution of intermediate 17 (0.0061 mol) in THF (20 ml) was added. The mixture was stirred at −70° C. for 1 hour. A solution of intermediate 5 (0.0073 mol) in THF (20 ml) was added. The mixture was stirred at −70° C. for 3 hours. H₂O was added. The mixture was extracted with EtOAc. The organic layer was washed with saturated NaCl, dried (MgSO₄), filtered and the solvent was evaporated. The residue (3.6 g) was purified by column chromatography over silica gel (eluent: CH₂Cl₂/CH₃OH/NH₄OH 96/4/0.4; 15-40 μm. Two fractions were collected and the solvent was evaporated. Residue 1 was crystallized from DIPE. The precipitate was filtered off and dried. Yield: 0.33 g of compound 26 (diastereoisomer A; mp. 164° C.). Residue 2 was crystallized from DIPE. The precipitate was filtered off and dried. Yield: 1.35 g of compound 27 (36%). (diastereoisomer B; mp. 180° C.)

Example B3b

Preparation of Compounds 28 and 29

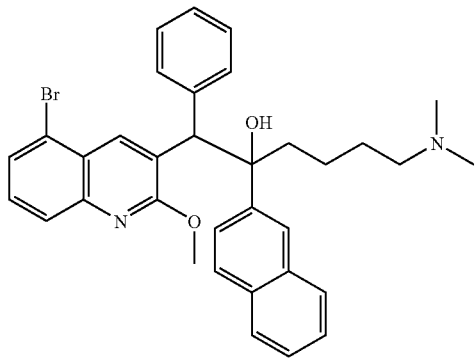

Compound 28 (dia A)
Compound 29 (dia B)

n-BuLi 1.6M in hexane (0.0036 mol) was added dropwise at −20° C. to a solution of N-(1-methylethyl)-2-propanamine (0.0036 mol) in THF (7 ml) under N₂ flow. The mixture was stirred at −20° C. for 20 minutes, then cooled to −70° C. A solution of intermediate 17 (0.003 mol) in THF (10 ml) was added. The mixture was stirred at −70° C. for 1 hour. A solution of intermediate 3a (0.0036 mol) in THF (10 ml) was added. The mixture was stirred at −70° C. for 4 hours. H₂O was added. The mixture was extracted with EtOAc. The organic layer was washed with H₂O, then with saturated NaCl, dried (MgSO₄), filtered and the solvent was evaporated. The residue (2 g) was purified by column chromatography over silica gel (eluent: CH₂Cl₂/CH₃OH/NH₄OH 94/6/0.3; 15-40 μm). Two fractions were collected and the solvent was evaporated. Residue 1 was crystallized from DIPE. The precipitate was filtered off and dried at 65° C. under vacuo. Yield: 0.091 g of compound 28 (5%); (diastereoisomer A; mp. 170° C.). Residue 2 was crystallized from DIPE. The precipitate was filtered off and dried. Yield: 0.11 g of compound 29 (6%). (diastereoisomer B; mp. 173° C.)

Example B4a

Preparation of Compounds 30 and 31

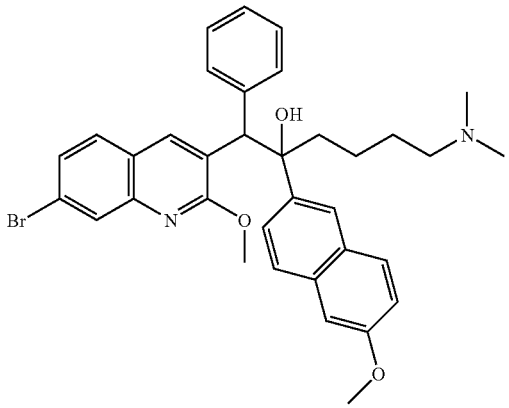

Compound 30 (dia A)
Compound 31 (dia B)

n-BuLi 1.6M in hexane (0.0073 mol) was added dropwise at −20° C. to a solution of N-(1-methylethyl)-2-propanamine (0.0073 mol) in THF (15 ml) under N₂ flow. The mixture was stirred at −20° C. for 20 minutes, then cooled to −70° C. A solution of intermediate 18 (0.0061 mol) in THF (20 ml) was added. The mixture was stirred at −70° C. for 1 hour. A solution of intermediate 5 (0.0073 mol) in THF (20 ml) was added. The mixture was stirred at −70° C. for 3 hours. H₂O was added. The mixture was extracted with EtOAc. The organic layer was washed with saturated NaCl, dried (MgSO₄), filtered and the solvent was evaporated. The residue (3.9 g) was purified by column chromatography over silica gel (eluent: CH₂Cl₂/CH₃OH/NH₄OH 96/4/0.4; 15-40 μm). Two fractions were collected and the solvent was evaporated. Residue 1 was crystallized from DIPE. The precipitate was filtered off and dried. Yield: 0.52 g of compound 30 (14%); (diastereoisomer A; mp. 160° C.). Residue 2 was crystallized from DIPE. The precipitate was filtered off and dried. Yield: 0.24 g of compound 31 (7%). (diastereoisomer B; mp. 174° C.)

Example B4b

Preparation of Compounds 32 and 33

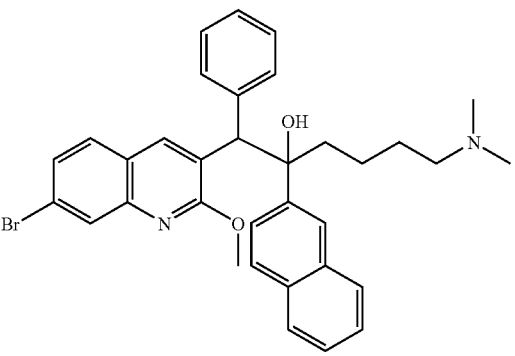

Compound 32 (dia A)
Compound 33 (dia B)

n-BuLi 1.6M in hexane (0.0036 mol) was added dropwise at –20° C. to a solution of N-(1-methylethyl)-2-propanamine (0.0036 mol) in THF (7 ml) under $N_2$ flow. The mixture was stirred at –20° C. for 20 minutes, then cooled to –70° C. A solution of intermediate 18 (0.003 mol) in THF (10 ml) was added. The mixture was stirred at –70° C. for 1 hour. A solution of intermediate 3a (0.0036 mol) in THF (10 ml) was added. The mixture was stirred at –70° C. for 4 hours. $H_2O$ was added. The mixture was extracted with EtOAc. The organic layer was washed with $H_2O$, then with saturated NaCl, dried ($MgSO_4$), filtered and the solvent was evaporated. The residue (2.1 g) was purified by column chromatography over silica gel (eluent: $CH_2Cl_2/CH_3OH/NH_4OH$ 95/5/0.2; 15-40 μm). Two fractions were collected and the solvent was evaporated. Yield: 0.18 g of compound 32 (10%) (diastereoisomer A). Fraction 2 was crystallized from DIPE. The precipitate was filtered off and dried at 65° C. under vacuo. Yield: 0.2 g of compound 33 (11%). (diastereoisomer B; mp. 198° C.)

Preparation of Compound 35

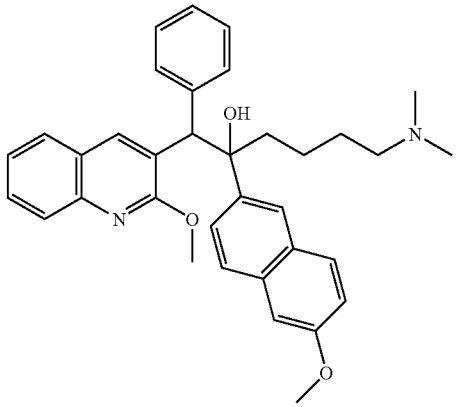

Compound 35 (dia A)

Compound 35 (diastereoisomer A) was prepared according to the same protocol, but starting from compound 5.

Example B5a

Preparation of Compound 34

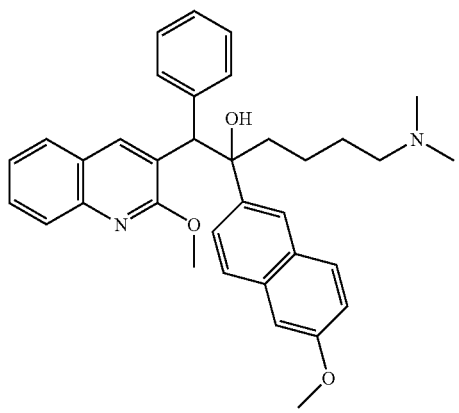

Compound 34 (dia B)

A mixture of compound 6 (0.0002 mol), $HCO_2^-NH_4^+$ (0.0012 mol) and Pd/C (0.15 g) in methanol (3 ml) was stirred and refluxed for 30 minutes, then cooled to room temperature, filtered and washed with $CH_2Cl_2$. The filtrate was washed with $H_2O$, then with saturated NaCl. The organic layer was separated, dried ($MgSO_4$), filtered and the solvent was evaporated. The residue was crystallized from DIPE. The precipitate was filtered off and dried. This fraction was dried at 60° C. under a vacuo. Yield: 0.054 g of compound 34 (42%). (diastereoisomer B; mp. 179° C.)

Example B5b

Preparation of Compound 36

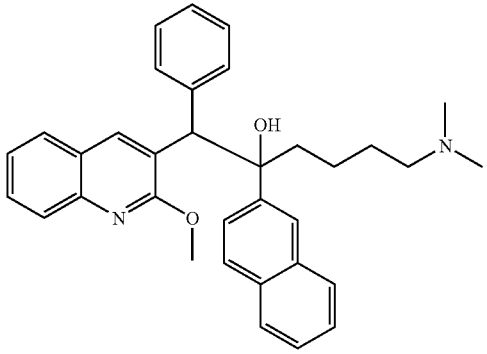

Compound 36 (dia A)

A mixture of compound 17 (0.0001 mol), $HCO_2^-NH_4^+$ (0.0008 mol) and Pd/C (0.1 g) in methanol (3 ml) was stirred and refluxed for 1 hour, then cooled to room temperature and filtered over celite. Celite was washed with $CH_2Cl_2$. The organic layer was washed with $H_2O$, then with saturated NaCl, dried ($MgSO_4$), filtered and the solvent was evaporated. The residue (0.11 g) was purified by column chromatography over kromasil (eluent gradient: $CH_2Cl/CH_3OH/NH_4OH$ 98/2/0.1 to 90/10/1; 3.5 μm). The pure fractions were collected and the solvent was evaporated. Yield: 0.037 g of compound 36 (43%) (diastereoisomer A; mp. 105° C.).

Example B5c

Preparation of Compound 37

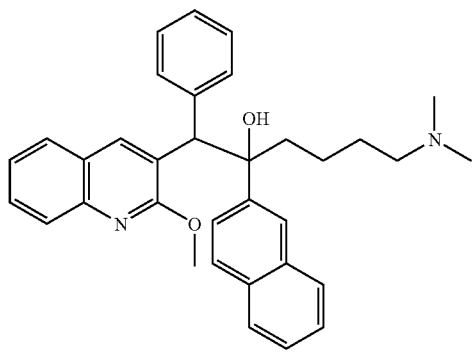

Compound 37 (dia B)

A mixture of compound 33 (0.0001 mol), HCO$_2^-$NH$_4^+$ (0.0008 mol) and Pd/C (0.1 g) in methanol (3 ml) was stirred at 65° C. for 1 hour, then cooled to room temperature and filtered over celite. Celite was washed with EtOAc. The organic layer was washed with H$_2$O, then with saturated NaCl, dried (MgSO$_4$), filtered and the solvent was evaporated. Yield: 0.071 g of compound 37 (83%) (diastereoisomer B).

Example B6

Preparation of Compound 38

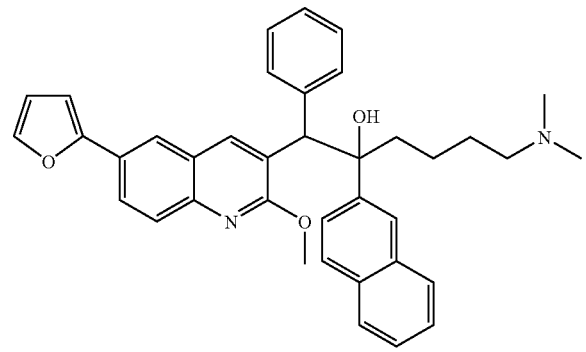

Compound 38 (dia B)

A mixture of compound 18 (0.0003 mol), 2-furanylboronic acid (0.0005 mol) and Pd(PPh$_3$)$_4$ (0.00003 mol) in DME (4 ml), methanol (2 ml) and K$_2$CO$_3$ 2M (0.34 ml) was stirred in a microwave oven at 65° C. for 15 minutes (P=300 W), then cooled to room temperature, poured out into H$_2$O and extracted with CH$_2$Cl$_2$. The organic layer was separated, dried (MgSO$_4$), filtered and the solvent was evaporated. The residue was purified by column chromatography over silica gel (eluent gradient: CH$_2$Cl$_2$/CH$_3$OH/NH$_4$OH 98/2/0.2 to 90/10/0.1; 5 μm). The pure fractions were collected and the solvent was evaporated. The residue was crystallized from DIPE. The precipitate was filtered off and dried. Yield: 0.05 g of compound 38 (26%). (diastereoisomer B; mp. 182° C.)

Preparation of Compound 39

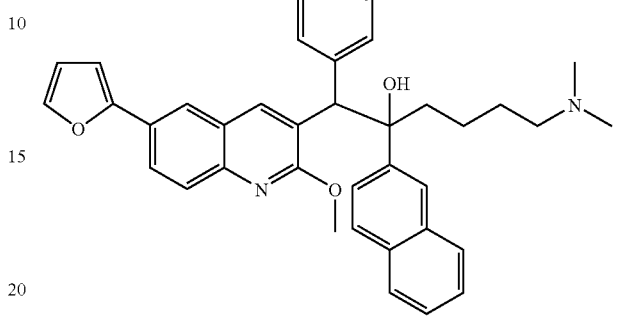

Compound 39 (dia A)

Compound 39 (diastereoisomer A) was prepared according to the same protocol, but starting from compound 17.

Example B7

Preparation of Compound 40

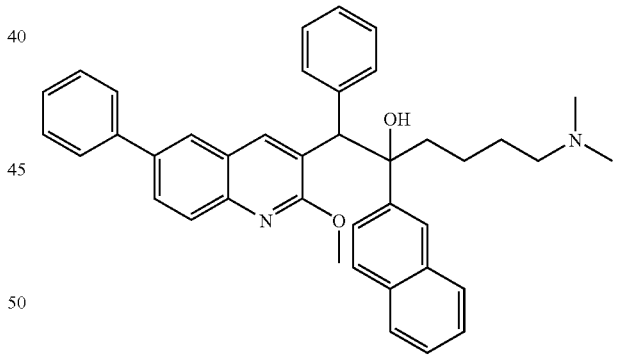

Compound 40 (dia A)

A mixture of compound 17 (0.0003 mol), phenylboronic acid (0.0005 mol) and Pd(PPh$_3$)$_4$ (0.04 g) in DME (4 ml), K$_2$CO$_3$ (0.34 ml) and methanol (2 ml) was stilled in a microwave oven (P=300 W) at 65° C. for 15 minutes, then cooled to room temperature. H$_2$O then CH$_2$Cl$_2$ were added. The mixture was filtered. The organic layer was separated, dried (MgSO$_4$), filtered and the solvent was evaporated. The residue was purified by column chromatography over kromasil (eluent gradient: CH$_2$Cl$_2$/CH$_3$OH/NH$_4$OH 98/2/0.2 to 90/10/1; 5 μm). The pure fractions were collected and the solvent was evaporated. This fraction was dried at 58° C. under vacuo.

Yield: 0.1 g of compound 40 (diastereoisomer A).

Preparation of Compound 41

Compound 41 (dia B)

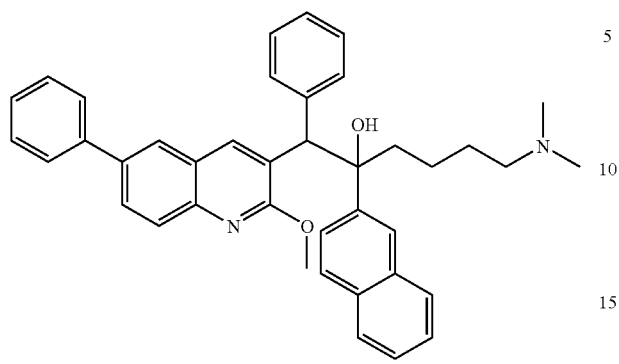

Compound 41 (diastereoisomer B) was prepared according to the same protocol, but starting from compound 18.

Example B8

Preparation of Compound 42

Compound 42 (dia B)

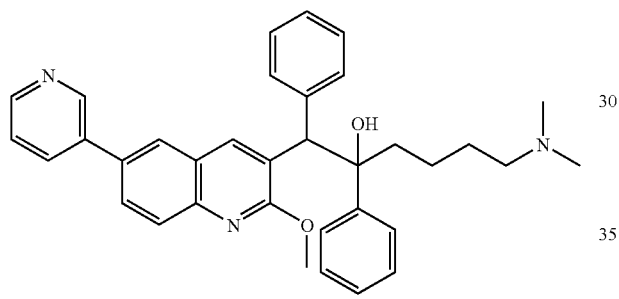

A mixture of compound 21 (0.0003 mol), 3-(1,3,2-dioxaborinan-2-yl)pyridine (0.0005 mol) and Pd(PPh$_3$)$_4$ (0.00003 mol) in DME (4 ml), methanol (2 ml) and K$_2$CO$_3$ (0.38 ml) was stirred in a microwave oven at 75° C. for 10 minutes (P=300 W), then cooled to room temperature, poured out into H$_2$O, extracted with CH$_2$Cl$_2$ and filtered. The organic layer was separated, dried (MgSO$_4$), filtered and the solvent was evaporated. The residue (0.17 g) was purified by column chromatography over kromasil (eluent gradient: CH$_2$Cl$_2$/CH$_3$OH/NH$_4$OH 98/2/0.1 to 90/10/1; 3.5 µm). Two fractions were collected and the solvent was evaporated. Yield: 0.073 g of compound 42 (37%). (diastereoisomer B; mp. 203° C.)

Preparation of Compound 43

Compound 43 (dia A)

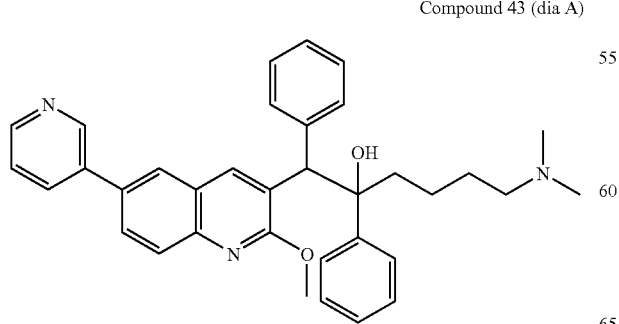

Compound 43 (diastereoisomer A) was prepared according to the same protocol, but starting from compound 20.

Example B9

Preparation of Compound 53 compound 53 (dia A)

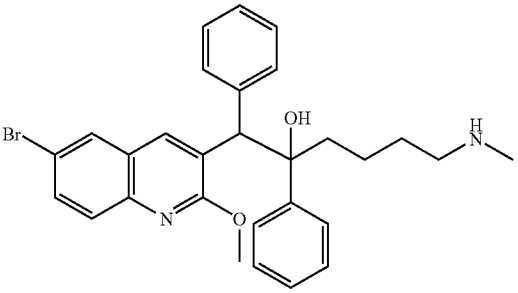

1-chloroethyl chloroformate (0.00108 mol) was added at room temperature to a mixture of compound 60 (0.0009 mol) in 1,2-dichloroethane (10 ml). The mixture was stirred at 80° C. for 1 hour. The solvent was evaporated. MeOH (10 ml) was added to the residue and the mixture was stirred and refluxed for 1 hour. The solvent was evaporated. The residue (2.8 g) was purified by column chromatography over silica gel (eluent: CH$_2$Cl$_2$/MeOH/NH$_4$OH 95/5/0.5 to 85/15/1.5; kromasil 5 µm). The pure fractions were collected and the solvent was evaporated. Yielding: 0.21 g of compound 53 (45%) (dia A, mp. 121° C.).

Example B10

Preparation of Compound 55

Compound 55 (dia B)

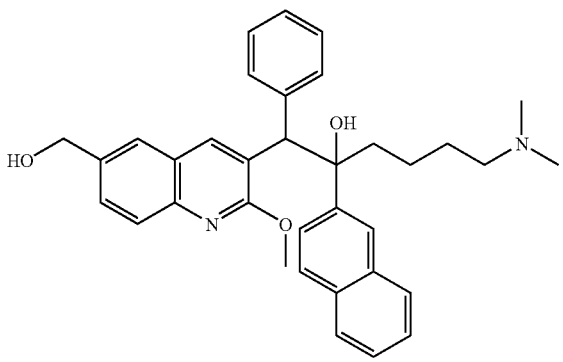

Sodium borohydride (0.00038 mol) was added at 5° C. to a solution of intermediate 21 (0.00038 mol) in MeOH (2 ml) and THF (2 ml). The mixture was stirred for 2 hours at 5° C. Then water was added and the mixture was extracted with EtOAc. The organic layer was washed with water then brine and was then dried over MgSO$_4$, filtered and evaporated till dryness. The residue (0.2 g) was purified by column chromatography over silica gel (eluent: CH$_2$Cl$_2$/CH$_3$OH/NH$_4$OH 96/4/0.4 to 88/12/1.2; kromasil Si 5 µm). The pure fractions were collected and the solvent was evaporated. Yield: 0.095 g

Example B11

Preparation of Compounds 56 and 57

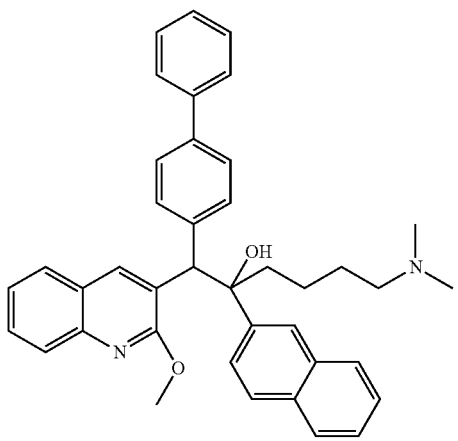

Compound 56 (dia A)
Compound 57 (dia B)

A mixture of compound 62 (mixture of dia A and B) (0.00103 mol), phenyl-boronic acid (0.00154 mol) and Pd(PPh$_3$)$_2$Cl$_2$ (0.00005 mol) in dimethoxyethane (1.5 ml), MeOH (1.5 ml) and Na$_2$CO$_3$ 2M (0.77 ml) was stirred in a microwave oven at 90° C. for 2 times 9 minutes (P=300 W). The mixture was then cooled to room temperature and poured out into H$_2$O. CH$_2$Cl$_2$ was added and the mixture was filtered over a short pad of celite. The filtrate was decanted and the organic layer was dried (MgSO$_4$), filtered and the solvent was evaporated. The residue was purified by column chromatography over silica gel (eluent: CH$_2$Cl$_2$/CH$_3$OH: 5:1; 15-40 μm). Two fractions were collected and the solvent was evaporated. Yield: 30% of compound 56 and 28% of compound 57.

A fraction of compound 57 was separated by chiral column chromatography over silica gel (SFC, chiralpack AD, eluent: CO$_2$/MeOH: 80/20). Two fractions were collected and the solvent was evaporated to obtain compound 175 (B1, 10%) and compound 176 (B2, 10%).

Example B12

Preparation of Compounds 58 and 59

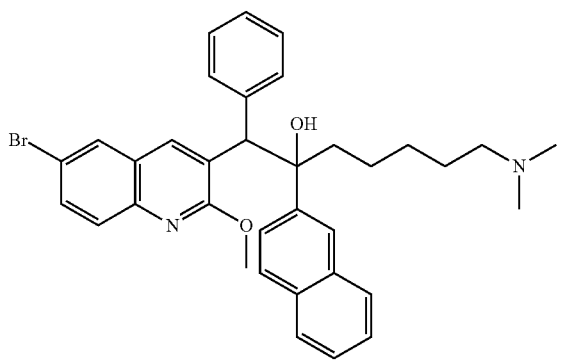

Compound 58 (dia A)
Compound 59 (dia B)

n-BuLi (4.86 mmol) was added dropwise at −20° C. to a solution of diisopropylamine (4.86 mmol) in THF (10 ml) under N2 flow. The mixture was stirred at −20° C. for 20 minutes and then cooled to −70° C. A solution of intermediate 19 (0.00405 mol) in THF (11 ml) was added. The mixture was stirred at −70° C. for 1 hour and then a solution of intermediate 3b in THF (10 ml) was added. The mixture was stirred at −70° C. for 30 minutes. Water was added and the mixture was extracted with EtOAc. The organic layer was separated, washed with brine, dried over MgSO$_4$, filtered and the solvent was evaporated. The residue (2.7 g) was purified by column chromatography over silica gel (eluent: CH$_2$Cl$_2$/CH$_3$OH/ NH$_4$OH 92/8/0.2, SiO$_2$ 15-40 μm then CH$_2$Cl$_2$/CH$_3$OH/ NH$_4$OH 94/6/0.3 kromasil Si 10 μm). Two fractions were collected and the solvent was evaporated. Yield: 0.25 g of compound 58 (10%) (fraction 1, dia A) and 0.19 g of fraction 2 (8%) (dia B). Fraction 2 was crystallized from DIPE. Yield: 0.09 g of compound 59 (4%) (dia B, mp. 132° C.).

Example B13a

Preparation of Compound 67

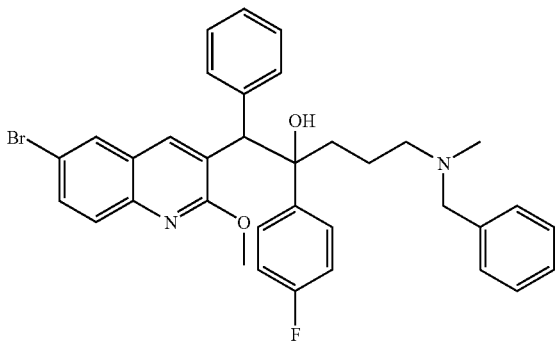

Compound 67 (mixture of dia A and dia B)

A solution of intermediate 19 (4.54 g, 0.0138 mol) in THF (30 ml) was added slowly at −70° C. under N$_2$ flow to a solution of Lithium diisopropylamide (12.7 ml, 0.0166 mol) in THF (19 ml). The mixture was stirred at −70° C. for 90 minutes. A solution of intermediate 3d (0.0166 mol) in THF (45 ml) was added slowly. The mixture was stirred at −70° C. for 3 hours, hydrolyzed at −30° C. with ice water, and extracted with EtOAc. The organic layer was separated, dried over MgSO$_4$, filtered, and the solvent was evaporated. The residue (9 g) was purified by column chromatography over silica gel (eluent: CH$_2$Cl$_2$/CH$_3$OH; 99/1; 15-40 μm). The pure fractions were collected and the solvent was evaporated. Yield: 4.9 g of compound 67 (60%) (mixture of diastereoisomers A and B).

Example B13b

Preparation of Compound 54

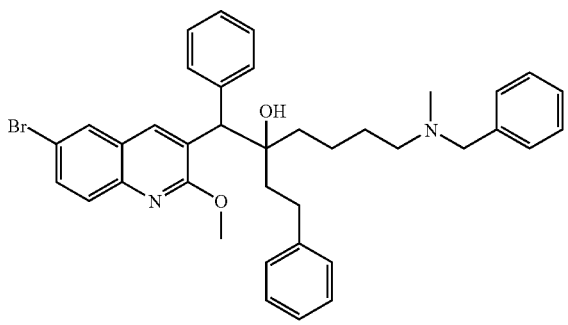

Compound 54 (mixture of dia A and dia B)

n-BuLi (15.6 ml, 0.025 mol. 1.2 equiv) was added dropwise at −20° C. to a solution of diisopropylamine (3.5 ml, 0.025 mol, 1.2 equiv) in THF (40 ml) under $N_2$ flow. The mixture was stirred at −20° C. for 20 minutes, and then cooled to −70° C. A solution of intermediate 19 (6.8 g, 0.021 mol) in THF (70 ml) was added. The mixture was stirred at −70° C. for 2 hours, and then a solution of intermediate 8 (7.86 g, 0.025 mol, 1.2 equiv) in THF (70 ml) was added. The mixture was stirred at −70° C. for 2 hours. Water was added and the mixture was extracted with EtOAc. The organic layer was separated, washed with brine, dried over $MgSO_4$, filtered and the solvent was evaporated. The residue (21 g) was purified by column chromatography over silica gel (eluent: $CH_2Cl_2$/isopropanol/$NH_4OH$: 98/2/0.1; 15-40 μm) to give rise to compound 54 (2.5 g) (mixture of dia A and dia B).

Example B14a

Preparation of Compounds 68 and 69

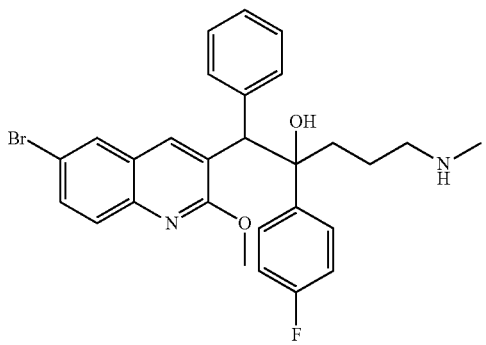

Compound 68 (dia A)
Compound 69 (dia B)

1-chloroethyl chloroformate (0.86 ml, 0.008 mol) was added at room temperature to a solution of compound 67 (4.9 g, 0.008 mol) in dichloroethane (58 ml). The mixture was stirred at 80° C. for 1 hour, then brought to room temperature and evaporated till dryness. Methanol (58 ml) was added. The mixture was stirred and refluxed for 30 minutes, then brought to room temperature and evaporated till dryness. The residue (4.5 g) was purified by column chromatography over silica gel (eluent: $CH_2Cl$/$CH_3OH$/$NH_4OH$; 97/3/0.5; 15-40 μm). Two fractions were collected and the solvent was evaporated. Each fraction was crystallized from diisopropyether/diethyl ether. Yield: 0.72 g of compound 68 as a white solid (18%) (diastereoisomer A, melting point 188° C.) and 1.1 g of compound 69 as a white solid (27%) (diastereoisomer B, melting point 204° C.).

Example B14b

Preparation of Compounds 70 and 71

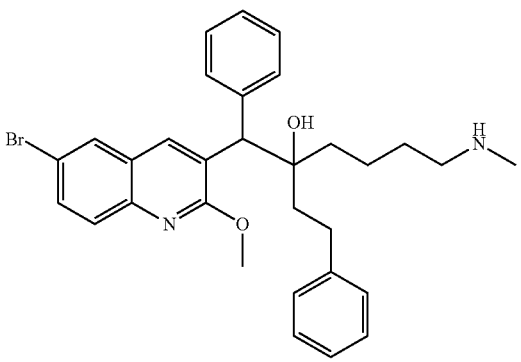

Compound 70 (dia A)
Compound 71 (dia B)

1-chloroethyl chloroformate (0.42 ml, 0.0039 mol, 1 equiv) was added at room temperature to a mixture of compound 54 (2.5 g, 0.0039 mol) in 1,2-dichloroethane (29 ml). The mixture was stirred at 80° C. for 1 hour, and then the solvent was evaporated. MeOH (29 ml) was added to the residue and the mixture was refluxed for 1 hour. The solvent was evaporated. The residue (4.6 g) was purified by column chromatography over silica gel (eluent: $CH_2Cl_2$/MeOH/$NH_4OH$ 93/7/0.5; kromasil 5 μm) to afford two fractions. Yield: 0.22 g of compound 70 (11%) (fraction 1, dia A) and 0.18 g of compound 71 (9%) (fraction 2, dia B).

Example B 15

Preparation of Compounds 72 and 73

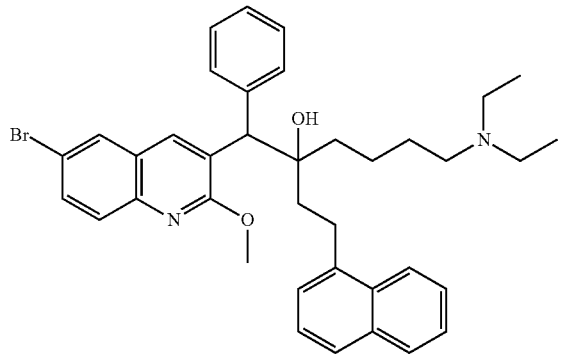

Compound 72 (dia A)
Compound 73 (dia B)

n-BuLi 1.6M in hexane (0.0034 mol) was added dropwise at −20° C. to a solution of diisopropylamine (0.0034 mol) in THF (7 ml) under N₂ flow. The mixture was cooled to −70° C. A solution of intermediate 19 (0.0028 mol) in THF (10 ml) was added. The mixture was stirred at −70° C. for 1 hour and 30 minutes. A solution of intermediate 9 (0.0034 mol) in THF (11 ml) was added. The mixture was stirred at −70° C. for 3 hours, then poured out on ice at −30° C. and extracted with EtOAc. The organic layer was washed with saturated NaCl, dried (MgSO₄), filtered and the solvent was evaporated. The residue was purified by column chromatography over silica gel (eluent: CH₂Cl₂/CH₃OH/NH₄OH 95/5/0.2; 15-40 μm). Two fractions were collected and the solvent was evaporated. Each fraction was crystallized separately from DIPE. The precipitate was filtered off and dried. Yield: 0.2 g of compound 72 (11%) (fraction 1, dia A, mp. 138° C.) and 0.07 g of compound 73 (4%) (fraction 2, dia B, mp 116° C.).

Example B16

Preparation of Compounds 179 and 180

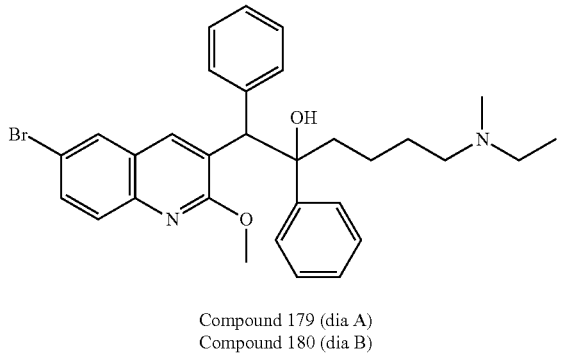 [SMILES: CCN(C)CCCCC(O)(c1ccccc1)C(c1ccccc1)c1cc2cc(Br)ccc2nc1OC]

Compound 179 (dia A)
Compound 180 (dia B)

A mixture of intermediate 22 (0.5 g, 9.5 mmol) and N-methylethyl amine (0.41 ml, 48 mmol 5 equiv) was heated to 135° C. in a microwave (Biotage Initiator 60 exp) for 12 min. The mixture was cooled down to room temperature, water was added. Extraction with EtOAc, followed by purification by column chromatography over silica gel (eluent: CH₂Cl₂/MeOH/NH₄OH, 95/5/0.1; kromasil 5 μm: 95/5; 10 μm). Two fractions were obtained: F1: 0.06 g of compound 179 (dia A) (11%) and F2: 0.09 g of compound 180 (dia B) (16%).

Example B17

Preparation of Compounds 181 and 182

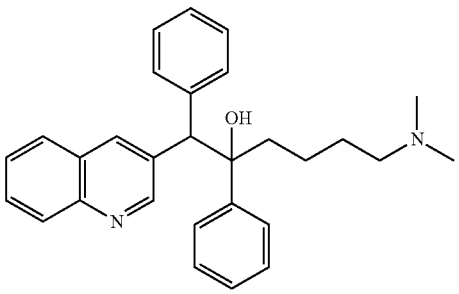

Compound 181 (dia A)
Compound 182 (dia B)

A mixture of intermediate 26 (0.068 mmol), dimethylamine (0.069 mmol), Rh(cod)₂BF₄ (0.005 mmol) Ir(cod)₂BF₄ (0.01 mmol), Xantphos (0.02 mmol) in THF (15 ml) and MeOH (15 ml) under CO (7 atm) and H₂ (33 atm) are heated in an autoclave at 100° C. for 48 hours. After cooling, the reaction mixture is concentrated in vacuo. The residue is dissolved in CH₂Cl₂ and the solution is filtered through a Silica SCX column (IST 530-0100-C) to catch the compound. The column is washed with CH₂Cl₂/MeOH: 90/10 and the product is released with CH₂Cl₂/NH₃ in MeOH: 70/30. The solution is concentrated in vacuo and purified by HPLC on RP with NH₄HCO₃-buffer. Yield: 2 isomers compound 181 (dia A) and compound 182 (dia B).

Tables 1 to 8 list compounds of formula (Ia) or (Ib) which were prepared according to one of the above Examples (Ex. No.) (whenever Ex. Nr. B2 or B3 is indicated it means the compound is synthesized according to the analogue protocols B2a to B2k or B3a-B3b)

TABLE 1

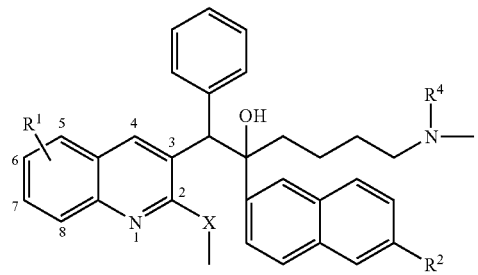

| Comp. nr. | Ex. nr. | R¹ | R² | R⁴ | X | Physical data and stereochemistry |
|---|---|---|---|---|---|---|
| 74 | B9 | 6-Br | H | H | O | (A) |
| 75 | B9 | 6-Br | H | H | O | (B); 153° C. |
| 76 | B2 | 6-Br | H | benzyl | O | (B); 138° C. |
| 34 | B5a | H | OCH₃ | CH₃ | O | (B); 179° C. |
| 24 | B2i | 6-Br | H | CH₃ | O | (A1); 101° C.; $[\alpha]_D^{20} = +74.27°$ (c = 0.3945 w/v % in DMF) |
| 25 | B2i | 6-Br | H | CH₃ | O | (A2); 96° C.; $[\alpha]_D^{20} = −72.4°$ (c = 0.337 w/v % in DMF) |

TABLE 1-continued

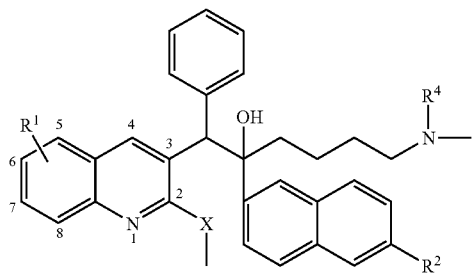

| Comp. nr. | Ex. nr. | R¹ | R² | R⁴ | X | Physical data and stereochemistry |
|---|---|---|---|---|---|---|
| 23 | B2i | 6-Br | H | CH₃ | O | (B2); 169° C.; $[\alpha]_D^{20} = -61.42°$ (c = 0.4705 w/v % in DMF) |
| 4 | B1 | 6-Br | H | CH₃ | S | (B); 178° C. |
| 5 | B2a | 6-Br | OCH₃ | CH₃ | O | (A); 96° C. |
| 6 | B2a | 6-Br | OCH₃ | CH₃ | O | (B); 164° C. |
| 27 | B3a | 5-Br | OCH₃ | CH₃ | O | (B); 180° C. |
| 31 | B4a | 7-Br | OCH₃ | CH₃ | O | (B); 174° C. |
| 7 | B2a | 6-Br | Br | CH₃ | O | (A); 100° C. |
| 35 | B5a | H | OCH₃ | CH₃ | O | (A); 150° C. |
| 39 | B6 | 6-[2-furanyl] | H | CH₃ | O | (A); 108° C. |
| 38 | B6 | 6-[2-furanyl] | H | CH₃ | O | (B); 182° C. |
| 8 | B2a | 6-Br | Br | CH₃ | O | (B); 169° C. |
| 22 | B2i | 6-Br | H | CH₃ | O | (B1); 166° C.; $[\alpha]_D^{20} = +64.46°$ (c = 0.4995 w/v % in DMF) |
| 40 | B7 | 6-phenyl | H | CH₃ | O | (A) |
| 41 | B7 | 6-phenyl | H | CH₃ | O | (B); 90° C. |
| 26 | B3a | 5-Br | OCH₃ | CH₃ | O | (A); 164° C. |
| 3 | B1 | 6-Br | H | CH₃ | S | (A); 163° C. |
| 30 | B4a | 7-Br | OCH₃ | CH₃ | O | (A); 160° C. |
| 36 | B5b | H | H | CH₃ | O | (A); 105° C. |
| 37 | B5c | H | H | CH₃ | O | (B) |
| 33 | B4b | 7-Br | H | CH₃ | O | (B); 198° C. |
| 32 | B4b | 7-Br | H | CH₃ | O | (A) |
| 28 | B3b | 5-Br | H | CH₃ | O | (A); 170° C. |
| 29 | B3b | 5-Br | H | CH₃ | O | (B); 173° C. |
| 17 | B2f | 6-Br | H | CH₃ | O | (A); 170° C. |
| 18 | B2f | 6-Br | H | CH₃ | O | (B); 145° C. |
| 77 | B3 | 7-CH₃ | H | CH₃ | O | (A2) |
| 78 | B3 | 7-CH₃ | H | CH₃ | O | (A1) |
| 79 | B3 | 6-Cl | H | CH₃ | O | (A) |
| 55 | B10 | 6-CH₂OH | H | CH₃ | O | (B); 174° C. |
| 80 | B3 | 7-Br, 8-CH₃ | H | CH₃ | O | (A); 190.1° C. |
| 81 | B3 | 7-Br, 8-CH₃ | H | CH₃ | O | (B); 195.1° C. |

TABLE 2

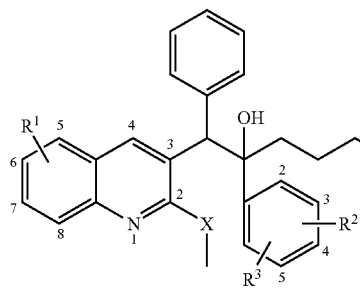

| Comp. nr. | Ex. nr. | R¹ | R² | R³ | X | Physical data and stereochemistry |
|---|---|---|---|---|---|---|
| 2 | B1 | 6-Br | H | H | S | (B); 155° C. |
| 1 | B1 | 6-Br | H | H | S | (A) |
| 43 | B8 | 6-[3-pyridinyl] | H | H | O | (A); 192° C. |
| 42 | B8 | 6-[3-pyridinyl] | H | H | O | (B); 203° C. |
| 82 | B6 | 6-[2-furanyl] | H | H | O | (A) |
| 83 | B6 | 6-[2-furanyl] | H | H | O | (B) |
| 84 | B2 | 6-Br | 3-F | H | O | (A); 145° C. |
| 11 | B2c | 6-Br | 3-F | 5-F | O | (A); 157° C. |
| 12 | B2c | 6-Br | 3-F | 5-F | O | (B); 175° C. |
| 14 | B2d | 6-Br | 2-F | 5-F | O | (B); 157° C. |
| 13 | B2d | 6-Br | 2-F | 5-F | O | (A); 166° C. |
| 20 | B2h | 6-Br | H | H | O | (A); 130° C. |
| 21 | B2h | 6-Br | H | H | O | (B); 170° C. |

TABLE 3

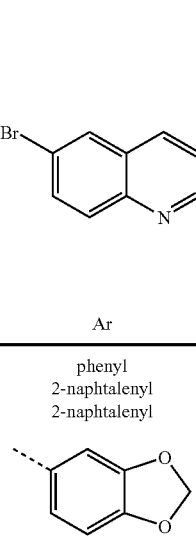

| Comp. nr. | Ex. nr. | X | Ar | L | Physical data and stereochemistry |
|---|---|---|---|---|---|
| 53 | B9 | O | phenyl | NH(CH$_3$) | (A); 121° C. |
| 85 | B2 | O | 2-naphtalenyl | N(CH$_2$CH$_3$)$_2$ | (A); 131° C. |
| 86 | B2 | O | 2-naphtalenyl | N(CH$_2$CH$_3$)$_2$ | (B) |
| 9 | B2b | O | 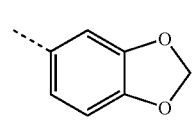 | N(CH$_3$)$_2$ | (A); 98° C. |
| 10 | B2b | O | 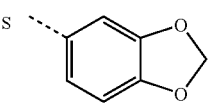 | N(CH$_3$)$_2$ | (B); 110° C. |
| 15 | B2e | O | 3-pyridinyl | N(CH$_3$)$_2$ | (A); 150° C. |
| 16 | B2e | O | 3-pyridinyl | N(CH$_3$)$_2$ | (B); 98° C. |
| 19 | B2g | O | 1-naphthalenyl | N(CH$_3$)$_2$ | (A) |
| 87 | B1 | S | 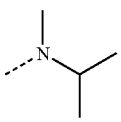 | N(CH$_3$)$_2$ | (B); 172° C. |
| 88 | B2 | O | phenyl | 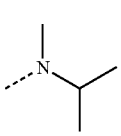 | (A1); [α]$_D^{20}$ = +58.56° (c = 0.5225 w/v % in DMF) |
| 89 | B2 | O | phenyl | 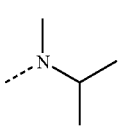 | (A2); [α]$_D^{20}$ = −59.44° (c = 0.5165 w/v % in DMF) |
| 90 | B2 | O | phenyl | 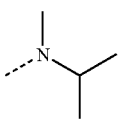 | (B1); 128° C.; [α]$_D^{20}$ = +153.79° (c = 0.5345 w/v % in DMF) |
| 91 | B2 | O | phenyl | 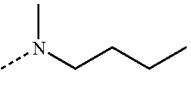 | (B2); 127° C.; [α]$_D^{20}$ = −153.54° (c = 0.5015 w/v % in DMF) |
| 92 | B2 | O | phenyl | 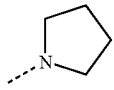 | (A) |
| 93 | B2 | O | phenyl | 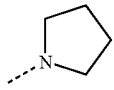 | (A) |

TABLE 3-continued

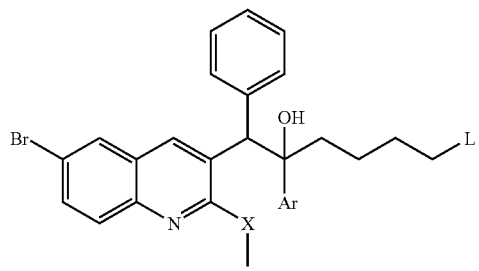

| Comp. nr. | Ex. nr. | X | Ar | L | Physical data and stereochemistry |
|---|---|---|---|---|---|
| 94 | B2 | O | phenyl | piperidin-1-yl | (A); 129° C. |
| 95 | B2 | O | phenyl | piperidin-1-yl | (B); 166° C. |
| 96 | B2 | O | 2-naphthalenyl | piperidin-1-yl | (B) |
| 97 | B2 | O | 4-methoxyphenyl | piperidin-1-yl | (A) |
| 98 | B2 | O | phenyl | piperidin-1-yl | (A1); $[\alpha]_D^{20} = +60.25°$ (c = 0.649 w/v % in DMF) |
| 99 | B2 | O | phenyl | piperidin-1-yl | (A2); $[\alpha]_D^{20} = -57.81°$ (c = 0.5795 w/v % in DMF) |
| 100 | B2 | O | phenyl | piperidin-1-yl | (B1); 167° C.; $[\alpha]_D^{20} = +151.38°$ (c = 0.652 w/v % in DMF) |
| 101 | B2 | O | phenyl | piperidin-1-yl | (B2); 168° C.; $[\alpha]_D^{20} = -151.39°$ (c = 0.7015 w/v % in DMF) |
| 102 | B2 | O | 2-naphthalenyl | 4-methylpiperidin-1-yl | (A) |
| 103 | B2 | O | 2-naphthalenyl | 4-methylpiperidin-1-yl | (B) |
| 104 | B9 | O | phenyl | piperazin-1-yl | (A) |

TABLE 3-continued

| Comp. nr. | Ex. nr. | X | Ar | L | Physical data and stereochemistry |
|---|---|---|---|---|---|
| 105 | B9 | O | phenyl | piperazine (N-linked, NH) | (B) |
| 106 | B21 | O | 2-naphthalenyl | piperazine (N-linked, NH) | (A) |
| 107 | B21 | O | 2-naphthalenyl | piperazine (N-linked, NH) | (B) |
| 108 | B2 | O | phenyl | 4-methylpiperazin-1-yl | (A1) |
| 109 | B2 | O | phenyl | 4-methylpiperazin-1-yl | (A2) |
| 110 | B2 | O | phenyl | 4-methylpiperazin-1-yl | (B1) |
| 111 | B2 | O | phenyl | 4-methylpiperazin-1-yl | (B2) |
| 112 | B2 | O | 2-naphthalenyl | 4-methylpiperazin-1-yl | (B1) |
| 113 | B2 | O | 2-naphthalenyl | 4-methylpiperazin-1-yl | (A1) |
| 114 | B2 | O | phenyl | morpholin-4-yl | (A1) |
| 115 | B2 | O | phenyl | morpholin-4-yl | (A2) |

TABLE 3-continued

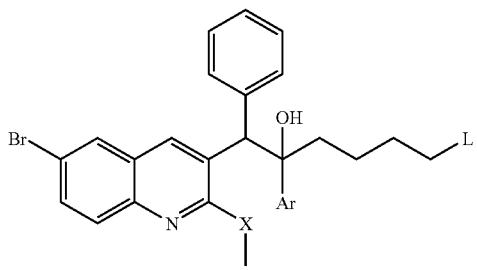

| Comp. nr. | Ex. nr. | X | Ar | L | Physical data and stereochemistry |
|---|---|---|---|---|---|
| 116 | B2 | O | phenyl | 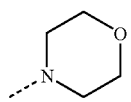 | (B2) |
| 60 | B2.j | O | phenyl | 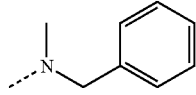 | (A) |
| 61 | B2.j | O | phenyl | 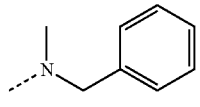 | (B) |
| 179 | B16 | O | phenyl | 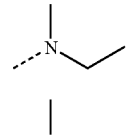 | (A) |
| 180 | B16 | O | phenyl | 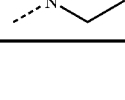 | (B) |

TABLE 4

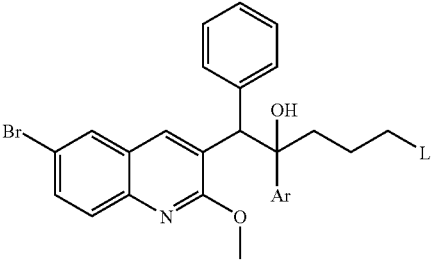

| Comp. nr. | Ex. nr. | Ar | L | Physical data and stereochemistry |
|---|---|---|---|---|
| 68 | B14.a | 4-fluorophenyl | NH(CH$_3$) | (A); 188° C. |
| 69 | B14.a | 4-fluorophenyl | NH(CH$_3$) | (B); 204° C. |
| 67 | B13.a | 4-fluorophenyl | 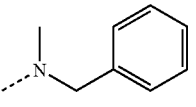 | (A + B) |
| 44 | * | phenyl | N(CH$_3$)$_2$ | (A); 150° C. |
| 45 | * | phenyl | N(CH$_3$)$_2$ | (B); 220° C. |
| 46 | ** | 2-naphthalenyl | N(CH$_3$)$_2$ | (A); 229° C. |
| 47 | ** | 2-naphthalenyl | N(CH$_3$)$_2$ | (B); 214° C. |
| 48 | ** | 2-naphthalenyl | pyrrolidinyl | (A); 227° C. |
| 49 | ** | 2-naphthalenyl | pyrrolidinyl | (B); 222° C. |
| 50 | ** | 1-naphthalenyl | N(CH$_3$)$_2$ | (A); 187° C. |

TABLE 4-continued

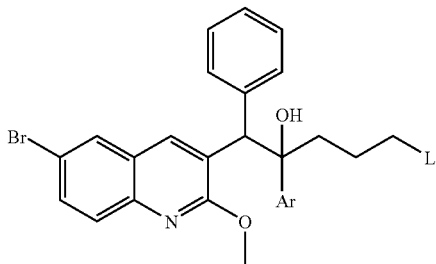

| Comp. nr. | Ex. nr. | Ar | L | Physical data and stereochemistry |
|---|---|---|---|---|
| 51 | ** | 2-naphthalenyl | N(CH₂CH₃)₂ | (A); 90° C. |
| 52 | ** | 2-naphthalenyl | N(CH₂CH₃)₂ | (B); 202° C. |

*These compounds were prepared as described in WO2004/011436 according to Example B1.
**These compounds were prepared as described in WO2004/011436 according to Example B7.

TABLE 5

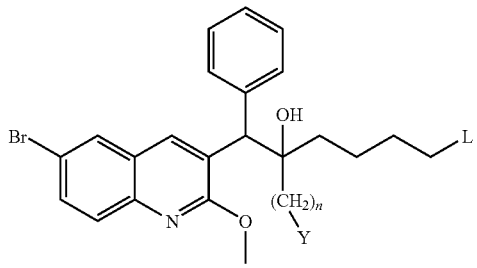

| Comp. nr. | Ex. nr. | n | Y | L | Physical data, salt and stereochemistry |
|---|---|---|---|---|---|
| 117 | B15 | 1 | isopropyl | N(CH₃)₂ | (A); 122° C. |
| 118 | B15 | 1 | isopropyl | N(CH₃)₂ | (B); 112° C. |
| 119 | B15 | 2 | isopropyl | N(CH₃)₂ | (A); 127° C. |
| 120 | B15 | 2 | isopropyl | N(CH₃)₂ | (B); 116° C. |
| 121 | B15 | 1 | isopropyl | piperidinyl | (A); 107° C. |
| 122 | B15 | 1 | isopropyl | piperidinyl | (B); 118° C. |
| 123 | B15 | 2 | isopropyl | piperidinyl | (A); 104° C. |
| 124 | B15 | 2 | isopropyl | piperidinyl | (B); 100° C. |
| 125 | B15 | 2 | cyclohexyl | 4-methylpiperazinyl | (A); 118° C. |

TABLE 5-continued

| Comp. nr. | Ex. nr. | n | Y | L | Physical data, salt and stereochemistry |
|---|---|---|---|---|---|
| 126 | B15 | 2 | cyclohexyl | 4-methylpiperazin-1-yl | (B) |
| 127 | B15 | 1 | phenyl | N(CH$_3$)$_2$ | (A) |
| 128 | B15 | 1 | phenyl | N(CH$_3$)$_2$ | (B); 122° C. |
| 70 | B14.b | 2 | phenyl | NH(CH$_3$) | (A); 130° C. |
| 71 | B14.b | 2 | phenyl | NH(CH$_3$) | (B); 140° C. |
| 54 | B13.b | 2 | phenyl | N(CH$_3$)(CH$_2$phenyl) | (A + B) |
| 129 | B15 | 2 | furan-2-yl | N(CH$_3$)$_2$ | (A); 96° C. |
| 130 | B15 | 2 | furan-2-yl | N(CH$_3$)$_2$ | (B); 158° C. |
| 131 | B15 | 2 | phenyl | N(CH$_3$)$_2$ | (A); 108° C. |
| 132 | B15 | 2 | phenyl | N(CH$_2$CH$_3$)$_2$ | (A) |
| 133 | B15 | 2 | phenyl | piperidin-1-yl | (A); 210° C.; HCl-salt |
| 134 | B15 | 2 | phenyl | piperidin-1-yl | (B) |
| 135 | B14.b | 2 | phenyl | piperazin-1-yl | (A) |
| 136 | B14.b | 2 | phenyl | piperazin-1-yl | (B) |
| 137 | B15 | 2 | phenyl | 4-methylpiperazin-1-yl | (A); 132° C. |

TABLE 5-continued

[Structure: 6-bromo-2-methoxyquinolin-3-yl connected to CH(phenyl)-C(OH)(CH2CH2CH2-L)-(CH2)n-Y]

| Comp. nr. | Ex. nr. | n | Y | L | Physical data, salt and stereochemistry |
|---|---|---|---|---|---|
| 138 | B15 | 2 | phenyl | 4-methylpiperazin-1-yl | (B); 146° C. |
| 139 | B15 | 2 | phenyl | 4-(dimethylamino)piperidin-1-yl | (A); 150° C. |
| 140 | B15 | 2 | phenyl | 4-(dimethylamino)piperidin-1-yl | (B); 146° C. |
| 141 | B15 | 2 | 4-methylphenyl | 4-methylpiperazin-1-yl | (A); 139° C. |
| 72 | B15 | 2 | 1-naphthalenyl | N(CH₂CH₃)₂ | (A); 138° C. |
| 73 | B15 | 2 | 1-naphthalenyl | N(CH₂CH₃)₂ | (B); 116° C. |
| 142 | B15 | 2 | 1-naphthalenyl | 4-methylpiperazin-1-yl | (A); 142° C. |
| 143 | B15 | 2 | 1-naphthalenyl | 4-methylpiperazin-1-yl | (B); 110° C. |
| 144 | B15 | 3 | phenyl | N(CH₃)₂ | (A); 136° C. |
| 145 | B15 | 3 | phenyl | N(CH₃)₂ | (B); 144° C. |
| 146 | B15 | 3 | phenyl | piperidin-1-yl | (A) |
| 147 | B15 | 4 | phenyl | N(CH₃)₂ | (B); 112° C. |
| 148 | B15 | 4 | phenyl | piperidin-1-yl | (A); 180° C. |
| 149 | B15 | 4 | phenyl | piperidin-1-yl | (B); 110° C. |

TABLE 6

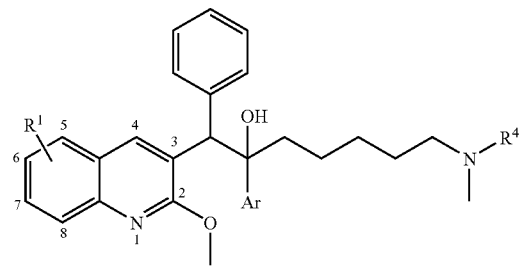

| Comp. nr. | Ex. nr. | R¹ | R⁴ | Ar | Physical data salt/melting points and stereochemistry |
|---|---|---|---|---|---|
| 150 | B9 | 6-CH₃ | H | phenyl | (A) |
| 151 | B9 | 6-CH₃ | H | phenyl | (B); 172° C. |
| 152 | B12 | 6-CH₃ | CH₃ | phenyl | (A) |
| 153 | B12 | 6-CH₃ | CH₃ | phenyl | (B); 123° C. |
| 154 | B12 | 6-Br | CH₃ | phenyl | (A); 125° C. |

TABLE 6-continued

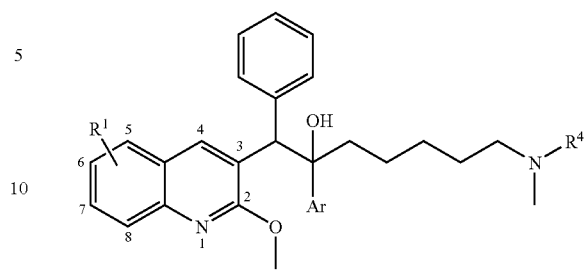

| Comp. nr. | Ex. nr. | R¹ | R⁴ | Ar | Physical data salt/melting points and stereochemistry |
|---|---|---|---|---|---|
| 155 | B12 | 6-Br | CH₃ | phenyl | (B); 140° C. |
| 58 | B12 | 6-Br | CH₃ | 2-naphthalenyl | (A) |
| 59 | B12 | 6-Br | CH₃ | 2-naphthalenyl | (B); 132° C. |

TABLE 7

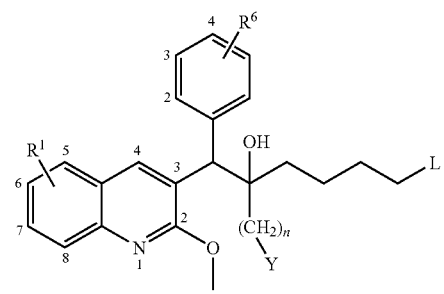

| Comp. nr. | Ex. nr. | n | R¹ | R⁶ | Y | L | Physical data and stereochemistry |
|---|---|---|---|---|---|---|---|
| 156 | B11 | 0 | H | 4-(2-methoxyphenyl) | 2-naphthalenyl | N(CH₃)₂ | (A) |
| 157 | B3 | 0 | 6-Br | 4-OCH₃ | 2-naphthalenyl | N(CH₃)₂ | (A) |
| 158 | B3 | 0 | 6-Br | 4-OCH₃ | 2-naphthalenyl | N(CH₃)₂ | (B2) |
| 62 | B2.k | 0 | H | 4-Br | 2-naphthalenyl | N(CH₃)₂ | (A + B) |
| 64 | B2.k | 0 | H | 4-Br | 2-naphthalenyl | N(CH₃)₂ | (A2) |
| 63 | B2.k | 0 | H | 4-Br | 2-naphthalenyl | N(CH₃)₂ | (A1) |
| 65 | B2.k | 0 | H | 4-Br | 2-naphthalenyl | N(CH₃)₂ | (B1) |
| 66 | B2.k | 0 | H | 4-Br | 2-naphthalenyl | N(CH₃)₂ | (B2) |
| 159 | B2k | 0 | H | 3-Br | 2-naphthalenyl | N(CH₃)₂ | (B1) |
| 160 | B2k | 0 | H | 3-Br | 2-naphthalenyl | N(CH₃)₂ | (B2) |
| 161 | B2k | 0 | H | 3-Br | 2-naphthalenyl | N(CH₃)₂ | (A1) |
| 162 | B2k | 0 | H | 3-Br | 2-naphthalenyl | N(CH₃)₂ | (A2) |
| 163 | B3 | 0 | 6-Br | 3-Cl | 2-naphthalenyl | N(CH₃)₂ | (B1) |
| 164 | B3 | 0 | 6-Br | 4-Cl | 2-naphthalenyl | N(CH₃)₂ | (B2) |
| 165 | B3 | 0 | 6-Br | 4-OCH₃ | phenyl | piperidinyl | (A); 115° C. |
| 166 | B3 | 0 | 6-Br | 4-OCH₃ | phenyl | piperidinyl | (B); 163° C. |

TABLE 7-continued

| Comp. nr. | Ex. nr. | n | R¹ | R⁶ | Y | L | Physical data and stereochemistry |
|---|---|---|---|---|---|---|---|
| 167 | B3 | 0 | 6-Br | 4-OCH₃ | 4-methylphenyl | piperidinyl | (A) |
| 168 | B3 | 0 | 6-Br | 4-CH₃ | 4-methoxyphenyl | piperidinyl | (A); 142° C. |
| 169 | B3 | 0 | 6-Br | 4-OCH₃ | 4-methoxyphenyl | piperidinyl | (A); 131° C. |
| 170 | B3 | 0 | 6-Br | 4-Cl | phenyl | piperidinyl | (A) |
| 171 | B3 | 0 | 6-Br | 4-Cl | 4-methylphenyl | piperidinyl | (A); 158° C. |
| 172 | B3 | 0 | 6-Br | 3-Cl, 4-Cl | phenyl | piperidinyl | (A); 159° C. |
| 173 | B3 | 0 | 6-Br | 3-Cl, 4-Cl | phenyl | piperidinyl | (B); 147° C. |
| 174 | B15 | 2 | 6-Br | 4-Cl | cyclohexyl | 4-methylpiperazinyl | (B) |
| 56 | B11 | 0 | H | 4-phenyl | 2-naphthalenyl | N(CH₃)₂ | (A) |
| 57 | B11 | 0 | H | 4-phenyl | 2-naphthalenyl | N(CH₃)₂ | (B) |
| 175 | B11 | 0 | H | 4-phenyl | 2-naphthalenyl | N(CH₃)₂ | (B1) |
| 176 | B11 | 0 | H | 4-phenyl | 2-naphthalenyl | N(CH₃)₂ | (B2) |

TABLE 8

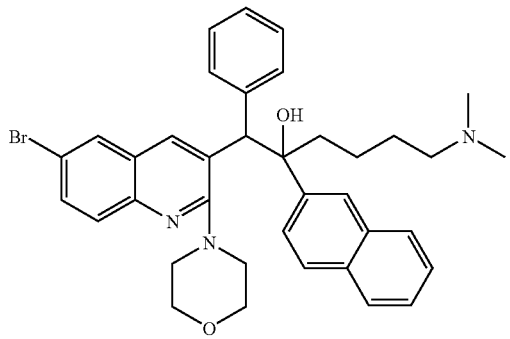 [SMILES: CN(C)CCCCC(O)(c1ccc2ccccc2c1)C(c1ccccc1)c1cc2cc(Br)ccc2nc1N1CCOCC1]

| Comp. nr. | Ex. nr. | Physical data and stereochemisty |
|---|---|---|
| 177 | B1 | (A) |
| 178 | B1 | (B); 137° C. |

Analytical Part

The mass of some compounds of the present invention was recorded with LCMS (liquid chromatography mass spectrometry). The methods used are described below and the Rt and the parent peaks are listed in Table 9 below.

General Procedure A

The HPLC gradient was supplied by an Alliance HT 2795 (Waters) system consisting of a quaternary pump with degasser, an autosampler, and DAD detector. Flow from the column was split to the MS detector. MS detectors were configured with an electrospray ionization source. The capillary needle voltage was 3 kV and the source temperature was maintained at 100° C. on the LCT (Time of Flight-Z-spray mass spectrometer from Waters) and 3.15 kV and 1110° C. on the ZQ (simple quadripole-Z-spray mass spectrometer from Waters). Nitrogen was used as the nebulizer gas. Data acquisition was performed with a Waters-Micromass MassLynx-Openlynx data system.

General Procedure B

The HPLC gradient was supplied by an Alliance HT 2790 (Waters) system consisting of a quaternary pump with degasser, an autosampler, a column oven (set at 40° C.) and DAD detector. Flow from the column was split to the MS detector. MS detectors were configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS-Method 1

In addition to general procedure A: Reversed phase HPLC was carried out on an Kromasil C18 column (5 μm, 4.6×150 mm) with a flow rate of 1.0 ml/min. Three mobile phases (mobile phase A: 100% 7 mM ammonium acetate; mobile phase B: 100% acetonitrile; mobile phase C, 0.2% formic acid+99.8% ultra-pure Water) were employed to run a gradient condition from 30% A, 40% B and 30% C (hold for 1 minute) to 100% B in 4 minutes, 100% B for 5 minutes and reequilibrated with initial conditions for 3 minutes. An injection volume of 5 μl was used. Cone voltage was 20 V for positive ionization mode. Mass spectra were acquired by scanning from 100 to 900 in 0.8 seconds using an interscan delay of 0.08 seconds.

LCMS-Method 2

In addition to general procedure A: Reversed phase HPLC was carried out on a Sunfire C18 column (3.5 μm, 4.6×100 mm) with an initial flow rate of 0.8 ml/min. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

LCMS-Method 3

In addition to general procedure A: Reversed phase HPLC was carried out on a Sunfire C18 column (3.5 μm, 4.6×100 mm) with an initial flow rate of 0.8 ml/min. Two mobile phases (mobile phase A: 25% 6.5 mM ammonium acetate+50% acetonitrile+25% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes). An injection volume of 10 μl was used. Cone voltage was 20 V for positive and negative ionization mode. Mass spectra were acquired by scanning from 100 to 1000 in 0.4 seconds using an interscan delay of 0.3 seconds.

LCMS-Method 4

In addition to general procedure B: Reversed phase HPLC was carried out on an Xterra MS C18 column (3.5 mm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 μl was used. Cone voltage was 10 V for positive ionization mode and 20 V for negative ionization mode.

LCMS-Method 5

In addition to general procedure A: Reversed phase HPLC was carried out on an Kromasil C18 column (5 μm, 4.6×150 mm) with a flow rate of 1.0 ml/min. Three mobile phases (mobile phase A: 100% 7 mM ammonium acetate; mobile phase B: 100% acetonitrile; mobile phase C: 0.2% formic acid+99.8% ultra-pure Water) were employed to nm a gradient condition from 30% A, 40% B and 30% C (hold for 1 minute) to 100% B in 4 minutes, 100% B for 5 minutes and reequilibrated with initial conditions for 3 minutes. An injection volume of 5 μl was used. Cone voltage was 20 V for positive and negative ionization mode. Mass spectra were acquired by scanning from 100 to 900 in 0.8 seconds using an interscan delay of 0.08 seconds.

LCMS-Method 6

In addition to general procedure B: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 6.80 minutes.

LCMS-Method 7

In addition to general procedure B: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 9.3 minutes.

TABLE 9

LCMS results (retention time Rt (minutes) and molecular weight as the MH+)

| Compound No | Rt | LCMS parent peak (MH+) | LCMS method |
|---|---|---|---|
| 1 | 6.40 | 549 | 1 |
| 19 | 6.17 | 583 | 1 |
| 37 | 5.37 | 505 | 1 |
| 33 | 6.58 | 583 | 1 |
| 28 | 6.4 | 583 | 1 |
| 29 | 6.23 | 583 | 1 |
| 15 | 4.02 | 534 | 2 |
| 16 | 4.09 | 534 | 2 |
| 32 | 3.87 | 583 | 3 |
| 40 | 4.46 | 581 | 3 |
| 74 | 6.26 | 569 | 1 |
| 77 | 10.16 | 519 | 4 |
| 78 | 10.19 | 519 | 4 |
| 79 | 4.175 | 540 | 7 |
| 82 | 3.67 | 521 | 3 |
| 83 | 3.27 | 521 | 3 |
| 86 | 4.35 | 611 | 3 |
| 88 | 5.74 | 561 | 5 |
| 89 | 5.74 | 561 | 5 |
| 92 | 3.41 | 577 | 6 |
| 93 | 4.396 | 560 | 7 |
| 96 | 3.43 | 625 | 6 |
| 97 | 5.08 | 603 | 2 |
| 98 | 5.05 | 573 | 2 |
| 99 | 5.07 | 573 | 2 |
| 102 | 8.28 | 637 | 4 |
| 103 | 8.25 | 637 | 4 |
| 104 | 5.9 | 574 | 1 |
| 105 | 5.7 | 574 | 1 |
| 106 | 2.84 | 624 | 3 |
| 107 | 2.65 | 624 | 3 |
| 108 | 9.29 | 588 | 4 |
| 109 | 9.29 | 588 | 4 |
| 110 | 9.1 | 588 | 4 |
| 111 | 9.1 | 588 | 4 |
| 112 | 9.54 | 638 | 4 |
| 113 | 9.58 | 638 | 4 |
| 114 | 9.24 | 575 | 4 |
| 115 | 9.26 | 575 | 4 |
| 116 | 9.07 | 575 | 4 |
| 61 | 4.45 | 610 | 7 |
| 126 | 4.25 | 622 | 3 |
| 127 | 5 | 547 | 2 |
| 132 | 6.57 | 589 | 1 |
| 134 | 4.22 | 601 | 3 |
| 135 | 6.1 | 602 | 1 |
| 136 | 6.38 | 602 | 1 |
| 146 | 5.32 | 615 | 2 |
| 150 | 6.26 | 533 | 1 |
| 152 | 5.73 | 483 | 1 |
| 58 | 5.31 | 597 | 2 |
| 156 | 4.39 | 611 | 7 |
| 157 | 4.219 | 614 | 7 |
| 158 | 5.3 | 613 | 4 |
| 64 | 10.58 | 583 | 4 |
| 63 | 10.59 | 583 | 4 |
| 65 | 10.21 | 583 | 4 |
| 66 | 10.21 | 583 | 4 |
| 159 | 10.12 | 583 | 4 |
| 160 | 10.15 | 583 | 4 |
| 161 | 10.43 | 583 | 4 |
| 162 | 10.4 | 583 | 4 |
| 163 | 8.32 | 617 | 4 |
| 164 | 8.41 | 617 | 4 |
| 167 | 5.05 | 617 | 2 |
| 170 | 5.35 | 607 | 2 |
| 174 | 5.8 | 656 | 2 |
| 56 | 4.331 | 581 | 7 |
| 57 | 4.389 | 581 | 7 |
| 175 | 10.62 | 581 | 4 |
| 176 | 10.61 | 581 | 4 |
| 177 | 3.3 | 638 | 3 |
| 60 | 4.7 | 611 | 7 |

Pharmacological Part

Preparation of Bacterial Suspensions for Susceptibility Testing:

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates and colony forming units (CFUs) were determined. In general, an inoculum level of approximately 100 CFUs was used for susceptibility testing.

Anti Bacterial Susceptibility Testing: $IC_{90}$ Determination Microtitre Plate Assay Flat-bottom, sterile 96-well plastic microtiter plates were filled with 180 μl of sterile deionized water, supplemented with 0.25% BSA. Subsequently, stock solutions (7.8× final test concentration) of compounds were added in 45 μl volumes in column 2. Serial five-fold dilutions (45 μl in 180 μl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 μl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 μl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The $IC_{90}$ (expressed in μg/ml) was defined as the 90% inhibitory concentration for bacterial growth. The results are shown in Table 10 below.

Agar Dilution Method.

$MIC_{99}$ values (the minimal concentration for obtaining 99% inhibition of bacterial growth) can be determined by performing the standard Agar dilution method according to NCCLS standards* wherein the media used includes Mueller-Hinton agar.

* Clinical laboratory standard institute. 2005. Methods for dilution Antimicrobial susceptibility tests for bacteria that grows Aerobically: approved standard- sixth edition Time Kill Assays Bactericidal or bacteriostatic activity of the compounds may be determined in a time kill assay using the broth microdilution method*. In a time kill assay on *Staphylococcus aureus* and methicillin resistant *S. aureus* (MRSA), the starting inoculum of *S. aurues* and MRSA is $10^6$ CPU/ml in Muller Hinton broth. The antibacterial compounds are used at the concentration of 0.1 to 10 times the MIC (i.e. $IC_{90}$ as determined in microtitre plate assay). Wells receiving no antibacterial agent constitute the culture growth control. The plates containing the microorganism and the test compounds are incubated at 37° C. After 0, 4, 24, and 48 hrs of incubation samples are removed for determination of viable counts by serial dilution ($10^{-1}$ to $10^{-6}$) in sterile PBS and plating (200 μl) on Mueller Hinton agar. The plates are incubated at 37° C. for 24 hours and the number of colonies are determined.

Killing curves can be constructed by plotting the $\log_{10}$CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating. No carryover effect is observed at the dilution of $10^{-2}$ used for plating. This results in limit of detection $5 \times 10^2$ CFU/ml or <2.7 log CFU/ml.

* Zurenko, G. E. et al. In vitro activities of U-100592 and U-100766, novel oxazolidinone antibacterial agents. *Antimicrob. Agents Chemother.* 40, 839-845 (1996).

Results

A time kill assay was performed with compound 18 and the control drug ciprofloxacin. Compound 18 demonstrated bactericidal activity on *S. aureus*, as did the control antibiotic ciprofloxacin. Bactericidal activities were observed at 1 and 10 times MIC90 (1 and 10×MIC equals to 12 and 120 µg/ml for compound 18). At 0.1 times the MIC, the treated samples followed the control in growth.

Also for MRSA, compound 18 demonstrated marked bactericidal activity as compared to ciprofloxacin for which these strains have developed resistance. MRSA is resistant not only to methicillin but also to fluoroquinolines like ciprofloxacin and as such no bactericidal effect was observed using this drug.

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hours at 37° C. (300 rpm). Measure $OD_{405}$ nm and calculate the CFU/ml. Dilute the cultures to $1 \times 10^6$ CFU/ml (final concentration for ATP measurement: $1 \times 10^5$ CFU/100 µl per well) and add test compound at 0.1 to 10 times the MIC (i.e. $IC_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 µl of the same sample. Add 100 µl Luciferase reagent to each well by using the injector system. Measure the luminescence for 1 sec.

TABLE 10

$IC_{90}$ values (µg/ml) determined according to the Microtitre plate assay.

| Comp. N°. | BSU 43639 | EFA 14506 | EFA 29212 | LMO 49594 | PAE 27853 | SMU 33402 | SPN 6305 | SPY 8668 | STA 25923 | STA 29213 | STA RMETH |
|---|---|---|---|---|---|---|---|---|---|---|---|
| 34 | | | 8.5 | | 2.7 | | 1.9 | 8.5 | | 3.8 | 10.7 |
| 2 | 43.7 | | 43.7 | 43.7 | 43.7 | | 21.9 | 8.7 | | 43.7 | 43.7 |
| 17 | 5.2 | | 5.2 | 5.8 | 2.3 | | 11.6 | 4.6 | 2.3 | 9.3 | 10.4 |
| 24 | 1.9 | | 1.9 | 1.9 | 1.9 | | 1.9 | 1.9 | 0.5 | 1.9 | 1.9 |
| 25 | 58.4 | | 4.1 | 9.3 | 1.9 | | 2.3 | 9.3 | 58.4 | 1.9 | 58.4 |
| 23 | 58.4 | | 4.1 | 36.8 | 1.9 | | 11.6 | 46.4 | 58.4 | 1.9 | 58.4 |
| 4 | 9.5 | | 9.5 | 9.5 | 1.9 | | 1.9 | 1.9 | | 1.9 | 9.5 |
| 5 | 1.9 | | 1.9 | 1.9 | 1.9 | | 2.4 | 1.5 | | 1.9 | 1.9 |
| 6 | 9.7 | | 9.7 | 9.7 | 9.7 | | 4.9 | 1.9 | | 4.3 | 9.7 |
| 27 | 48.7 | | 61.4 | 61.4 | 9.7 | | 61.4 | 48.7 | 61.4 | 1.9 | 61.4 |
| 31 | 9.7 | | 10.9 | 4.3 | 1.9 | | 9.7 | 4.3 | 12.2 | 1.9 | 4.3 |
| 7 | 10.5 | | 10.5 | 10.5 | 10.5 | | 2.4 | 10.5 | | 2.1 | 10.5 |
| 35 | | | 8.5 | | 8.5 | | 1.7 | 3.8 | | 2.1 | 10.7 |
| 39 | | | | | | | 3.6 | | | 2.0 | 4.5 |
| 38 | | | 7.2 | | 9.1 | | 11.4 | 9.1 | | 4.5 | 2.3 |
| 8 | | | 2.1 | | 5.3 | | 10.5 | 10.5 | | 2.4 | 2.6 |
| 20 | 10.6 | | 10.6 | 13.4 | 10.6 | | 2.1 | 4.2 | 10.6 | 10.6 | 10.6 |
| 22 | 58.4 | | 4.1 | 11.6 | 4.1 | | 58.4 | 46.4 | 46.4 | 9.3 | 58.4 |
| 40 | | | 1.8 | | 1.8 | | 1.8 | 1.8 | | 7.3 | 5.2 |
| 41 | 9.2 | | 9.2 | 9.2 | 36.6 | | 9.2 | 9.2 | | 9.2 | 9.2 |
| 26 | | | 1.9 | | 1.9 | | 4.3 | 1.9 | | 1.9 | 10.9 |
| 3 | | | | | | | 60.0 | | | 60.0 | |
| 30 | | | | | | | 21.8 | | | 9.7 | |
| 18 | | | 46.4 | | 23.2 | | 2.9 | 11.6 | | 46.4 | |
| 21 | 10.6 | | 21.2 | 10.6 | 10.6 | | 11.9 | 10.6 | 10.6 | 10.6 | 10.6 |
| 19 | 14.7 | | 14.7 | 11.6 | 14.7 | | 14.7 | 14.7 | 14.7 | 14.7 | 14.7 |
| 44 | 41.3 | | 26.0 | 13.1 | 10.4 | | 11.6 | 9.2 | 13.1 | 10.4 | 13.1 |
| 45 | 52.0 | | 52.0 | 41.3 | 52.0 | | 52.0 | 52.0 | 41.3 | 41.3 | 41.3 |
| 46 | 57.0 | | 50.8 | 45.2 | 12.8 | | 57.0 | 50.8 | 50.8 | 57.0 | 50.8 |
| 47 | 11.4 | | 25.4 | 2.3 | 10.1 | | 5.1 | 11.4 | 12.8 | 57.0 | 12.8 |
| 48 | 59.6 | | 59.6 | 23.7 | 47.3 | | 59.6 | 47.3 | 9.4 | 47.3 | 9.4 |
| 49 | 59.6 | | 47.3 | 47.3 | 53.1 | | 11.9 | 47.3 | 59.6 | 47.3 | 59.6 |
| 50 | 14.3 | | 57.0 | 14.3 | 11.4 | | 14.3 | 11.4 | 14.3 | 45.2 | 14.3 |
| 51 | 15.0 | | 59.8 | 15.0 | 47.5 | | 11.9 | 13.4 | 15.0 | 59.8 | 15.0 |
| 52 | 15.0 | | 47.5 | 15.0 | 11.9 | | 2.4 | 11.9 | 15.0 | 15.0 | 15.0 |
| 163 | | | | | | | 0.31 | | | 1 | |
| 164 | | | | | | | 0.31 | | | 1.4 | |
| 70 | | | 2.18 | | 1.73 | | 0.35 | 1.73 | | 1.73 | 10.92 |
| 107 | | | 1.98 | | 1.98 | | 0.39 | 1.98 | | 1.98 | |
| 103 | | | | | | | 0.4 | | | 1.8 | |
| 53 | | | 1.64 | | 8.23 | | 0.41 | 1.64 | | 1.64 | 9.2 |
| 159 | | | 1.85 | | 1.85 | | 0.41 | 1.47 | | 1.85 | |
| 75 | | | 4.03 | | 2.02 | | 0.9 | 1.8 | | 2.02 | 11.36 |
| 74 | | | 9.03 | | 10.13 | | 0.9 | 9.03 | | 11.36 | |

TABLE 10-continued

IC$_{90}$ values (µg/ml) determined according to the Microtitre plate assay.

| Comp. N°. | BSU 43639 | EFA 14506 | EFA 29212 | LMO 49594 | PAE 27853 | SMU 33402 | SPN 6305 | SPY 8668 | STA 25923 | STA 29213 | STA RMETH |
|---|---|---|---|---|---|---|---|---|---|---|---|
| 173 | | | 2.03 | | 2.03 | | 0.91 | 0.91 | | 2.03 | |
| 158 | | | 1.94 | | 0.87 | | 1.22 | 0.87 | | 0.4 | |
| 72 | | | | | | | 1.61 | | | 2.02 | 2.55 |
| 82 | | | | | | | 1.65 | | | 1.65 | 10.39 |
| 83 | | | | | | | 1.65 | | | 1.65 | 5.21 |
| 71 | | | 8.68 | | 8.68 | | 1.73 | 3.88 | | 1.73 | 10.92 |
| 127 | | | | | | | 1.73 | | | 1.73 | |
| 128 | | | | | | | 1.73 | | | 1.73 | |
| 1 | | | 6.92 | | 1.95 | | 1.74 | 1.74 | | 1.74 | 12.3 |
| 129 | | | | | | | 1.74 | | | 6.19 | |
| 123 | | | | | | | 1.79 | | | 2.26 | |
| 102 | | | 10.11 | | 2.02 | | 1.8 | 2.02 | | 10.11 | |
| 94 | | | | | | | 1.81 | | | 4.06 | |
| 77 | | | | | | | 1.84 | | | 1.84 | |
| 78 | | | | | | | 1.84 | | | 1.84 | |
| 64 | | | 1.85 | | 0.46 | | 1.85 | 1.85 | | 1.85 | |
| 66 | | | | | | | 1.85 | | | 1.85 | |
| 97 | | | | | | | 1.91 | | | 1.91 | |
| 166 | | | | | | | 1.91 | | | 1.91 | |
| 165 | | | | | | | 1.91 | | | 3.81 | |
| 85 | | | | | | | 1.93 | | | 1.93 | 12.2 |
| 137 | | | 9.77 | | 9.77 | | 1.95 | 1.95 | | 1.95 | 12.3 |
| 121 | | | | | | | 1.96 | | | 8.77 | |
| 122 | | | | | | | 1.96 | | | 1.75 | 11.05 |
| 106 | | | 1.98 | | 1.98 | | 1.98 | 1.98 | | 1.98 | |
| 141 | | | 4.46 | | 4.46 | | 1.99 | 4.46 | | 1.99 | 14.12 |
| 104 | | | | | | | 2.04 | | | 1.82 | 12.86 |
| 116 | | | | | | | 2.04 | | | 5.76 | |
| 99 | | | | | | | 2.04 | | | 1.81 | |
| 98 | | | | | | | 2.04 | | | 1.81 | |
| 175 | | | | | | | 2.06 | | | 1.84 | |
| 176 | | | | | | | 2.06 | | | 1.84 | |
| 162 | | | | | | | 2.07 | | | 1.85 | |
| 160 | | | | | | | 2.07 | | | 1.85 | |
| 161 | | | | | | | 2.07 | | | 1.85 | |
| 132 | | | | | | | 2.09 | | | 2.09 | 11.76 |
| 111 | | | | | | | 2.09 | | | 9.33 | |
| 80 | | | | | | | 2.12 | | | 1.89 | 2.38 |
| 133 | | | | | | | 2.13 | | | 1.9 | 12 |
| 134 | | | | | | | 2.13 | | | 4.26 | 12 |
| 138 | | | 1.74 | | 2.19 | | 2.19 | 0.87 | | 2.45 | 12.3 |
| 167 | | | | | | | 2.19 | | | 1.95 | |
| 96 | | | | | | | 2.21 | | | 4.42 | 9.88 |
| 126 | | | | | | | 2.21 | | | 4.41 | 5.55 |
| 148 | | | | | | | 2.23 | | | 1.99 | |
| 149 | | | | | | | 2.23 | | | 1.99 | |
| 131 | | | | | | | 2.24 | | | 1.78 | 11.2 |
| 89 | | | 11.2 | | 11.2 | | 2.24 | 8.9 | | 11.2 | |
| 124 | | | 9 | | 3.58 | | 2.26 | 9 | | 1.79 | |
| 178 | | | | | | | 2.27 | | | 2.02 | |
| 95 | | | | | | | 2.28 | | | 10.2 | |
| 172 | | | | | | | 2.28 | | | 2.03 | |
| 92 | | | | | | | 2.29 | | | 11.48 | |
| 105 | | | | | | | 2.29 | | | 2.04 | 11.46 |
| 115 | | | | | | | 2.29 | | | | |
| 117 | | | | | | | 2.29 | | | 9.13 | |
| 144 | | | 1.82 | | 1.82 | | 2.29 | 1.82 | | 9.12 | |
| 145 | | | 9.12 | | 9.12 | | 2.29 | 5.13 | | 5.76 | |
| 56 | | | | | | | 2.31 | | | 1.84 | 5.81 |
| 57 | | | | | | | 2.31 | | | 4.11 | 2.59 |
| 63 | | | | | | | 2.32 | | | 1.85 | |
| 65 | | | | | | | 2.32 | | | 1.85 | |
| 76 | | | | | | | 2.34 | 10.46 | | | |
| 108 | | | | | | | 2.34 | | | 8.31 | |
| 87 | | | | | | | 2.36 | | | 1.88 | 2.36 |
| 142 | | | | | | | 2.37 | | | 2.65 | 2.37 |
| 135 | | | | | | | 2.4 | | | 1.91 | 12.02 |
| 136 | | | | | | | 2.4 | | | 1.91 | 5.37 |
| 86 | | | | | | | 2.43 | | | 2.17 | 2.17 |
| 156 | | | | | | | 2.43 | | | 1.93 | |
| 168 | | | 1.95 | | 1.95 | | 2.46 | 1.95 | | 2.19 | |
| 90 | | | | | | | 2.51 | | | 2.24 | |
| 91 | | | | | | | 2.51 | | | 2.24 | 12.57 |

TABLE 10-continued

IC$_{90}$ values (μg/ml) determined according to the Microtitre plate assay.

IC$_{90}$ (μg/ml)

| Comp. N°. | BSU 43639 | EFA 14506 | EFA 29212 | LMO 49594 | PAE 27853 | SMU 33402 | SPN 6305 | SPY 8668 | STA 25923 | STA 29213 | STA RMETH |
|---|---|---|---|---|---|---|---|---|---|---|---|
| 169 | | | | | | | 2.52 | | | 4 | |
| 112 | | | 2.02 | | 2.02 | | 2.54 | 2.02 | | 2.02 | 2.54 |
| 113 | | | | | | | 2.54 | | | 14.3 | |
| 73 | | | | | | | 2.55 | | | 2.02 | 2.55 |
| 79 | | | | | | | 2.7 | | | 2.15 | |
| 157 | | | | | | | 2.74 | | | 2.44 | |
| 119 | | | | | | | 4.19 | | | 18.72 | |
| 177 | | | | | | | 4.52 | | | 4.52 | |
| 140 | | | | | | | 4.56 | | | 4.56 | 2.57 |
| 110 | | | | | | | 4.68 | | | 9.33 | |
| 81 | | | 1.89 | | 9.47 | | 4.75 | 1.89 | | 9.47 | |
| 171 | | | | | | | 4.94 | | | 22.07 | |
| 125 | | | | | | | 4.95 | | | 9.87 | |
| 139 | | | | | | | 5.12 | | | 4.56 | 12.86 |
| 118 | | | | | | | 5.14 | | | 8.14 | |
| 109 | | | | | | | 5.25 | | | 9.33 | |
| 61 | | | | | | | 5.43 | | | | |
| 146 | | | | | | | 5.49 | | | 9.76 | |
| 130 | | | | | | | 6.19 | | | 8.74 | |
| 88 | | | | | | | 6.3 | | | 11.2 | |
| 114 | | | | | | | 7.25 | | | | |
| 174 | | | | | | | 8.27 | | | 10.41 | |
| 101 | | | | | | | 9.09 | | | 9.09 | |
| 147 | | | | | | | 9.34 | | | 9.34 | |
| 170 | | | 9.64 | | 9.64 | | 9.64 | 9.64 | | 21.57 | |
| 84 | | | | | | | 9.81 | | | 1.74 | 11 |
| 93 | | | | | | | 9.95 | | | 11.16 | |
| 120 | | | | | | | 10.53 | | | 8.36 | |
| 143 | | | | | | | 10.57 | | | 10.57 | |
| 55 | | | | | | | 10.67 | | | 8.47 | |
| 100 | | | | | | | 11.44 | | | 9.09 | |
| 69 | | | 9.3 | | 7.39 | | 1.65 | 6.59 | | 1.7 | |
| 59 | | | 1.89 | | 1.89 | | 0.84 | 2.12 | | 0.8 | |
| 152 | | | 38.3 | | 38.3 | | 1.5 | 38.3 | | 7.7 | |
| 155 | | | | | | | 1.7 | | | 1.7 | |
| 154 | | | | | 8.68 | | 1.75 | 8.68 | | 1.75 | |
| 58 | | | | | | | 1.9 | | | 4.2 | |
| 150 | | | | | | | 2.1 | | | 1.9 | |
| 151 | | | | | | | 2.12 | | | 1.7 | |
| 60 | | | | | | | 5.4 | | | | |
| 68 | | | 18.6 | | 8.3 | | 1.9 | 1.7 | | 8.3 | |
| 11 | | | 9.0 | | 9.0 | | 9.0 | 9.0 | | 1.8 | 11.4 |
| 16 | | | | | | | 8.5 | | | 8.5 | |
| 42 | | | | | | | 53.2 | | | | |
| 29 | | | 46.3 | | 20.7 | | 9.3 | 20.7 | | 1.9 | 2.3 |
| 37 | | | | | | | 1.8 | | | 2.0 | 10.1 |
| 12 | | | | | | | 11.4 | | | 45.2 | |
| 32 | | | 1.9 | | 1.9 | | 1.9 | 1.9 | | 1.9 | 11.6 |
| 13 | | | | | | | 25.4 | | | | |
| 10 | | | | | | | 10.3 | | | 11.5 | |
| 43 | | | | | | | 53.2 | | | 21.2 | |
| 36 | | | | | | | 9.0 | | | 8.0 | |
| 33 | | | 46.3 | | 52.0 | | 9.3 | 46.3 | | 4.1 | 5.8 |
| 14 | | | | | | | 57.0 | | | 14.3 | |
| 28 | | | | | | | 58.4 | | | 1.9 | 9.3 |
| 15 | | | | | | | 53.5 | | | 53.5 | |
| 9 | | | | | | | 11.5 | | | 9.1 | |
| 153 | | | | | | | 7.65 | | | 3.8 | |

BSU 43639 means *Bacillus subtilis* (ATCC43639); EFA 14506 means *Enterococcus faecalis* (ATCC14506); EFA 29212 means *Enterococcus faecalis* (ATCC29212); LMO 49594 means *Listeria monocytogenes* (ATCC49594); PAE 27853 means *Pseudomonas aeruginosa* (ATCC27853); SMU 33402 means *Streptococcus mutans* (ATCC33402); SPN 6305 means *Streptococcus pneumoniae* (ATCC6305); SPY 8668 means *Streptococcus pyogenes* (ATCC8668); STA 43300 means *Staphylococcus aureus* (ATCC43300); STA 25923 means *Staphylococcus aureus* (ATCC25923); STA 29213 means *Staphylococcus aureus* (ATCC29213); STA RMETH means methicilline resistant *Staphylococcus aureus* (MRSA) (a clinical isolate from the University of Antwerp).
ATCC means American type tissue culture.

The invention claimed is:

1. A method of treating a bacterial infection in a mammal, wherein the bacterial infection is *Staphylococcus aureus, Enterococcus faecalis, Pseudomonas aeruginosa* or *Streptococcus pneumoniae*, said method comprising administering an effective amount of a compound of formula (Ia) or (Ib) to said mammal

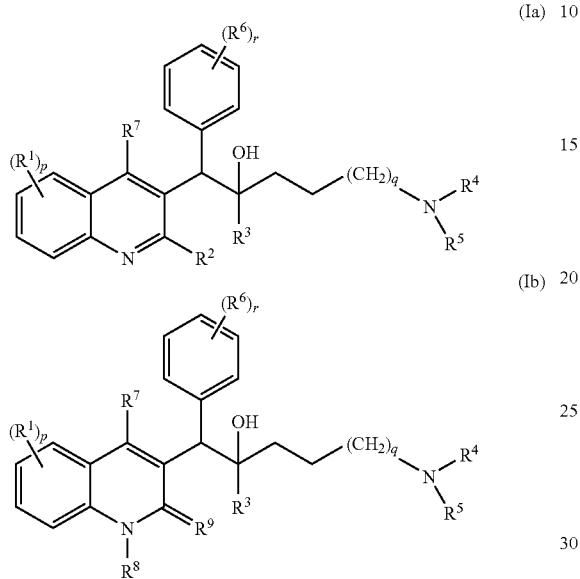

a pharmaceutically acceptable acid or base addition salt thereof, a stereochemically isomeric form thereof, a tautomeric form thereof or a N-oxide form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2, 3 or 4;

$R^2$ is hydrogen, hydroxy, mercapto, alkyloxy, alkyloxyalkyloxy, alkylthio, mono or di(alkyl)amino or a radical of formula

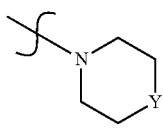

wherein Y is $CH_2$, O, S, NH or N-alkyl;

$R^3$ is alkyl, Ar, Ar-alkyl, Het or Het-alkyl;

q is an integer equal to 1, 2 or 3;

$R^4$ and $R^5$ each independently are hydrogen, alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl or pyrimidinyl;

$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^6$ radicals may be taken together to form a bivalent radical of formula —CH=CH—CH=CH—;

r is an integer equal to 1, 2, 3, 4 or 5;

$R^7$ is hydrogen, alkyl, Ar or Het;

$R^8$ is hydrogen or alkyl;

$R^9$ is oxo;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;

Ar is a homocycle selected from the group of phenyl, naphthyl, acenaphthyl, tetrahydronaphthyl, each homocycle optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl and benzo[1,3]dioxolyl; each monocyclic and bicyclic heterocycle may optionally be substituted with 1, 2 or 3 substituents, each substituent independently selected from the group of halo, hydroxy, alkyl, alkyloxy, and Ar-carbonyl;

halo is a substituent selected from the group of fluoro, chloro, bromo and iodo; and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms.

2. A method according to claim 1 wherein the compound of formula (Ia) or (Ib) is a compound having the following formula

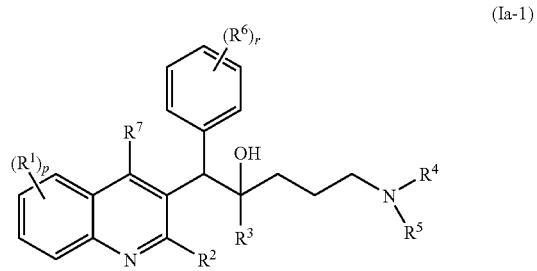

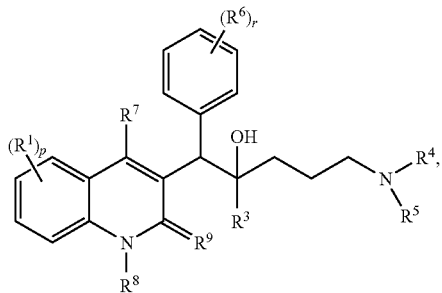
(Ib-1)

a pharmaceutically acceptable acid or base addition salt thereof, a stereochemically isomeric form thereof, a tautomeric form thereof or a N-oxide form thereof.

3. A method according to claim 1 wherein the compound of formula (Ia) or (Ib) is a compound having the following formula

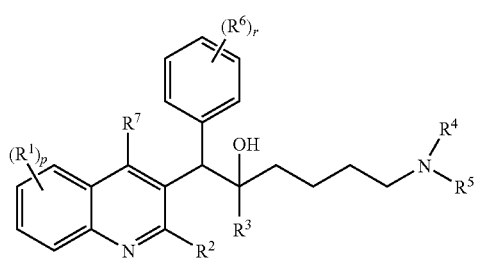
(Ia-2)

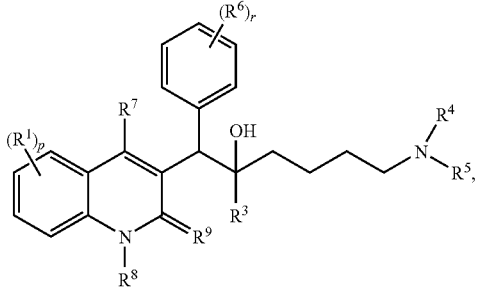
(Ib-2)

a pharmaceutically acceptable acid or base addition salt thereof, a stereochemically isomeric form thereof, a tautomeric form thereof or a N-oxide form thereof.

4. A method according to claim 1 wherein the compound of formula (Ia) or (Ib) is a compound having the following formula

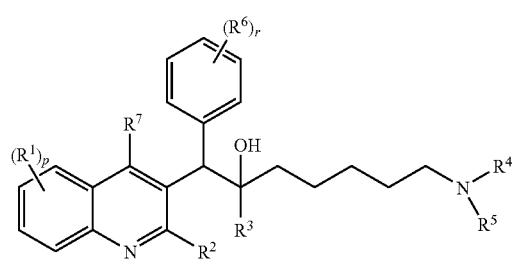
(Ia-3)

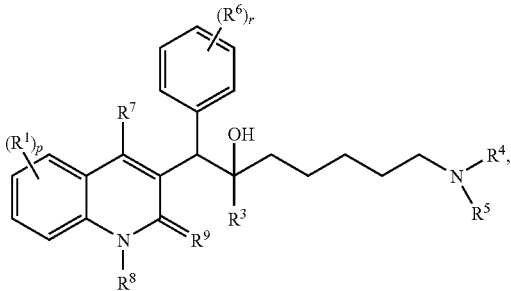
(Ib-3)

a pharmaceutically acceptable acid or base addition salt thereof, a stereochemically isomeric form thereof, a tautomeric form thereof or a N-oxide form thereof.

5. A method according to claim 1 wherein $R^1$ is hydrogen, halo, Ar, Het or alkyl.
6. A method according to claim 5 wherein $R^1$ is hydrogen, halo, Ar or Het.
7. A method according to claim 6 wherein $R^1$ is halo or Het.
8. A method according to claim 7 wherein $R^1$ is halo.
9. A method according to claim 1 wherein p is equal to 1.
10. A method according to claim 1 wherein $R^2$ is alkyloxy or alkylthio.
11. A method according to claim 10 wherein $R^2$ is $C_{1-4}$-alkyloxy.
12. A method according to claim 1 wherein $R^3$ is Ar, Het Ar-alkyl or Het-alkyl.
13. A method according to claim 1 wherein $R^3$ is $C_{1-4}$-alkyl, naphthyl, phenyl optionally substituted with alkyl or alkyloxy, pyridinyl, benzo[1,3]dioxolyl, —CH$_2$—(CH$_2$)$_n$—$R^{3a}$ wherein $R^{3a}$ is cyclohexyl, phenyl, naphthyl or furanyl, $R^{3a}$ optionally being substituted with alkyl, and wherein n is 0 or 1.
14. A method according to claim 13 wherein $R^3$ is naphthyl or phenyl.
15. A method according to claim 1 wherein $R^4$ and $R^5$ each independently are hydrogen or $C_{1-4}$-alkyl.
16. A method according to claim 1 wherein $R^4$ and $R^5$ together and including the N to which they are attached form a radical selected from the group of pyrrolidinyl, piperidinyl, piperazinyl or morpholinyl, optionally substituted with alkyl, amino or mono- or di(alkyl)amino.
17. A method according to claim 1 wherein $R^6$ is hydrogen or halo.
18. A method according to claim 1 wherein $R^6$ is hydrogen.
19. A method according to claim 1 wherein r is equal to 1.
20. A method according to claim 1 wherein $R^7$ is hydrogen.
21. A method according to claim 1 wherein the compound is a compound according to formula (Ia).
22. A method according to claim 1 wherein the compound is a compound of formula (Ia)
wherein $R^1$ is hydrogen, halo, alkyl, Ar or Het; p=1; $R^2$ is alkyloxy, alkylthio or a radical of formula

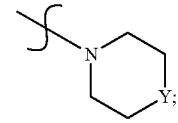

$R^3$ is alkyl, Ar, Het, Ar-alkyl or Het-alkyl; q=1, 2 or 3; $R^4$ and $R^5$ each independently are hydrogen, alkyl or benzyl; or $R^4$ and $R^5$ together and including the N to which they are attached form a radical selected from the group of pyrrolidinyl, piperidinyl, piperazinyl or morpholinyl, optionally substituted with alkyl or mono- or di(alkyl)amino; $R^6$ is hydrogen, halo, alkyloxy, alkyl or phenyl optionally substituted with alkyloxy; r is equal to 1 or 2; $R^7$ is hydrogen.

23. A method according to claim 1 wherein the compound is selected from the following compounds

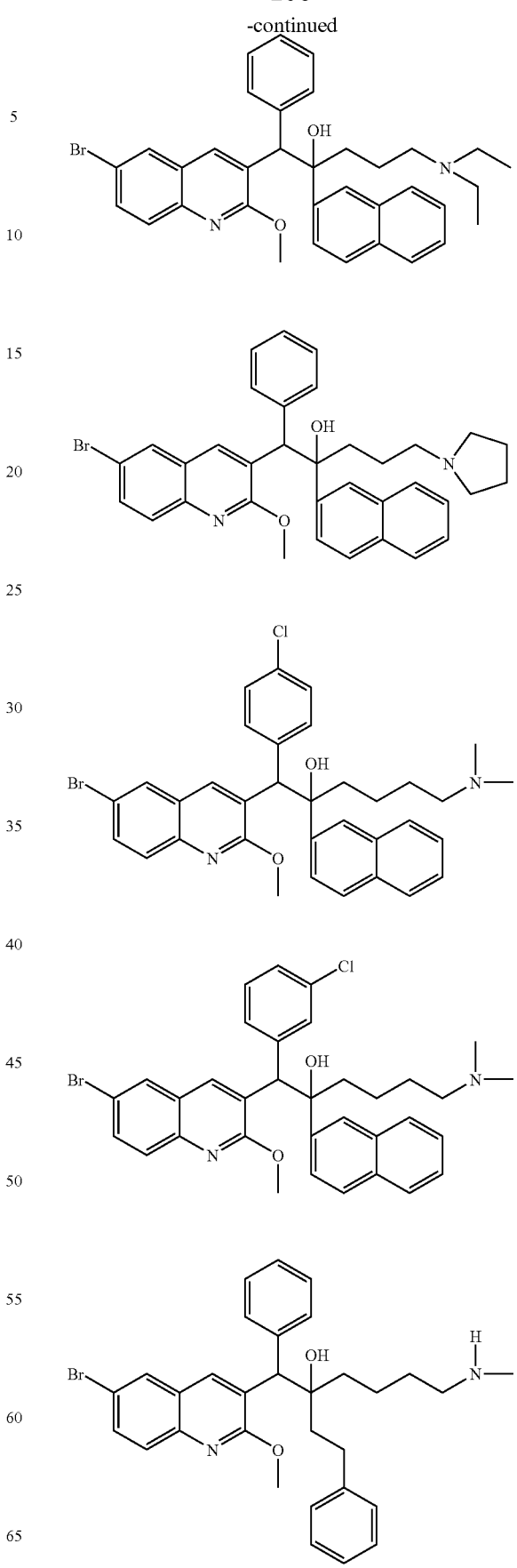

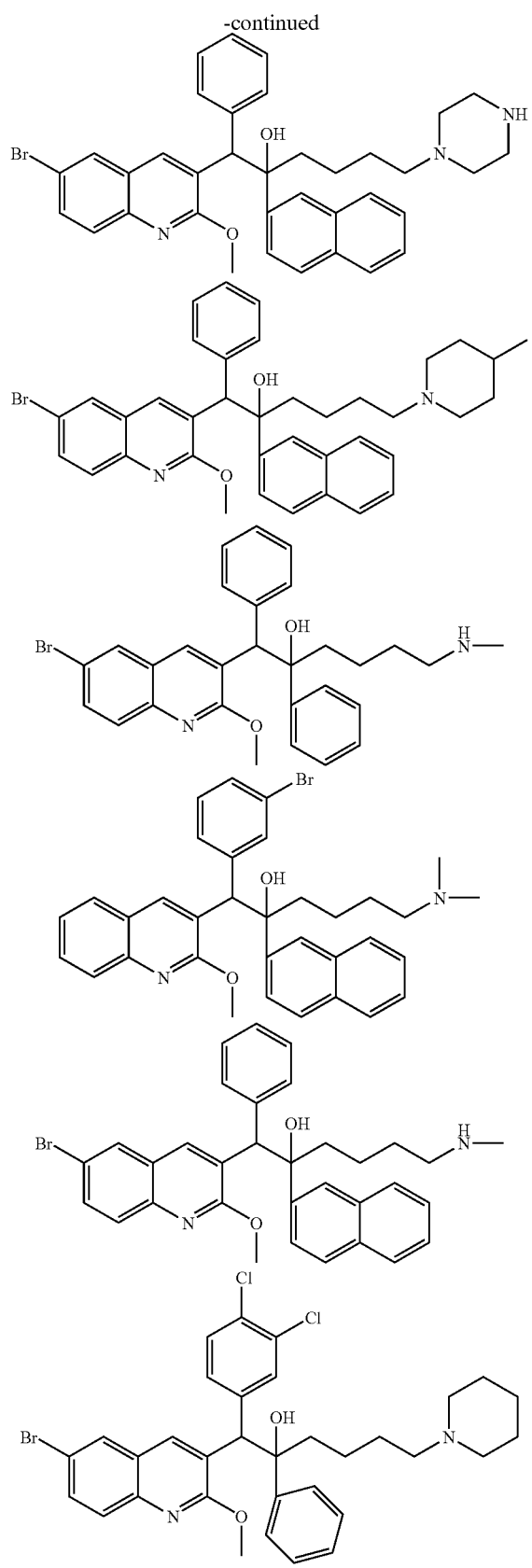

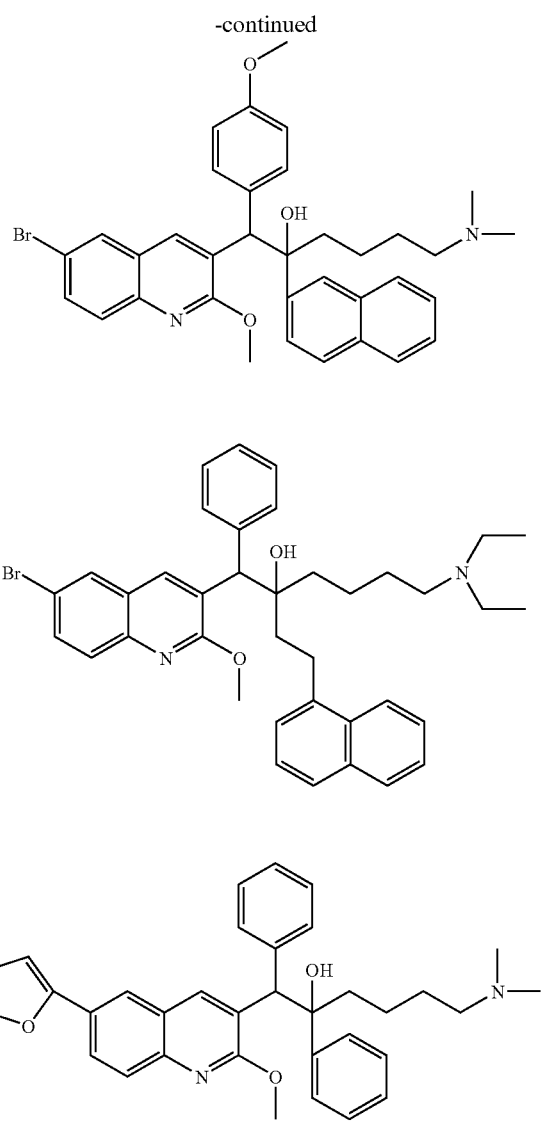

a pharmaceutically acceptable acid or base addition salt thereof, a stereochemically isomeric form thereof, a tautomeric form thereof or a N-oxide form thereof.

24. A method according to claim 1 wherein the bacterial infection is an infection with a gram-positive bacterium.

25. A method according to claim 24 wherein the gram-positive bacterium is *Staphylococcus aureus* or *Streptococcus pneumoniae*.

26. A method of treating a bacterial infection in a mammal comprising administering an effective amount of pharmaceutical composition to said mammal, wherein the pharmaceutical composition comprises a pharmaceutically acceptable carrier, and as active ingredient, a therapeutically effective amount of (a) a compound of formula (Ia) or (Ib) as defined in claim 1, and (b) one or more other antibacterial agents provided that the one or more other antibacterial agents are other than antimycobacterial agents.

\* \* \* \* \*